United States Patent
Rovnyak et al.

[11] Patent Number: 5,837,702
[45] Date of Patent: Nov. 17, 1998

[54] 4-ARYLAMINO-BENZOPYRAN AND RELATED COMPOUNDS

[75] Inventors: George C. Rovnyak, Hopewell, N.J.; Karnail S. Atwal, Newton, Pa.; Dinos P. Santafianos, Maplewood; Charles Z. Ding, Plainsboro, both of N.J.

[73] Assignee: Bristol-Myers Squibb Co., Princeton, N.J.

[21] Appl. No.: 296,341

[22] Filed: Aug. 30, 1994

Related U.S. Application Data

[63] Continuation-in-part of Ser. No. 134,034, Oct. 7, 1993, abandoned.

[51] Int. Cl.[6] .......... A01N 43/16; A01N 31/535; A01N 43/64; A01N 43/40
[52] U.S. Cl. .......... 514/218; 514/233.5; 514/233.8; 514/253; 514/275; 514/337; 514/340; 514/373; 514/374; 514/375; 514/382; 514/397; 514/414; 514/422; 514/456; 540/524; 544/114; 544/133; 544/138; 544/151; 544/238; 544/297; 544/360; 546/269.4; 546/275.1; 546/283.1; 548/112; 548/131; 548/159; 548/190; 548/198; 548/222; 548/236; 548/252; 548/254; 548/266.4; 548/305.1; 548/413; 548/452; 548/525
[58] Field of Search .......... 549/356, 404, 549/220, 331, 394; 540/524; 546/269.4, 283.1, 275.1; 548/112, 190, 198, 252, 253, 254, 413, 525, 159, 222, 452, 311.4, 261.4, 131, 236, 305.1; 544/151, 138, 297, 360, 114, 238, 133; 514/456, 382, 422, 233.5, 374, 414, 397, 375, 233.8, 340, 275, 373, 253, 337

[56] References Cited

U.S. PATENT DOCUMENTS

| | | | |
|---|---|---|---|
| 3,330,838 | 7/1967 | Augstein et al. | 260/309.6 |
| 3,812,157 | 5/1974 | Lin et al. | 260/345.2 |
| 4,238,501 | 12/1980 | Kabbe et al. | 424/283 |
| 4,251,537 | 2/1981 | Evans | 424/267 |
| 4,363,811 | 12/1982 | Evans et al. | 424/267 |
| 4,366,163 | 12/1982 | Evans et al. | 424/267 |
| 4,391,815 | 7/1983 | Evans | 424/274 |
| 4,481,213 | 11/1984 | Evans | 424/283 |
| 4,568,692 | 2/1986 | Evans | 514/456 |
| 4,571,406 | 2/1986 | Evans et al. | 514/456 |
| 4,575,511 | 3/1986 | Evans et al. | 514/456 |
| 4,602,022 | 7/1986 | Cozzi et al. | 514/337 |
| 4,659,737 | 4/1987 | Kabbe et al. | 514/456 |
| 4,687,779 | 8/1987 | Evans | 514/456 |
| 4,734,421 | 3/1988 | Hammond et al. | 514/274 |
| 4,772,603 | 9/1988 | Evans | 514/241 |
| 4,782,083 | 11/1988 | Cassidy et al. | 514/456 |
| 4,831,050 | 5/1989 | Cassidy et al. | 514/422 |
| 4,904,784 | 2/1990 | Evans et al. | 546/90 |
| 4,925,839 | 5/1990 | Quagliato et al. | 514/212 |
| 4,943,582 | 7/1990 | Evans et al. | 514/320 |
| 4,971,982 | 11/1990 | Attwood et al. | 514/337 |
| 4,988,723 | 1/1991 | Shiokawa et al. | 514/392 |
| 5,006,523 | 4/1991 | Atwal | 514/227.8 |
| 5,011,837 | 4/1991 | Atwal et al. | |
| 5,013,853 | 5/1991 | Gericke et al. | 549/401 |
| 5,021,432 | 6/1991 | Yamanaka et al. | 514/337 |
| 5,028,711 | 7/1991 | Stenzel et al. | 546/196 |
| 5,053,427 | 10/1991 | Stemp et al. | 514/456 |
| 5,061,813 | 10/1991 | Atwal | 549/399 |
| 5,071,871 | 12/1991 | Blarer et al. | 514/456 |
| 5,082,858 | 1/1992 | Garcia et al. | 514/456 |
| 5,095,016 | 3/1992 | Ohtuka et al. | 514/233.5 |
| 5,096,914 | 3/1992 | Stenzel et al. | 514/392 |
| 5,104,890 | 4/1992 | Shiokawa et al. | 514/370 |
| 5,140,031 | 8/1992 | Atwal et al. | 514/302 |
| 5,143,924 | 9/1992 | Gericke et al. | 514/337 |
| 5,143,936 | 9/1992 | Yamanaka et al. | 514/456 |
| 5,145,985 | 9/1992 | Timar et al. | 548/525 |
| 5,210,234 | 5/1993 | Evans et al. | 549/398 |
| 5,238,937 | 8/1993 | Gericke et al. | 514/253 |
| 5,254,555 | 10/1993 | Stemp et al. | 514/256 |
| 5,276,168 | 1/1994 | Atwal | 549/404 |
| 5,286,753 | 2/1994 | Schaus et al. | 514/657 |
| 5,310,750 | 5/1994 | Berge et al. | 514/402 |
| 5,317,029 | 5/1994 | Inazu et al. | 514/422 |
| 5,318,969 | 6/1994 | Yamanaka et al. | 514/247 |

FOREIGN PATENT DOCUMENTS

| | | |
|---|---|---|
| 0274821 | 10/1986 | European Pat. Off. . |
| 0205292 | 12/1986 | European Pat. Off. . |
| 0214818 | 3/1987 | European Pat. Off. . |
| 0 339 562 | 11/1989 | European Pat. Off. . |
| 0344747 | 12/1989 | European Pat. Off. . |
| 0350805 | 1/1990 | European Pat. Off. . |
| 0359537 | 1/1990 | European Pat. Off. . |
| 0389861 | 3/1990 | European Pat. Off. . |
| 0412531 | 2/1991 | European Pat. Off. . |
| 0 431 741 | 6/1991 | European Pat. Off. . |
| 0 525768 | 2/1993 | European Pat. Off. . |
| 2 204 868 | 11/1988 | United Kingdom . |
| WO8707607 | 12/1987 | WIPO . |

OTHER PUBLICATIONS

H.J. Petersen et al., "Synthesis and Hypotensive Activity of N–Alkyl–N–cyano–N'–pyridylguanidines", *J. of Med. Chem.*, vol. 21, No. 8, (Aug. 1978), pp. 773–781.

(List continued on next page.)

*Primary Examiner*—John Kight
*Assistant Examiner*—Raymond Covington
*Attorney, Agent, or Firm*—Prabodh I. Almaula

[57] ABSTRACT

Compounds having the formula

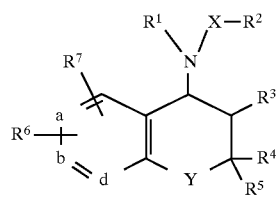

and pharmaceutically acceptable salts thereof wherein X is alkyl, Y is a single bond, —$CH_2$—, —C(O)—, —O—, —S— or —N($R^8$)— where $R^8$ is hydrogen, alkyl, haloalkyl, aryl, arylalkyl, cycloalkyl or (cycloalkyl)alkyl, and $R^1$ to $R^7$ are as defined herein. These compounds have potassium channel activating activity and are useful, therefore for example, as cardiovascular agents.

8 Claims, No Drawings

OTHER PUBLICATIONS

V.A. Ashwood et al., "Synthesis and Antihypertensive Activity of 4-(Cyclic amido)-2H-1-benzopyrans", *J. Med. Chem.*, (1986) 29, pp. 2194–2201.

C.R. Rasmussen et al., "Improved Procedures for the Preparation of Cycloalkyl-, Arylalkyl-, and Arylthioureas", *Synthesis*, (Jun. 1988), pp. 456–459.

V.V. Mozolis et al., "Preparation of N–Substituted Thiourea", *Russian Chem. Reviews*, 42(7), (1973), pp. 587–595.

J.M. Evans et al., "Synthesis and Antihypertensive Activity of Substituted trans-4-Amino-3,4-dihydro-2,2-dimethyl-2H-1-benzopyran-3-ols", *J. Med. Chem.*, (1983), 26, pp. 1582–1589.

R.W. Lang et al., "Synthesis of Selectively Trifluoromethylated Pyridine Derivatives as Potential Antihypertensives", *Helvetica Chimica Acta*, (1988), vol. 71, pp. 596–601.

P. Sebok et al., "Selective synthesis of Analogues of the Natural Precocenes, Synthesis and Regioselective (–Alkylation of 6–Chloro–and 6–Tert–Butyl–7,8–Dihyedroxy–2,2–Dimethyl–4–Chromanones", *Heterocycles*, (1988), 27, pp. 2595–2607.

P. Teixidor et al., "Improved Preparation of Precocene II, Unexpected Results in the Reduction of Alkoxy Substituted Acetophenones and 4–Chromanones with Sodium Borohydride", *Hetercycles*, (1988), 27, pp. 2459–2465.

A. Banerji et al., "Enolates of o–Hydroxyacetophenones: Novel Synthesis of 2,2–Dialkyl–4–Chromanones", *Tetrahedron Letters*, No. 38, 1979, pp. 3685–3686.

G. Ariamala et al., "Simple Route for the Synthesis of 4–Chlorochromenes and Chroman–4–ones", *Tetrahedron Letters*, (1988), vol. 29, No. 28, pp. 3487–3488.

4-ARYLAMINO-BENZOPYRAN AND RELATED COMPOUNDS

This application is a continuation-in-part of U.S. application Ser. No. 08/134,034, filed Oct. 7, 1993 now abandoned; incorporated by reference herein.

BRIEF DESCRIPTION OF THE INVENTION

The present invention is directed to compounds of the formula

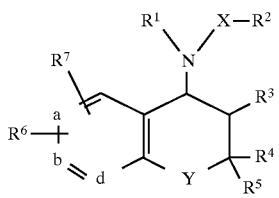

and pharmaceutically acceptable salts thereof. As used in formula I, and throughout the specification, the symbols have the following meanings:

a, b and d are all carbon atoms or one of a, b and d is a nitrogen atom or —N(O)— and the others are carbon atoms;

Y is a single bond, —CH$_2$—, —C(O)—, —O—, —S— or —N(R$^8$)—;

R$^1$ is aryl or heterocyclo;

R$^2$ is —COOR$^8$, —CO-amino, —CO-substituted amino, amino, substituted amino, —NR$^8$CO-amino, —NR$^8$CO-substituted amino, —NR$^8$COR$^9$, —NR$^8$SO$_2$R$^9$, —NR$^8$(C=NCN)-amino, —NR$^8$(C=NCN)-substituted amino,

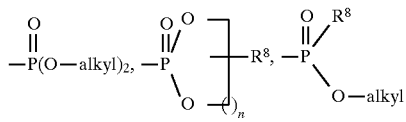

—SR$^8$, —SOR$^8$, —SO$_2$R$^8$, —OR$^8$, cyano, heterocyclo, pyridine-N-oxide, —CH(OR$^8$)$_2$,

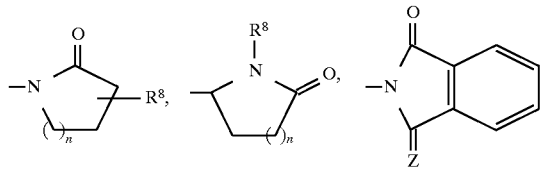

(where Z is O or H$_2$) or

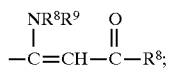

R$^3$ is hydrogen, hydroxy or —OC(O)R$^8$;

R$^4$ and R$^5$ are each independently hydrogen, alkyl or arylalkyl, or R$^4$ and R$^5$ taken together with the carbon atom to which they are attached form a 5- to 7-membered carbocyclic ring;

R$^6$ is hydrogen, alkyl, haloalkyl, alkenyl, alkynyl, cycloalkyl, arylalkyl, (cycloalkyl)alkyl, —CN, —NO$_2$, —COR$^8$, —COOR$^8$, —CONHR$^8$, —CONR$^8$R$^9$, —CF$_3$, —S—alkyl, —SOalkyl, —SO$_2$alkyl,

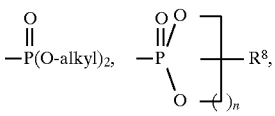

halogen, amino, substituted amino, —O—alkyl, —OCF$_3$, —OCH$_2$CF$_3$, —OCOalkyl, —OCONR$^8$alkyl, —NR$^8$COalkyl, —NR$^8$COOalkyl or —NR$^8$CONR$^9$, tetrazolyl, imidazole, oxazole or triazole;

R$^7$ is hydrogen, alkyl, hydroxy, —O—alkyl, amino, substituted amino, —NHCOR$^8$, —CN or —NO$_2$;

R$^8$ and R$^9$ are independently hydrogen, alkyl, haloalkyl, aryl, arylalkyl, cycloalkyl or (cycloalkyl)alkyl;

X is alkyl; or X—R$^2$ together can be hydrogen, aryl or heterocyclo when R$^1$ is heterocyclo; and n is an integer of 1 to 3.

The compounds of this invention possess antiischemic activity and are useful, for example as cardiovascular agents.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances either individually or as part of a larger group).

The term "alkyl" refers to both straight and branched chain groups having 1 to 8 carbon atoms preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like as well as such groups having a halo substituent (such as CCl$_3$ or CF$_3$), an alkoxy substituent, an aryl substituent, an alkylaryl substituent, a haloaryl substituent, a cycloalkyl substituent, a (cycloalkyl)alkyl substituent, a hydroxy substituent, an alkylamino substituent, an alkyl-substituted amino substituent, an alkanoylamino substituent, an arylcarbonylamino substituent, a nitro substituent, a cyano substituent, a thiol substituent or an alkylthio substituent.

The term "alkoxy" refers to any of the above alkyl groups linked to an oxygen atom.

The term "alkylthio" refers to any of the above alkyl groups linked to a sulfur atom.

The term "alkenyl" refers to any of the above alkyl groups further containing at least one carbon to carbon double bond.

The term "alkynyl" refers to any of the above alkyl groups further containing at least one carbon to carbon triple bond.

The term "cycloalkyl" refers to saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to phenyl, 1-naphthyl, 2-naphthyl; phenyl, 1-naphthyl, 2-naphthyl, mono-substituted with (C$_1$–C$_4$)-alkyl, (C$_1$–C$_4$)-alkylthio, (C$_1$–C$_4$)-alkoxy, halo, nitro, cyano, hydroxy, amino, (alkyl)amino, alkyl-substituted amino, —NH—(C$_1$–C$_4$)-alkyl, —N((C$_1$–C$_4$)-alkyl), —CF$_3$, —OCHF$_2$,

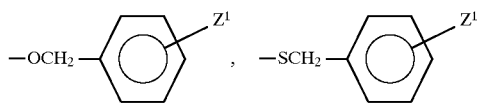

(where $Z^1$ is hydrogen, $(C_1-C_4)$-alkyl, $(C_1-C_4)$-alkylthio, $(C_1-C_4)$-alkoxy, halo, hydroxy or $-CF_3$), $-O-CH_2$-cycloalkyl, or $-S-CH^2$-cycloalkyl; and phenyl, 1-naphthyl or 2-naphthyl, di-substituted with methyl, methoxy, methylthio, halo, $-CF_3$, nitro, amino, $-OCHF_2$, carboxylic acid or carboxylic ester. The term "aryl" also includes those groups listed above fused to a five- or six-membered ring which optionally contains an O, S or N atom (the nitrogen atom being substituted by an $R^7$ group). Preferred aryl groups include unsubstituted phenyl and monosubstituted phenyl wherein the substituents are $(C_1-C_4)$-alkyl, methoxy, halo, nitro, cyano or $-CF_3$.

The term "heterocyclo" or "hetero" refers to fully saturated or unsaturated rings of 5 or 6 atoms containing one or two oxygen or sulphur atoms and/or one to four nitrogen atoms provided that the total number of hetero atoms in the ring is four or less. The hetero ring is attached by way of an available atom. Preferred monocyclic hetero groups include 2- and 3-thienyl, 2- and 3-furyl, 2-, 3- and 4-pyridyl and imidazolyl. The term "hetero" also includes bicyclic rings wherein the five- or six-membered ring containing oxygen or sulphur and/or nitrogen atoms as defined above is fused to a benzene ring and the bicyclic ring is attached by way of an available carbon atom. Preferred bicyclic hetero groups include 4-, 5-, 6- or 7-indolyl, 4-, 5-, 6- or 7-isoindolyl, 5-, 6-, 7- or 8-quinolinyl, 5-, 6- , 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl and 4-, 5-, 6- or 7-benzofuranzanyl.

The term "heterocyclo" or "hetero" also includes such monocyclic and bicyclic rings wherein an available carbon atom is substituted with a $(C_1-C_4)$-alkyl, aryl, $(C_1-C_4)$-alkylthio, $(C_1-C_4)$-alkoxy, halo, nitro, keto, cyano, hydroxy, azo, thiazo, amino, $-NH-(C_1-C_4)$-alkyl, $-N((C_1-C_4)$-alkyl$)_2$, $-CF_3$, (aminoester)alkyl, carboxylic acid, carboxylic ester, $-OCHF_2$ or $(C_1-C_4)$-alkoxy further substituted with a carboxylic acid or such monocyclic and bicyclic rings wherein two or three available carbons have substituents selected from methyl, methoxy, methylthio, halo, $-CF_3$, nitro, hydroxy, amino and $-OCHF_2$.

The term "substituted amino" refers to a group of the formula $-NZ^2Z^3$ wherein $Z^2$ is hydrogen, alkyl, cycloalkyl, aryl, arylalkyl, (cycloalkyl)alkyl, morpholinylalkyl, heterocyclo or (heterocyclo)alkyl and $Z^3$ is hydrogen, alkyl, cycloalkyl, aryl, arylalkyl, haloalkyl, hydroxyalkyl, alkoxyalkyl, thioalkyl, (cycloalkyl)alkyl or hydroxyalkyl further substituted with a carboxylic ester or carboxylic acid, with the proviso that when $Z^2$ is hydrogen, then $Z^3$ is other than hydrogen; or $Z^2$ and $Z^3$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl- 1-piperazinyl, 4-diarylalkyl- 1-piperazinyl, 1-pyrrolidinyl, 1-piperidinyl, or 1-azepinyl, optionally substituted with alkyl, alkoxy, alkylthio, halo, trifluoromethyl or hydroxy.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as $(C_1-C_4)$-alkyl- or aryl-sulfonic acids which are unsubstituted or substituted, for example by halogen, for example methane- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with anmmonia or an organic amine, such as morpholine, thiomorpholine, piperidine, pyrrolidine, a mono-, di- or tri-lower alkylarnine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in diastereomeric forms or in mixtures thereof. The above described processes can utilize racemates, enantiomers or diastereomers as starting materials. When diastereomeric products are prepared, they can be separated by conventional methods for example, chromatographic or fractional crystallization. Preferred compounds are those with the 3R or 4S stereochemistry.

It should be understood that the present invention includes prodrug forms of the compounds of formula I such as alkylesters of acids.

The compounds of the instant invention may, for example, be in the free or hydrate form, and may be obtained by methods exemplified by the following descriptions.

Compounds of formula I where $R^3$ is trans-hydroxy and X is $CH_2$, can be prepared by first reacting an epoxide of formula

II

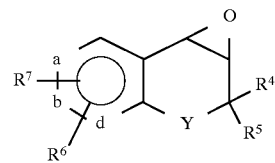

with an amine of formula $R^1-NH_2$            III under heat or preferably in the presence of a Lewis acid such as magnesium perchlorate or trimethylaluminum to provide an intermediate of formula

IV

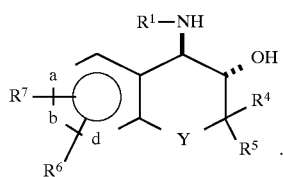

The intermediate of formula IV is then derivatized by reductive amination using an aldehyde of formula

V

HCR² in the presence of a reducing agent such as sodium cyanoborohydride or sodium triacetoxyborohydride. Alternatively, reductive amination can be effected with hydrogen gas in the presence of a catalyst such as palladium on carbon.

Compounds of formula I can also be prepared by reacting an epoxide of formula II with an aminine of formula

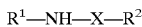
R¹—NH—X—R²    VI in an organic solvent such as acetonitrile in the presence of a Lewis acid such as magnesium perchlorate or cobalt chloride.

Compounds of formula I wherein $R^2$ is CO-amino or CO-substituted amino, can be prepared by reacting compounds of formula I wherein $R^2$ is $COOR^8$ with ammonia or an appropriate amine.

Compounds of formula I where $R^2$ is $NR^8CO$-amino, $NR^8CO$-substituted amino, $NR^8COR^9$, $NR^8SO_2R^9$, $NR^8(C=NCN)$-amino or $NR^8(C=NCN)$-substituted amino can be prepared from compounds of formula I where $R^2$ is amino or substituted amino by methods described in the literature such as those used for acylation, urea formation, sulfonylation and cyanoguanidine formation.

Compounds of formula I where $R^1$ is heterocyclo (e.g., benzoxazole) and $R^3$ is trans-hydroxy can also be prepared by first reacting an epoxide of formula II with an amnine of formula

H₂N—X—R²    VII under heat or in the presence of a Lewis acid (magnesium perchlorate, trimethylaluminum, etc.) to provide an intermediate of formula

VIII

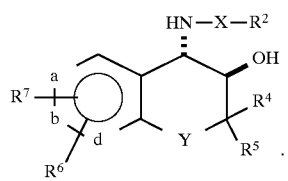

The intermediate of formula VIII is then reacted with a heterocycle containing a leaving group (e.g., 2-chlorobenzoxazole) in the presence of a base such as sodium hydride in an organic solvent such as tetrahydrofuran or dimethylformamide to form compounds of formula I where $R^1$ is heterocyclo and $R^3$ is trans-hydroxy.

Other compounds of formula I wherein $R^1$ is heterocyclo (e.g., oxazole, pyrazole, isonazole etc.) can be prepared from intermediates of formula VIII by standard methods.

Compounds of formula I wherein $R^1$ is heterocyclo (e.g., thiazole) can also be prepared by alkylation of a compound of formula IV with an alkylating agent of formula

L—X—R²    IX where L is a leaving group such as a halogen, mesylate or tosylate.

Compounds of formula I wherein $R^3$ is hydrogen can be prepared from compounds of formula

X

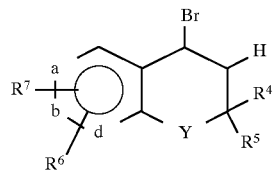

by reaction with an amine of formula VI in the presence of a base such as sodium hydride or potassium carbonate. Alternatively, compounds of formula I where $R^3$ is hydrogen can be prepared by first reacting a compound of formula X with an amine of formula III in the presence of a base (e.g., sodium hydride) to provide a compound of formula

XI

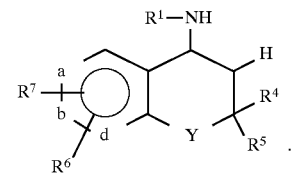

The compound of formula XI is then converted to compounds of formula I where $R^3$ is hydrogen by methods described for the conversion of compounds of formula IV to compounds of formula I.

Compounds of formula XI where $R^3$ is hydrogen can also be prepared from the ketone of formula

XII

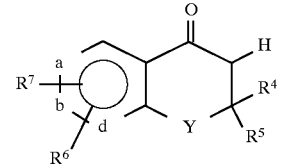

and the amine of formula III by standard techniques of reductive amination.

The ketone of formula XII can be obtained by standard methodology or by literature procedures, such as those disclosed by P. Sebok and T. Timar, *Heterocycles,* 1988, 27, 2595; P. Teixidor et al., *Heterocycles,* 1988, 27, 2459; A. Benerji and N. C. Goomer, *Tetrahedron Letters,* 1979, 3685; and G. Ariamala and K. K. Subramanian, *Tetrahedron Letters,* 1988, 29, No.28, 3487–3488.

The bromide of formula X can be prepared from the olefin of formula

XIII

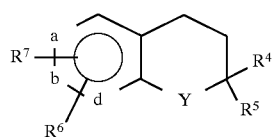

by (a) catalytic hydrogenation of the double bond followed by (b) radical bromination using standard methods. The olefin of formula XIII can be prepared by the methods described for the preparation of compounds of formula II.

Compounds of formula XI where $R^3$ is hydrogen can also be prepared from compounds of formula IV by (a) dehydration of the alcohol with sodium hydride in aprotic solvents such as tetrahydrofuran; and (b) catalytic hydrogenation or reductive amination by sodium cyanoborohydride or sodium triacetoxyborohydride.

If any of the R substitutents, X or Y groups contain reactive groups such as hydroxy or amino that can interfere with the epoxide opening reaction or any other reactions, they should be protected with appropriate protecting groups.

Compounds of formula II wherein Y is a single bond can be prepared according to D. R. Buckle, et al., *J. Med. Chem.*, 1991, 34, 919.

Compounds of formula II wherein Y is $CH_2$ can be prepared by methods described in V. A. Ashwood, et al., *J. Med. Chem.*, 1991, 34, 3261.

Compounds of formula II where Y is oxygen, can be prepared by methods described in the literature, such as by J. M. Evans, et al., *J. Med, Chem.*, 1983, 26, 1582; J. M. Evans, et al., *J. Med. Chem.*, 1986, 29, 2194; R. W. Lang et al., *Helvetica Chimica Acta*, 1988, 71, 596; European patent 0205292 A2 and PCT patent 87/07607.

Compounds of formula II where Y is N(R) can be prepared according to PCT patent 85/050083.

To prepare enantiomers of epoxide II, the olefin of formula XIII is epoxidized with an oxidizing agent such as commercial bleach using a metal catalyst such as chiral manganese catalyst of the formula

XIV

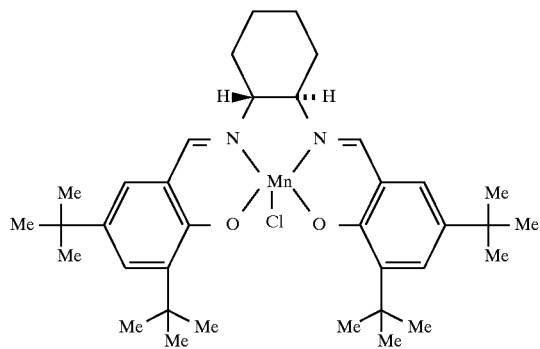

as described by N. H. Lee, et al. (*Tetrahedron Letters*, 1991, 32, 5055–5058), to provide predominantly the chiral epoxide of formula

IIA

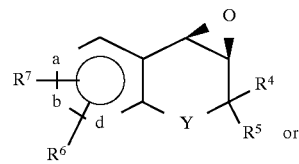

IIB

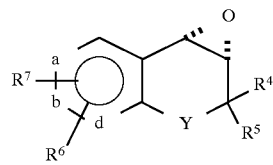

depending on the chirality of the 1,2-diaminocyclohexane used in the preparation of a compound of formula XIV as described by Lee et al.

The epoxides of formulae IIA and IIB can then be utilized to prepare the chiral compounds of formula I.

Compounds of formula I where $R^3$ is $OC(O)R^8$ can be prepared from compounds of formula I where $R^3$ is hydroxy by treatment with an acid chloride of formula $$Cl-C(O)R^8$$

in the presence of a base catalyst such as pyridine or triethylamine.

All other compounds of formula I may be prepared by modification of the procedures discussed herein as known by those skilled in the art. The intermediates used to prepare compounds of formula I are described herein or may be derived from known compounds by those skilled in the art or are commercially available.

The compounds of the present invention can have asymmetric centers at carbons 2–4 of the bicyclic ring. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The antiischemic and antihypertensive effects of benzopyran based and related potassium channel openers are usually stereoselective, with the 3S,4R- enantiomer being the more active isomer. However, it has been unexpectedly found that compounds of formula I are "selective antiischemic agents" with the 3R,4S-enantiomer being the more potent isomer. The term "selective antiischemic agent" means that these compounds possess little or no vasodilator activity (i.e., these compounds have $IC_{50}$ (rat aorta) values greater than that of the known potassium channel activator, cromakalim. Therefore, in the treatment of ischemic hearts, the compounds of the instant invention are less likely to cause coronary steal, profound hypotension and coronary under-perfusion.

The preferred compounds of the present invention are those compounds of formula I where:

a, b and d are carbon atoms;
X is alkyl;
Y is a single bond or —O—;
$R^1$ is aryl or heterocyclo;
$R^2$ is —$COOR^8$, —CO-amino, —CO-substituted amino, —$NHCOCH_3$, —$NHSO_2Me$, —$NHCONH_2$, —$NH(C=NCN)NH_2$, imidazole, furan, pyridine, oxazole, hydroxy, —NHCO-substituted amino or —$SO_2Me$;

$R^3$ is hydroxy;
$R^4$ and $R^5$ are methyl;
$R^6$ is cyano, —$NO_2$, —$CF_3$, halo, alkyl or tetrazol; and
$R^7$ is hydrogen.

Compounds of formula I may be used as antiischemic agents, i.e., for the treatment of ischemic conditions such as myocardial ischemia, cerebral ischemia, lower limb ischemia and the like.

Thus a composition containing one (or a combination) of the compounds of this invention, may be administered to a species of mammal (e.g., humans) suffering from an ischemic or hypertensive condition.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the potassium channel activating activity of the compounds of this invention, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as anti-fibrillatory agents, and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, for the treatement of male impotence, as well as for the promotion of hair growth (e.g., in the treatment of male pattern baldness), and as anti-asthmatic agents.

The compounds of this invention can also be formulated in combination with a diuretic such as chlorothiazide, hydrochlorothiazide, flumethiazide, hydroflumethiazide, bendroflumethiazide, methylchlothiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the rang indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1 trans-[(6-Cyano-3,4-dihydro-3-hydroxy-2,2-dimethyl-2H- 1-benzo-pyran-4-yl)phenylamino] acetic acid, ethyl ester

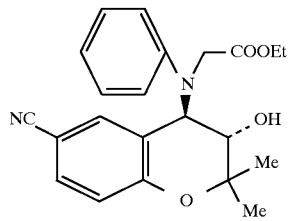

A solution of 3,4-dihydro-2,2-dimethyl-3,4-epoxy-2H-benzopyran-6-carbonitrile (400 mg, 2.0 mmol, prepared according to Evans et al., *J. Med. Chem.*, 1983, 26, 1582 and *J. Med. Chem.*, 1986, 29, 2194) and N-phenylglycine ethyl ester (700 mg, 4.0 mmol) in acetonitrile (10 mL) under argon at room temperature was treated with magnesium perchlorate (450 mg, 2.0 mmol). The mixture was stirred at 45° C. for two days; diluted with ethyl acetate and washed with 5% sodium bicarbonate, water and brine. The dried (anhydrous magnesium sulfate) organic solution was concentrated to give an oil. Flash chromatography on silica gel eluting with ethyl acetate/hexanes (1:10) gave a foam (450 mg). Trituration with hexanes gave the title product (400 mg, 53%) as a colorless solid, mp 140°–144° C. Analysis calculated for $C_{22}H_{24}N_2O_4$: C, 69.46; H, 6.36; 7.36. Found: C, 69.22; H, 6.37; N, 7.28.

EXAMPLE 2

(3S-trans)-[(6-Cyano-3,4-dihydro-3-hydroxy-2,2-dimethyl-2H-1-benzopyran-4-yl)phenylamino]acetic acid, ethyl ester

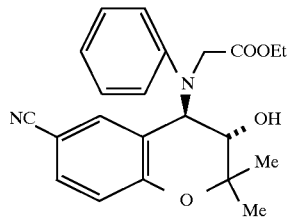

A. (1aS-cis)-1a,7b-Dihydro-2,2-dimethyl-2H-oxireno-[c][1]benzopyran-6-carbonitrile The title compound was prepared by the procedure described by Lee et. al., *Tetrahedron Letters*, 1991, 32, 5055.

B. (3S-trans)-[(6-Cyano-3,4-dihydro-3-hydroxy-2,2-dimethyl-2H-1-benzopyran-4-yl)phenylamino]acetic acid, ethyl ester The title compound was prepared from the title A compound and N-phenylglycine ethyl ester by the same procedure as described in Example 1. The product was purified by flash chromatography on silica gel eluting with ethyl acetate/hexanes (1:10) to give a foam which was triturated with hexanes to give the title compound as a colorless solid, mp 182°–183° C. Analysis calculated for $C_{22}H_{24}N_2O_4 \cdot 0.24$ $H_2O$: C, 68.69; H, 6.41; N, 7.28. Found: C, 68.57; H, 6.28; N, 7.40. $[\alpha]_D = -100.3$ (c=1.08, $CDCl_3$).

EXAMPLE 3

(3R-trans)-[(6-Cyano-3,4-dihydro-3-hydroxy-2,2-dimethyl-2H-1-benzopyran-4-yl)phenylamino]acetic acid, ethyl ester

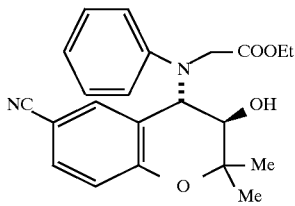

A. (1aR-cis)-1a,7b-Dihydro-2,2-dimethyl-2H-oxireno-[c][1]benzopyran-6-carbonitrile The title compound was prepared by the procedure described by Lee et. al., *Tetrahedron Letters*, 1991, 32, 5055.

B. (3R-trans)-[(6-Cyano-3,4-dihydro-3-hydroxy-2,2-dimethyl-2H-1-benzopyran-4-yl)phenylamino]acetic acid, ethyl ester The title compound was prepared from the title A compound and N-phenylglycine ethyl ester by the same procedure as described in Example 1. The product was obtained as a colorless solid, mp 182°–183° C. Analysis calculated for $C_{22}H_{24}N_2O_4 \cdot 0.37$ $H_2O$: C,68.26; H, 6.44; N, 7.24. Found: C, 67.91; H, 6.04; N, 7.59. $[\alpha]_{D=+}97.2$(c=0.88, $CDCl_3$).

EXAMPLE 4 trans-[(6-Cyano-3,4-dihydro-3-hydroxy-2,2-dimethyl-2H-1-benzo-pyran-4-yl)phenylamino] acetic acid

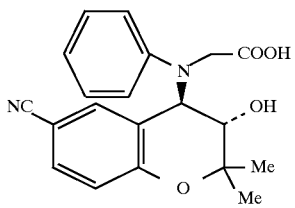

A solution of trans-[(6-cyano-3,4-dihydro-3-hydroxy-2,2-dimethyl-2H-1-benzo-pyran-4-yl)phenylamino]acetic acid, ethyl ester (310 mg, 0.81 mmol, the title compound of Example 1) in tetrahydrofuran (7 mL) and water (5 mL) at 0°–5° C. was treated with 1M lithium hydroxide (1 mL) and stirred for three hours as the temperature rose to ambient. The mixture was diluted with ethyl acetate and extracted with water (2x). The combined aqueous fractions were acidified with 10% citric acid to pH 3 and extracted with ethyl acetate. The organic fraction was washed with water and brine, dried (anhydrous magnesium sulfate) and concentrated in vacuo to give the product as a foam. Trituration with hexane containing 1–2% ether afforded the title product (230 mg) as a colorless solid, mp 163°–165° C. Analysis calculated for $C_{20}H_{20}N_2O_4 \cdot 0.11$ $H_2O$: C, 67.79; H, 5.75; N, 7.91. Found: C, 67.70; H, 5.66; N, 8.00.

EXAMPLE 5

(3R-trans)-[(6-Cyano-3,4-dihydro-3-hydroxy-2,2-dimethyl-2H-1-benzopyran-4-yl)(4-fluorophenyl)amino]acetic acid, ethyl ester

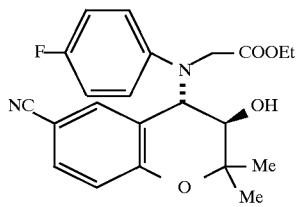

A. N-(4-Fluorophenyl)glycine ethyl ester

A solution of ethyl glyoxylate (2.47 g, 0.024 mol) in 1,2-dichloroethane (30 mL) under argon at room temperature was treated succesively with 4-fluoroaniline (1.80 g, 0.016 mol), sodium triacetoxyborohydride (5.12 g, 0.024 mol) and acetic acid (1 mL). After stirring for two hours, the mixture was concentrated, dissolved in ethyl acetate and washed 5% sodium bicarbonate, water and brine. The dried (anhydrous magnesium sulfate) organic solution was concentrated and crystallized from ether/hexanes to give the title product (2.07 g, 65%) as a colorless solid, mp 72°–73° C. Analysis calculated for $C_{10}H_{12}FNO_2 \cdot 0.07$ $H_2O$: C, 60.54; H, 6.16; N, 7.06; F, 9.58. Found: C, 60.75; H, 6.15; N, 6.96; F, 9.13.

B. (3R-trans)-[(6-Cyano-3,4-dihydro-3-hydroxy-2,2-dimethyl-2H-1-benzopyran-4-yl)(4-fluorophenyl)amino]acetic acid, ethyl ester The title compound was prepared from the title A compound and (1aR-cis)-1a,7b-dihydro-2,2-dimethyl-2H-oxireno-[c][1]benzopyran-6-carbonitrile (the title A compound of Example 3) by the same procedure as described in Example 1. The product was purified by flash chromatography on silica gel, eluting with ethyl acetate/hexanes (1:12) to give a foam which was crystallized from ethyl acetate/hexanes to provide the title compound as a colorless solid (297 mg, 37%), mp 195°–197° C. Analysis calculated for $C_{22}H_{23}FN_2O_4$: C, 66.32; H, 5.82; N, 7.03; F, 4.77. Found: C, 66.25; H, 5.78; N, 7.03; F, 4.87. $[\alpha]_D = +60.0°$ (c=0.58, $CDCl_3$).

EXAMPLE 6

(3R-trans)-[(6-Cyano-3,4-dihydro-3-hydroxy-2,2-dimethyl-2H-1-benzopyran-4-yl)(4-chlorophenyl)amino]acetic acid, ethyl ester

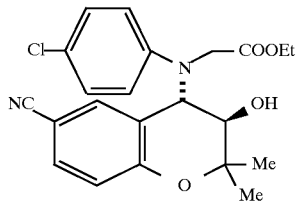

A. N-(4-Chlorophenyl)glycine ethyl ester

The title compound was prepared by the same procedure as described in Example 5, part A. The product was crystallized from ether/hexanes to give a colorless solid (1.71 g, 52%), mp 93°–95° C. Analysis calculated for $C_{10}H_{12}ClNO_2$: C, 56.21; H, 5.66; N, 6.56; Cl, 16.59. Found: C, 56.10; H, 5.65; N, 6.44; Cl, 16.78.

B. (3R-trans)-[(6-Cyano-3,4-dihydro-3-hydroxy-2,2-dimethyl-2H-1-benzopyran-4-yl)(4-chlorophenyl)amino]acetic acid, ethyl ester To a mixture of (1aR-cis)-1a,7b-dihydro-2,2-dimethyl-2H-oxireno-[c][1]benzopyran-6-carbonitrile (200 mg, 1.0 mmol, the title A compound of Example 3), N-(4-chlorophenyl)glycine ethyl ester (250 mg, 1.17 mmol, the title A compound) and magnesium perchlorate (225 mg, 1.0 mmol) under argon at room temperature was added acetonitrile (0.4 mL). The mixture was stirred at room temperature for three days. The ethyl acetate diluted solution was adsorbed onto celite and flash chromatographed on silica gel, eluting with ethyl acetate/hexanes (1:12) to give the product as a foam (210 mg). Trituration with hexanes gave the title compound (195 mg, 47%), mp 171.5°—171.5° C. Analysis calculated for $C_{22}H_{23}ClN_2O_4$: C, 63.69; H, 5.59; N, 6.75; Cl, 8.55. Found: C, 63.52; H, 5.43; N, 6.43; Cl, 8.26. $[\alpha]_D=+105.2°$ (c=0.40, $CDCl_3$).

EXAMPLE 7

(3R-trans)-[(6-Cyano-3,4-dihydro-3-hydroxy-2,2-dimethyl-2H-1-benzopyran-4-yl)phenylamino]acetamide

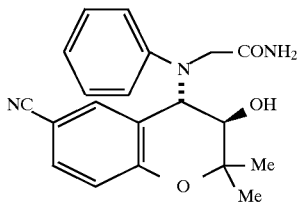

A mixture of (3R-trans)-[(6-cyano-3,4-dihydro-3-hydroxy-2,2-dimethyl-2H-1-benzopyran-4-yl)phenylaminolacetic acid, ethyl ester (310 mg, 0.81 mmol, the title compound of Example 3) in methanol (1 mL) was treated with 9.5 M methanolic ammonia (2 mL). After stirring at room temperature for 48 hours, volatiles were removed in vacuo to give a solid which was triturated with hexanes to afford title compound (286 mg, 100%) as a colorless solid, mp 236°–238° C. Analysis calculated for $C_{20}H_{21}N_3O_3 \cdot 0.22 H_2O$: C, 67.60; H, 6.08; N, 11.82. Found: C, 67.65; H, 6.05; N, 11.77. $[\alpha]_D=+90.2°$ (c=1.14, 10:1 $CDCl_3/CH_3CN$).

EXAMPLE 8

(3S-trans)-3,4-Dihydro-3-hydroxy-2,2-dimethyl-4-[(4-phenyl-2-thiazolyl)amino]-2H-1-benzopyran-6-carbonitrile

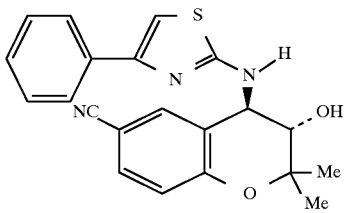

The title compound was prepared from 2-amino-4-phenylthiazole and (1aS-cis)- 1a,7b-dihydro-2,2-dimethyl-2H-oxireno-[c][1]benzopyran-6-carbonitrile (the title A compound of Example 2), by the procedure described in Example 1. The residue was purified by flash chromatography on silica gel (25% ethyl acetate in hexanes) to yield a light yellow foam which was crystallized from ether-hexanes to provide the title compound as a light yellow solid, mp 203°–204° C. Analysis calculated for $C_{21}H_{19}N_3O_2S$: C, 66.82; H, 5.07; N, 11.13; S, 8.49. Found: C, 66.83; H, 5.14; N, 10.98; S, 8.54. $[\alpha]_D=-31.4°$ (c=0.5, MeOH).

EXAMPLE 9

(3R-trans)-3,4-Dihydro-3-hydroxy-2,2-dimethyl-4-[(4-phenyl-2-thiazolyl)amino]-2H-1-benzopyran-6-carbonitrile

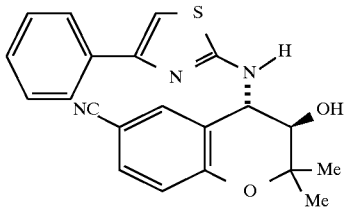

The title compound was prepared from 2-amino-4-phenylthiazole and (1aR-cis)- 1a,7b-dihydro-2,2-dimethyl-2H-oxireno-[c][1]benzopyran-6-carbonitrile (the title A compound of Example 3), by the procedure described in Example 1 to give the title compound as a light yellow solid, mp 200°–202° C. Analysis calculated for $C_{21}H_{19}N_3O\ S$: C, 66.82; H, 5.07; N, 11.13; S, 8.49. Found: C, 66.61; H, 5.12; N, 10.94; S, 8.64. $[\alpha]_D=+31.7°$ (c=0.5, MeOH).

EXAMPLE 10

(3R-trans)-[N-[3,4-Dihydro-3-hydroxy-2,2-dimethyl-6-(1H-tetrazol-5-yl)-2H-1-benzopyran-4-yl]phenylamino]acetic acid, ethyl ester

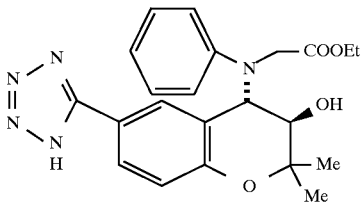

A mixture of (3R-trans)- [(6-cyano-3,4-dihydro-3-hydroxy-2,2-dimethyl-2H-1-benzopyran-4-yl)phenylamino]acetic acid, ethyl ester (420 mg, 1.1 mmol, the title compound of Example 3), sodium azide (190 mg, 3.0 mmol) and ammonium chloride (150 mg, 3.0 mmol) in dimethylformamide (1 mL) under argon was heated at 85° C. for two days. The reaction mixture was then poured into water (50 mL), extracted with ethyl acetate (3×100 mL) and washed with water (3×100 mL). After drying over anhydrous magnesium sulfate, the solvent was evaporated and the residue was purified by flash chromatography (5% methanol in dichloromethane) to give the title product (300 mg, 64%). This material was combined with another batch of the same product and rechromatographed on silica gel (5% methanol in dichloromethane). The product was recrystallized from isopropyl ether-hexanes to give (3R-trans)-[N-[3,4-dihydro-3-hydroxy-2,2-dimethyl-6-(1H-tetrazol-5-yl)-2H-1-benzopyran-4-yl]phenylamino]acetic acid, ethyl ester, mp 130°–133°. Analysis calculated for $C_{22}H_{25}N_5O_4 \cdot 0.26H_2O$: C, 61.71; H, 6.01; N, 16.35. Found: C, 61.85; H, 6.13; N, 16.21. $[\alpha_D]^{25} = +92.4°$ (c=0.392, $CDCl_3$).

EXAMPLE 11

(3R-trans)-2[N-(6-Cyano-3,4-dihydro-3-hydroxy-2,2-dimethyl-2H-1-benzopyran-4-yl)phenylamino]-N-ethylacetamide

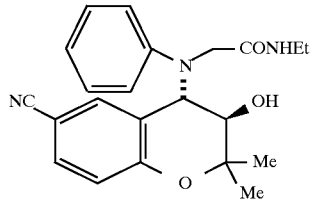

The title compound was prepared from (3R-trans)-[(6-cyano-3,4-dihydro-3-hydroxy-2,2-dimethyl-2H-1-benzopyran-4-yl)phenylamino]acetic acid, ethyl ester (the title compound of Example 3) and ethyl amine by the same procedure as described for the title compound of Example 7. The product was triturated with hexanes to give the title compound as a colorless solid, mp 213°–215° C. Analysis calculated for $C_{22}H_{25}N_3O_3$: C, 69.64; H, 6.64; N, 11.07. Found: C, 69.31; H, 6.33; N, 10.96. $[\alpha]_D=+76.6°$ (c=0.47, $CDCl_3$).

EXAMPLE 12

(3R-trans)-3,4-Dihydro-3-hydroxy-2,2-dimethyl-4-[N[2-(1-pyrrolidinyl)-2-oxoethyl]phenylamino]-2H-1-benzopyran-6-carbonitrile

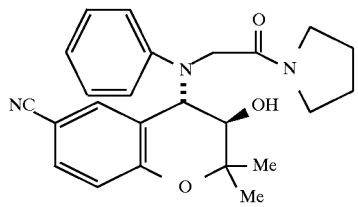

The title compound was prepared from (3R-trans)-[(6-cyano-3,4-dihydro-3-hydroxy-2,2-dimethyl-2H-1-benzopyran-4-yl)phenylamino]acetic acid, ethyl ester (the title compound of Example 3) and pyrrolidine by the same procedure as described for the title compound of Example 7. The product was triturated with hexanes to give the title compound as a colorless solid, mp 222°–224° C. Analysis calculated for $C_{24}H_{27}N_3O_3 \cdot 0.17H_2O$: C, 70.55; H, 6.75; N, 10.28. Found: C, 70.61; H, 6.76; N, 10.22. $[\alpha]_D=+45.6°$ (c=0.78, DMSO).

EXAMPLE 13

(3R-trans)-3,4-Dihydro-3-hydroxy-2,2-dimethyl-4-[N[2-(4-morpholinyl)-2-oxoethyl]phenylamino]-2H-1-benzopyran-6-carbonitrile

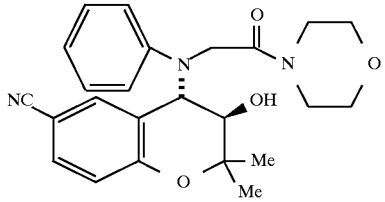

The title compound was prepared from (3R-trans)-[(6-cyano-3,4-dihydro-3-hydroxy-2,2-dimethyl-2H-1-benzopyran-4-yl)phenylamino]acetic acid, ethyl ester (the title compound of Example 3) and morpholine by the same procedure as described for the title compound of Example 7. The product was triturated with hexanes to give the title compound as a colorless solid, mp 229°–231° C. Analysis calculated for $C_{24}H_{27}N_3O_4 \cdot 0.07H_2O$: C, 68.17; H, 6.47; N, 9.94. Found: C, 68.29; H, 6.46; N, 9.82. $[\alpha]_D=+54.6°$ (c=0.71, DMSO).

EXAMPLE 14

(3R-trans)-[N-(6-Cyano-3,4-dihydro-3-hydroxy-2,2-dimethyl-2H-1-benzopyran-4-yl)phenylamino]-N-(2-furanylmethyl)acetamide

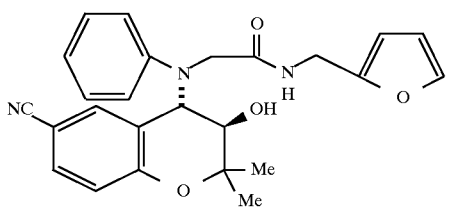

The title compound was prepared from (3R-trans)-[(6-cyano-3,4-dihydro-3-hydroxy-2,2-dimethyl-2H-1-benzopyran-4-yl)phenylamino] acetic acid, ethyl ester (the title compound of Example 3) and 2-furanylmethyl amine by the same procedure as described for the title compound of Example 7. The product was obtained as a colorless solid, mp 95°–100° C. Analysis calculated for $C_{25}H_{25}N_3O_4 \cdot 0.25H_2O$: C, 68.89; H, 5.89; N, 9.64. Found: C, 68.73; H, 5.98; N, 9.42. $[\alpha]_D=+26.5°$ (c =0.29, MeOH).

EXAMPLE 15

(3R-trans)-[N-(6-Cyano-3,4-dihydro-3-hydroxy-2,2-dimethyl-2H-1-benzopyran-4-yl)phenylamino]-N-[2-(4-morpholinyl)ethyl]acetamide

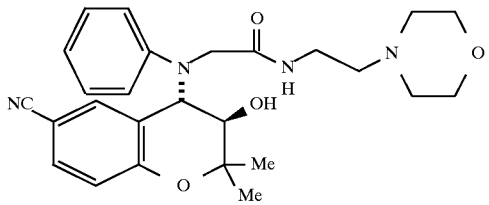

The title compound was prepared from (3R-trans)-[(6-cyano-3,4-dihydro-3-hydroxy-2,2-dimethyl-2H-

1-benzopyran-4-yl)phenylamino]acetic acid, ethyl ester (the title compound of Example 3) and 4-morpholinylethyl amnine by the same procedure as described for the title compound of Example 7. The product was obtained as a colorless solid, mp 201°–204° C. Analysis calculated for $C_{26}H_{32}N_4O_4$: C, 67.22; H, 6.94; N, 12.06. Found: C, 67.09; H, 6.88; N, 11.88. $[\alpha]_D=+23.7°$ (c=0.43, MeOH).

EXAMPLE 16

(3R-trans)-4-[(4-Fluorophenyl)(2-hydroxy-2-methylpropyl)amino]-3,4-dihydro-3-hydroxy-2,2-dimethyl-2H- 1-benzopyran-6-carbonitrile

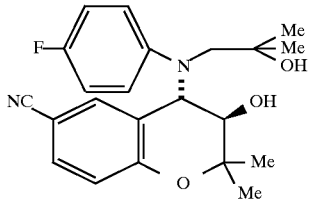

A. N-(4-Fluorophenyl)-N-(2-hydroxy-2-methylpropyl)amine

A mixture of 4-fluoroaniline (1.12 g, 10 mmol) and isobutene oxide (0.70 g, 10 mmol) was heated in a sealed tube at 120° C. overnight. The resultant oil was purified by flash chromatography to give the title compound as an oil (1.20 g, 65%).

B. (3R-trans)-4-[(4-Fluorophenyl)(2-hydroxy-2-methylpropyl)-amino]-3,4-dihydro-3-hydroxy-2,2-dimethyl-2H-1-benzopyran-6-carbonitrile The title compound was prepared from title A compound and (1aR-cis)-1a,7b-dihydro-2,2-dimethyl-2H-oxireno-[c][1] benzopyran-6-carbonitrile (the title A compound of Example 3) by the procedure described in Example 1. The product was obtained as an amorphous solid, mp 70° C. $[\alpha]_D=-62.8°$ (c=1, CHCl$_3$). Analysis calculated for $C_{22}H_{25}N_2O_3F\cdot 0.3H_2O\cdot 0.2$ toluene: C, 68.84; H, 6.71; N, 6.86. Found: C, 68.84; H, 6.72; N, 6.59.

EXAMPLE 17

[3R-[3a,4b(R*)]]-4-[(4-Fluorophenyl)(2-hydroxypropyl)amino]-3,4-dihydro-3-hydroxy-2,2-dimethyl- 2H-1-benzopyran-6-carbonitrile

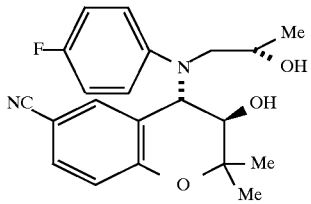

A. N-(4-Fluorophenyl)-N-(2-hydroxypropyl)amine

The title compound was prepared from 4-fluoroaniline and R-propylene oxide by the same procedure as described for the title A compound of Example 15. The product was obtained as a colorless solid.

B. [3R-[3a,4b (R*)]]-4-[(4-Fluorophenyl)(2-hydroxypropy l)-amino]-3,4-dihydro-3-hydroxy-2,2-dimethyl-2H-1-benzopyran-6-carbonitrile The title compound was prepared from title A compound and (1aR-cis)-1a,7b-dihydro-2,2-dimethyl-2H-oxireno-[c][1] benzopyran-6-carbonitrile (the title A compound of Example 3) by the procedure described for the title compound of Example 1. The product was obtained as an amorphous solid, mp 75° C. $[\alpha]_D=-64.2°$ (c=1, CHCl$_3$). Analysis calculated for $C_{21}H_{23}N_2O_3F\cdot 0.78 H_2O$: C, 65.59; H, 6.44; N, 7.29. Found: C, 65.40; H, 6.30; N, 7.48.

EXAMPLE 18

(3R-trans)-[(6-Cyano-3,4-dihydro-3-hydroxy-2,2-dimethyl-2H- 1-benzopyran-4-yl)(4-methyl-2-thiazolyl)amino]acetic acid, ethyl ester

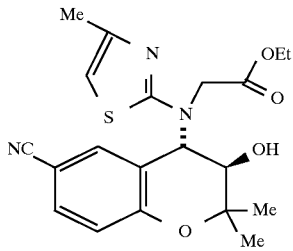

A. (3R-trans)-3,4-Dihydro-3-hydroxy-2,2-dimethyl-4-[(4-methyl-2-thiazolyl)amino]-2H-1-benzopyran-6-carbonitrile The title compound was prepared from (1aR-cis)-1a,7b-dihydro-2,2-dimethyl-2H-oxireno-[c][1]benzopyran-6-carbonitrile (the title A compound of Example 3) and 2-amino-4-methyl-thiazole by the procedure described for the title compound of Example 1. The residue was purified by a flash column to give a colorless solid (730 mg, 58%).

B. (3R-trans)-[(6-Cyano-3,4-dihydro-3-hydroxy-2,2-dimethyl-2H-1-benzopyran-4-yl)(4-methyl-2-thiazolyl)amino]acetic acid, ethyl ester A solution of title A compound (620 mg, 2.0 mmol) and ethyl bromoacetate (0.24 mL, 2.15 mmol) in dimethylformamide (4 mL) was treated with potassium carbonate (300 mg, 2.17 mmol). The resultant reaction mixture was stirred at room temperature overnight and poured into saturated sodium bicarbonate (10 mL). The aqueous solution was extracted with ethyl acetate (2×40 mL); combined organic extracts were dried over sodium sulfate, and concentrated in vacuo. The residue was purified by flash column chromatography to give an oil which solidified upon vacuum drying. The solid was washed with pentane to provide a colorless product (110 mg, 14%), mp 83° C. $[\alpha]_D=+33.2°$ (c=1, MeOH). Analysis calculated for $C_{20}H_{23}N_3SO_4\cdot 1.31 H_2O$: C, 56.51; H, 6.07; N, 9.89. Found: C, 56.81; H, 5.96; N, 9.59.

EXAMPLE 19

(3R-trans)-4-[N-(2-Benzoxazolyl)-N-(2,2-dimethoxyethyl)amino]-3,4-dihydro-3-hydroxy-2,2-dimethyl-2H-1-benzopyran-6-carbonitrile

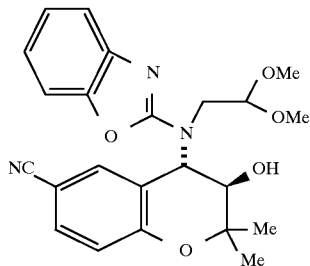

A. (3R-trans)-3,4-Dihydro-4-[(2,2-dimethoxyethyl)amino]-3-hydroxy-2,2-dimethyl-2H-1-benzopyran-6-carbonitrile A mixture of (1aR-cis)-1a,7b-dihydro-2,2-dimethyl-2H-oxireno-[c][1]benzopyran-6-carbonitrile (750 mg, 3.73 mmol, the title A compound of Example 3), dimethyl aminoacetal (1.2 mL) was heated in a sealed tube at 75° C. for two days. The reaction mixture was purified by flash column chromatography (ethyl acetate and hexane, 1:1) to give a colorless oil (1.0 g, 90%).

B. (3R-trans)-4-[N-(2-Benzoxazolyl)-N-(2,2-dimethoxyethyl)-amino]-3,4-dihydro-3-hydroxy-2,2-dimethyl-2H-1-benzopyran-6-carbonitrile To a solution of title A compound (360 mg, 1.18 mmol) in dimethylformamide (10 mL) at 0° C. under argon was added sodium hydride (60% in oil, 100 mg, 2.3 mmol). The suspension was stirred at 0° C. for 15 minutes and then treated with 2-chlorobenzoxazole (140 μL, 1.18 mmol) via a syringe. The reaction mixture was stirred at 0° C. for 30 minutes and poured into saturated ammonium chloride. The aqueous solution was extracted with ethyl acetate; the combined organic extracts were treated with acetic acid (0.5 mL) and stirred at room temperature overnight. The resultant solution was washed with sodium bicarbonate, dried over sodium sulfate and concentrated in vacuo. The residue was purified by flash column chromatography (3:1 mixture of hexane and ethyl acetate) to give an oil, which formed a foam upon vacuum drying (300 mg, 60%), mp 66° C. $[\alpha]_D$=+35.8° (c=1, MeOH). Analysis calculated for $C_{23}H_{25}N_3O_5 \cdot 0.33\ H_2O \cdot 0.40$ toluene: C, 66.46; H, 6.24; N, 9.01. Found: C, 66.47; H, 6.21; N, 8.81.

EXAMPLE 20

(3R-trans)-4-[N-[1,3-Dihydro-1,3-dioxo-2H-isoindol-2-yl)ethyl]-phenylamino]-3,4-dihydro-3-hydroxy-2,2-dimethyl-2H-1-benzopyran-6-carbonitrile

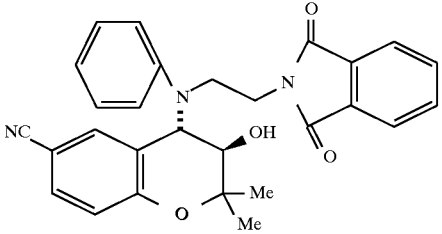

A. N-[1,3-Dihydro-1,3-dioxo-2H-isoindol-2-yl)ethyl]-N-phenylamine

A solution of N-phenylethylenediamnine (10.0 g, 73.4 mmol) and phthalic anhydride (1 1.42 g, 77.1 mmol) in toluene was heated at reflux while removing water azeotropically for 18 hours. The reaction mixture was cooled to room temperature and washed with 2.5% hydrochloric acid solution, saturated sodium bicarbonate solution and brine. The crude product solution was dried over magnesium sulfate and the solvent was r ecovere d under vacuum to provide the title product (12.03 g, 61%) as a yellow solid, mp 100°–102° C. MS: (M+NH$_4$)+@ 267.

B. (3R-trans)-4-[N-[1,3-Dihydro-1,3-dioxo-2H-isoindol-2-yl)ethyl]phenylamino]-3,4-dihydro-3-hydroxy-2,2-dimethyl-2H-1-benzopyran-6-carbonitrile The title compound was prepared from title A compound (6.62 g, 24.85 mmol) and (1aR-cis)-1a,7b-dihydro-2,2-dimethyl-2H-oxireno-[c][1]benzopyran-6-carbonitrile (5.0 g, 24.85 mmol, the title A compound of Example 3) by the procedure described for the title compound of Example 1. The crude product was purified by flash chromatography on silica gel eluting with hexane/acetone (3:1) to afford a yellow solid (7.87 g, 67%), mp 159°–160° C. $[\alpha]_D$=−110.0° (c=0.88, CHCl$_3$). Analysis calculated for $C_{28}H_{25}N_3O_4 \cdot 0.16\ H_2O$: C, 71.49; H, 5.43; N, 8.93. Found: C, 71.54; H, 5.49; N, 8.88.

EXAMPLE 21

(3R-trans)-4-[N-(2-Aminoethyl)phenylamino]-3,4-dihydro-3-hydroxy-2,2-dimethyl-2H-1-benzopyran-6-carbonitrile

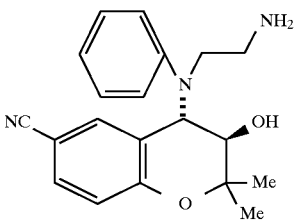

To a solution of the title compound of Example 20 (4.5 g, 10.69 mmol) in ethanol (100 mL) at room temperature was added a mixture of methyl hydrazine (50 mL) and ethanol (50 mL). The reaction was stirred at room temperature for 1.5 hours and heated at reflux for one hour. The volatiles were recovered under vacuum and the residue was partitioned between ethyl acetate and saturated sodium bicarbonate solution. The organic phase was washed with brine, dried over magnesium sulfate and evaporated in vacuo to obtain an off-white foam (3.57 g, 100%) which was crystallized from isopropyl ether/ethyl acetate to provide a colorless solid, mp 164°–165° C. $[\alpha]_D$=–20.9° (c=1.22 CHCl$_3$). Analysis calculated for $C_{20}H_{23}N_3O_2 \cdot 1.0\ H_2O \cdot 0.42$ isopropyl ether: C, 67.90; H, 7.81; N, 10.55. Found: C, 67.90; H, 7.38; N, 10.18.

EXAMPLE 22

(3R-trans)-[(6-Cyano-3,4-dihydro-3-hydroxy-2,2-dimethyl-2H- 1-benzopyran-4-yl)phenylamino] butyric acid, ethyl ester

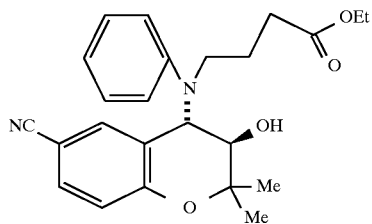

The title compound was prepared from 4-(N-phenylamino)-butyric acid (prepared according to literature methods) and (1aR-cis)-1a,7b-dihydro-2,2-dimethyl-2H-oxireno-[c][1]benzopyran-6-carbonitrile (the title A compound of Example 3) by the procedure described for the title compound of Example 1. The product was triturated with hexanes to yield an off-white solid, mp 109°–110° C. $[\alpha]_D$=+41.8° (c=0.92, MeOH). Analysis calculated for $C_{24}H_{28}N_2O_4 \cdot 0.09\ H_2O$: C, 70.28; H, 6.93; N, 6.83. Found: C, 70.31; H, 6.81; N, 6.80.

EXAMPLE 23

(3R-trans)-3-[N-(6-Cyano-3,4-dihydro-3-hydroxy-2, 2-dimethyl-2H-1-benzopyran-4-yl)phenylamino] propanoic acid, ethyl ester

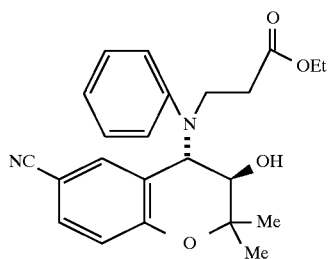

The title compound was prepared from 3-(N-phenylamino)-propanoic acid (prepared according to literature methods) and (1aR-cis)-1a,7b-dihydro-2,2-dimethyl-2H-oxireno-[c][1]benzopyran-6-carbonitrile (the title A compound of Example 3) by the procedure described for the title compound of Example 1. The product was triturated with hexanes to yield an off-white solid, mp 60°–62° C. $[\alpha]_D$=+30.4° (c=0.8, MeOH). Analysis calculated for $C_{23}H_{26}N_2O_4 \cdot 0.1\ H_2O$: C, 69.70; H, 6.66; N, 7.07. Found: C, 69.75; H, 6.74; N, 7.02.

EXAMPLE 24

(3R-trans)-3,4-Dihydro-3-hydroxy-4-[N-[(1H-imidazol-2-yl)-methyl]phenylamino]-2,2-dimethyl-2H-1-benzopyran-6-carbonitrile

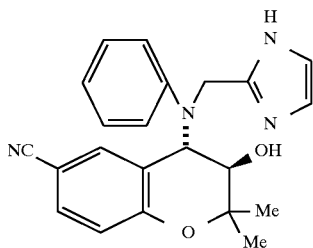

A. N-[(1H-Imidazol-2-yl)methyl]-N-phenylamine

A stirred solution of 2-imidazolecarboxaldehyde (400 mg, 4.16 mmol) in dry methanol (10 mL) was treated with aniline (380 µL, 4.16 mmol) followed by anhydrous magnesium sulfate (2 g). The solution was stirred for 18 hours at room temperature. The mixture was filtered and most of the solvent was evaporated. The solution was taken up in ethyl acetate (50 mL) and washed with 5% aqueous. KHSO$_4$ (50 mL) followed by brine (50 mL). The organic solution was dried (MgSO$_4$), filtered and solvent was removed in vacuo to give a white solid (370 mg, 52%). This material (370 mg, 2.16 mmol) in MeOH (10 mL) was treated with 10% palladium over charcoal and hydrogenated at room temperature using a balloon. The mixture was filtered through a short pad of celite and the solvent volume was removed in vacuo to give a light brown crystalline solid (350 mg, 93%). Analysis calculated for $C_{10}H_9N_3 \cdot 0.07\ H_2O$: C, 68.82; H, 6.44; N, 24.08. Found: C, 68.77; H, 6.47; N, 24.13.

B. (3R-trans)-3,4-Dihydro-3-hydroxy-4-[N-[(1H-imidazol-2-yl)-methyl]phenylamino]-2,2-dimethyl-2H-1-benzopyran-6-carbonitrile A stirred solution of (1aR-cis)-1a,7b-dihydro-2,2-dimethyl-2H-oxireno-[c][1]benzopyran-6-carbonitrile (792 mg, 3.93 mmol, the title A compound of Example 3) in acetonitrile (4 mL) was treated with the title A compound (620 mg, 3.62 mmol) followed by anhydrous COCl$_2$ (46.5 mg, 0.36 mmol). The solution was stirred for 18 hours at room temperature. Additional COCl$_2$ was added over an 18-hour period. The mixture was added to ethyl acetate (100 mL) and water (100 mL). The organic fraction was washed with brine (100 mL), dried over magnesium sulfate and the solvent was removed in vacuo to give a white solid which was purified by flash chromatography on silica gel (25% ethyl acetate in hexanes). The product was re-crystallized from chloroform-hexanes to give a colorless solid (321 mg, 24%), mp 259°–260° C. (shrinks at 140°–150° C.). $[\alpha]_D$=+16.5° (c=0.31, MeOH). Analysis calculated for $C_{22}H_{22}N_4O_2 \cdot 0.94\ H_2O$: C, 67.51; H, 6.15; N, 14.32. Found: C, 67.75; H, 5.82; N, 14.08.

EXAMPLE 25

(3R-trans)-4-[[2-(Acetylamino)ethyl]phenylamino]-3,4-dihydro-3-hydroxy-2,2-dimethyl-2H- 1-benzopyran-6-carbonitrile

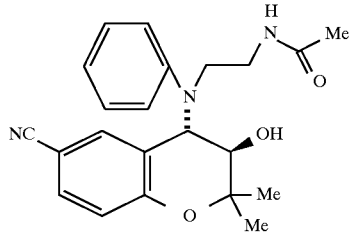

The title compound was prepared from the title compound of Example 20 by a standard procedure using acetyl chloride in pyridine and dichloromethane. The product was obtained as a colorless solid, mp 217°–218° C. $[\alpha]_D$=+54.6° (c=1.15, DMF). Analysis calculated for $C_{22}H_{25}N_3O_3 \cdot 0.21\ H_2O$: C, 68.95; H, 6.68; N, 10.97. Found: C, 69.19; H, 6.74; N, 10.73.

EXAMPLE 26

(3R-trans)-[2-[N-(6-Cyano-3,4-dihydro-3-hydroxy-2,2-dimethyl-2H-1-benzopyran-4-yl)phenylamino]ethyl]urea

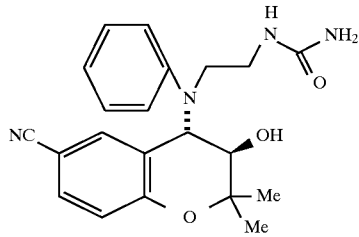

The title compound was prepared from the title compound of Example 20 by a standard procedure using trimethylsilyl-isocyanate in refluxing acetonitrile. The product was obtained as a colorless solid, mp 214°–215° C. $[\alpha]_D$=+59.2° (c=1.04, DMF). Analysis calculated for $C_{21}H_{24}N_4O_3 \cdot 0.03\ H_2O$: C, 66.20; H, 6.37; N, 14.70. Found: C, 66.10; H, 6.29; N, 14.80.

EXAMPLE 27

(3R-trans)-N-[2-[N-(6-Cyano-3,4-dihydro-3-hydroxy-2,2-dimethyl-2H-1-benzopyran-4-yl)phenylamino]ethyl]methanesulfonamide

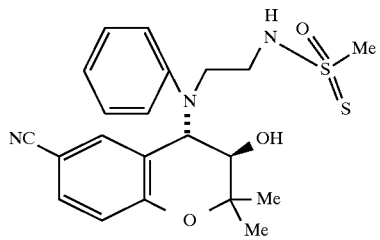

The title compound was prepared from the title compound of Example 20 by a standard procedure using methanesulfonyl chloride in pyridine and dichloromethane. The product was obtained as a colorless solid, mp 143°–145° C. $[\alpha]_D$=+33.0° (c=1.02, DMF). Analysis calculated for $C_{21}H_{25}N_3O_4S \cdot 0.67\ H_2O$: C, 59.00; H, 6.21; N, 9.83; S, 7.50. Found: C, 59.18; H, 5.80; N, 9.65; S, 7.50.

EXAMPLE 28

(3R-trans)-N"-Cyano-N-[2-[[N-(6-cyano-3,4-dihydro-3-hydroxy-2,2-dimethyl-2H-1-benzopyran-4-yl)phenylamino]ethyl]guanidine

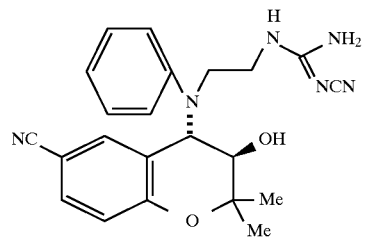

A. (3R-trans)-N'-Cyano-N-[2-[[N-(6-cyano-3,4-dihydro-3-hydroxy-2,2-dimethyl-2H-1-benzopyran-4-yl)phenylamino]ethyl]-carbamidic acid, phenyl ester A solution of (3R-trans)-4-[N-(2-aminoethyl)phenylamino]-3,4-dihydro-3-hydroxy-2,2-dimethyl-2H-1-benzopyran-6-carbonitrile (500 mg, 1.48 mmol, the title compound of Example 20) and diphenylcyano-carbonimidate (0.39 g, 1.59 mmol) in acetonitrile (5.0 mL) was heated at reflux temperature for two hours. The reaction mixture was cooled to room temperature and partitioned between ethyl acetate and 1N hydrochloric acid. The organic fraction was separated and the aqueous fraction was reextracted with ethyl acetate. The organic extracts were washed with brine, dried over magnesium sulfate and evaporated to provide the title compound as a colorless gum (0.84 g). The crude material was used for the next reaction.

B. (3R-trans)-N"-Cyano-N-[2-[[N-(6-cyano-3,4-dihydro-3-hydroxy-2,2-dimethyl-2H- 1-benzopyran-4-yl)phenylamino]-ethyl]guanidine To a solution of the title A compound (0.81 g, 1.48 mmol) in ethanol (9 mL) was added ammonium hydroxide (8.5 mL) and the reaction mixture was stirred at room temperature for 48 hours. The solvent was evaporated and the residue in ethyl acetate was washed with water and dried over anhydrous magnesium sulfate. The solvent was evaporated and the residue was purified by flash chromatography on silica gel (2% methanol in ethyl acetate). The product was triturated with isopropyl ether to give a colorless amorphous solid, mp 125°–130° C. (shrinking). $[\alpha]_D$=+31.8° (c=1.12, DMF). Analysis calculated for $C_{22}H24N_6O_2 \cdot 0.2\ H_2O \cdot 0.5$ isopropyl ether: C, 63.76; H, 6.33; N, 18.59. Found: C, 63.87; H, 6.35; N, 18.58.

EXAMPLE 29

(3R-trans)-2-[N-(6-Cyano-3,4-dihydro-3-hydroxy-2, 2-dimethyl-2H-1-benzopyran-4-yl)phenylamino]-N-(2-hydroxyethyl)acetamide

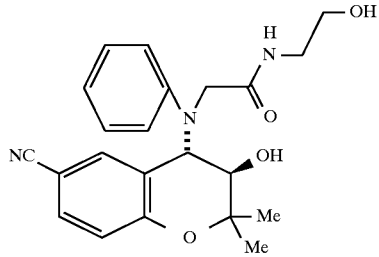

The title compound was prepared from (3R-trans)-[(6-cyano-3,4-dihydro-3-hydroxy-2,2-dimethyl-2H-1-benzopyran-4-yl)phenylamino]acetic acid, ethyl ester (the title compound of Example 3) and 2-hydroxyethyl amine by the same procedure as described for the title compound of Example 7. The product was obtained as a while foam. $[\alpha]_D=+32.7°$ (c=0.62, MeOH). Analysis calculated for $C_{22}H_{25}N_3O_4 \cdot 0.17 H_2O$: C, 66.3 1; H, 6.41; N, 10.55. Found: C, 66.29; H, 6.42; N, 10.57.

EXAMPLE 30

(3R-trans)-4-[4-Chloro-N-[(1H-imidazol-2-yl) methyl]phenylamino]-3,4-dihydro-3-hydroxy-2,2-dimethyl-2H- 1-benzopyran-6-carbonitrile

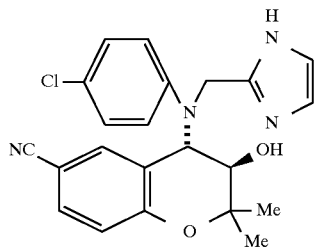

A. N-(4-Chlorophenyl)-N-[(1H-imidazol-2yl) methyl]amine

The title compound was prepared from 4-chloroaniline and 2-imidazole-carboxaldehyde by the same procedure as described in Example 24, part A. The residue was crystallized from ethyl acetate to afford the title compound (1.56 g, 72%) as an off white solid.

B. (3R-trans)-4-[4-Chloro-N-[(1H-imidazol-2-yl)-methyl]-phenylamino]-3,4-dihydro-3-hydroxy-2,2-dimethyl-2H- 1-benzopyran- -carbonitrile The title compound was prepared from (1aR-cis)-1a,7b-dihydro-2,2-dimethyl-2H-oxireno-[c][1]benzopyran-6-carbonitrile (the title A compound of Example 3) and the title A compound by the same procedure as described for the title compound of Example 24. The residue after work up was purified by column chromatography (40% ethyl acetate in hexanes) to afford the title product (198 mg, 28%) as a white solid, mp 266°–267° C. (softens at 160° C.). $[\alpha]_D=+40.8°$ (c=0.36, MeOH). Analysis calculated for $C_{22}H_{21}ClN_4O_2 \cdot 0.23H_2O$: C, 63.98; H, 5.24; N, 13.56; Cl, 8.58. Found: C, 64.37; H, 5.29; N, 13.17; Cl, 8.24.

EXAMPLE 31

(3R-trans)-4-[4-Fluoro-N-[(1H-imidazol-2-yl) methyl]phenylamino]-3,4-dihydro-3-hydroxy-2,2-dimethyl-2H-1-benzopyran-6-carbonitrile, mono hydrochloride

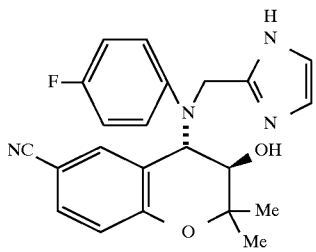

A. N-(4-Fluorophehnyl)-N- [(1H-imidazol-2yl) methyl]amine

The title compound was prepared from 4-fluoroaniline and 2-imidazole-carboxaldehyde by the same procedure as described in Example 24, part A. The product was obtained as a light yellow solid (4.84 g, 95%).

B. (3R-trans)-4-[4-Fluoro-N-[(1H-imidazol-2-yl) methyl]phenyl-amino]-3,4-dihydro-3-hydroxy-2,2-dimethyl-2H-1-benzopyran-6-carbonitrile, mono hydrochloride The title compound was prepared from (1aR-cis)-1a,7b-dihydro-2,2-dimethyl-2H-oxireno-[c][1]benzopyran-6-carbonitrile (the title A compound of Example 3) and the title A compound by the same procedure as described for the title compound of Example 24. The colorless product (643 mg, 41%) (mp 252°–253 ° C., decomposed) in methanol was converted to its hydrochloride by treatment with hydrogen chloride gas in dioxane. The solvent was removed and the residue was dissolved in water (20 mL). The solution was filtered through a Whatman 0.3 μm cellulose nitrate membrane filter and the solvent was removed by freeze drying to afford a white lyophilate. $[\alpha]_D=-23.3°$ (c=0.61, MeOH). Analysis calculated for $C_{22}H_{21}FN_4O_2 \cdot HCl \cdot 1.39H_2O$: C, 58.35; H, 5.29; N, 12.37; Cl, 7.83; F, 3.79. Found: C, 58.76; H, 5.12; N, 11.96; Cl, 7.51; F, 4.20.

EXAMPLE 32

(3R-trans)-4-[N-(3-Furanylmethyl)phenylamino]-3, 4-dihydro-3-hydroxy-2,2-dimethyl-2H-1-benzopyran-6-carbonitrile

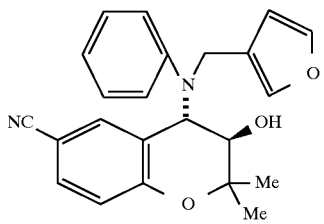

A. [N-(3-Furanylmethyl)-N-phenylamine

A mixture of aniline (1.89 g, 19.6 mmol) and 3-furaldehyde (2.50 g, 26.8 mmol) in 1,2-dichloroethane (100 mL) under argon at 5° was treated with sodium triacetoxyborohydride (5.65 g, 26.8 mmol) and acetic acid (1.5 mL). The reaction mixture was stirred at room temperature overnight, concentrated in vacuo and the residue was diluted with ethyl acetate. The combined extracts were washed with satuirated sodium bicarbonate, dried over $MgSO_4$ and concentrated. The product was purified by flash chromatography on silical gel (Hexane/EtOAc (20:1) to yield the title compound (3.31 g, 98%). Analysis calculated for $C_{11}H_{11}NO$: C, 76.28; H, 6.40; N, 8.09. Found: C, 76.58; H, 6.46; N, 8.33.

B. (3R-trans)-4-[N-(3-Furanylmethyl)phenylamino]-3,4-dihydro-3-hydroxy-2,2-dimethyl-2H-1-benzopyran-6-carbonitrile The title compound was prepared from (1aR-cis)-1a,7b-dihydro-2,2-dimethyl-2H-oxireno-[c][1]benzopyran-6-carbonitrile (the title A compound of Example 3) and the title A compound by the same procedure as described for the title compound of Example 1. The product was obtained as a colorless solid (0.85 g, 57%), mp 63°–67° C. $[\alpha]_D=+65.2°$ (c=0.71 MeOH). Analysis calculated for $C_{23}H_{22}N_2O_3 \cdot 0.25H_2O$: C, 72.90; H, 5.98; N, 7.39. Found: C, 72.94; H, 5.95; N, 7.35.

EXAMPLE 33

(3R-trans)-4-[N-(2-Furanylmethyl)phenylamino]-3,4-dihydro-3-hydroxy-2,2-dimethyl-2H-1-benzopyran-6-carbonitrile

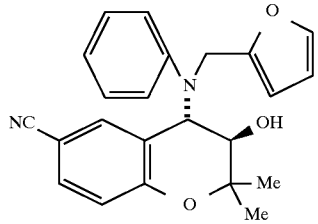

A. [N-(2-Furanylmethyl)-N-phenylamine

The title compound was prepared from aniline and 2-furaldehyde by the same procedure as described in Example 32, part A. The product was obtained as an oil (3.43 g, 99%).

B. (3R-trans)-4-[N-(2-Furanylmethyl)phenylamino]-3,4-dihydro-3-hydroxy-2,2-dimethyl-2H-1-benzopyran-6-carbonitrile The title compound was prepared from (1aR-cis)-1a,7b-dihydro-2,2-dimethyl-2H-oxireno-[c][1]benzopyran-6-carbonitrile (the title A compound of Example 3) and the title A compound by the same procedure as described for the title compound of Example 1. The product was obtained as a colorless solid (1.07 g, 72%), mp 134°–135° C. $[\alpha]_D=+92.20°$ (c=0.78, MeOH). Analysis calculated for $C_{23}H_{22}N_2O_3 \cdot 0.02 H_2O$: C, 73.70; H, 5.93; N, 7.47. Found: C, 73.65; H, 5.63; N, 7.52.

EXAMPLE 34

(3R-trans)-4-[N-[(4,5-Dihydro-2-oxazolyl)methyl]phenylamino]-3,4-dihydro-3-hydroxy-2,2-dimethyl-2H-1-benzopyran-6-carbonitrile

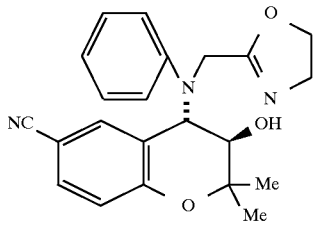

A stirred solution of (3R-trans)-2[N-(6-cyano-3,4-dihydro-3-hydroxy-2,2-dimethyl-2H-1-benzopyran-4-yl)phenylamino]-N-(2-hydroxyethyl)-acetamide (600 mg, 1.52 mmol, the title compound of Example 29) in dichloromethane (3 mL) at 0° C. under argon was treated with triethylamine (254 μL, 1.82 mmol) and methanesulfonyl chloride (130 μL 1.67 mmol). The solution was stirred for 30 minutes at −30° C. and warmed to room temperature. It was diluted with ethyl acetate and washed with water, sodium bisulfite and brine (100 mL). After drying over anhydrous magnesium sulfate, the solvent was removed. The oily residue in dimethylformamide (5 mL) was treated with finely ground potassium carbonate and heated at 150° C. for 30 minutes. The reaction mixture was further stirred for two days at room temperature and diluted with ethyl acetate. It was washed with water, 5% sodium bisulfite and brine (100 mL). After drying over anhydrous magnesium sulfate, the solvent was removed and the residue was purified by flash chromatography on silica gel (40% ethyl acetate in hexanes). The resulting solid was recrystallized from chloroform-hexanes to give the title product (490 mg, 85%) as fine white needles, mp 218°–220° C. $[\alpha]_D=+71.8°$ (c=0.4, MeOH). Analysis calculated for $C_{22}H_{23}N_3O_3$: C, 70.00; H, 6.14; N, 11.13. Found: C, 69.96; H, 6.09; N, 11.17.

EXAMPLE 35

(3R-trans)-[(2-Benzoxazolyl)(6-cyano-3,4-dihydro-3-hydroxy-2,2-dimethyl-2H-1-benzopyran-4yl)amino]acetic acid, ethyl ester

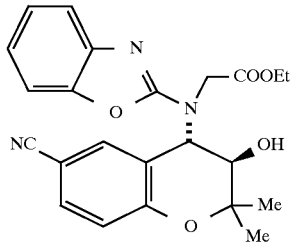

A. (3R-trans)-4-Amino-3,4-dihydro-3-hydroxy-2,2-dimethyl-2H-1-benzopyran-6-carbonitrile To a solution of (1aR-cis)-1a,7b-dihydro-2,2-dimethyl-2H-oxireno-[c][1]benzopyran-6-carbonitrile ((2.5 g, 12.4 mmol, the title A compound of Example 3) in tetrahydrofuran in a re-sealable tube was added concentrated ammonium hydroxide (2 mL). The tube was sealed and the solution was heated on an oil bath at 75° C. overnight. The resultant solution was cooled to room temperature, concentrated and extracted with ethyl acetate. The combined organic extracts were dried over anhydrous sodium sulfate and concentrated to yield the title compound as an oil.

B. (3R-trans)-[(6-Cyano-3,4-dihydro-3-hydroxy-2,2-dimethyl-2H-1-benzopyran-4yl)amino]acetic acid, ethyl ester To a solution of (3R-trans)-4-amino-3,4-dihydro-3-hydroxy-2,2-dimethyl-2H-1-benzopyran-6-carbonitrile (the title A compound) and ethyl glyoxylate (2.5 g) in methanol (30 mL) and acetic acid (2 mL) at 0° C. under argon atmosphere was added sodium cyanoborohydride (1.5 g). The reaction mixture was stirred at 0 C. for 30 minutes, poured into saturated sodium bicarbonate (150 mL) and extracted with ethyl acetate. The combined organic extracts were dried over anhydrous sodium sulfate and concentrated. The residue was purified by chromatography to give an oil, which solidified upon standing (1.8 g, 48%).

C. (3R-trans)-[(2-Benzoxazolyl)(6-cyano-3,4-dihydro-3-hydroxy-2,2-dimethyl-2H-1-benzopyran-4yl)amino]acetic acid, ethyl ester The title compound was prepared from the title B compound and 2-chlorobenzoxazole by the same procedure as described in Example 19, part B. The product was purified by flash chromatography on silica gel (4:1 mixture of hexane and ethyl acetate) to give the title compound as an amorphous solid (320 mg, 46%), mp ~90° C. $[\alpha]_D$=+44.30° (c=1, MeOH). Analysis calculated for $C_{23}H_{25}N_3O_5 \cdot 0.32H_2O$: C, 64.66; H, 5.58 N, 9.83. Found: C, 64.72; H, 5.45; N, 9.77.

EXAMPLE 36

(3R-trans)-4-[(2-Benzoxazolyl)(2-pyridinylethyl)amino]-3,4-dihydro-3-hydroxy-2,2-dimethyl-2H-1-benzopyran-6-carbonitrile

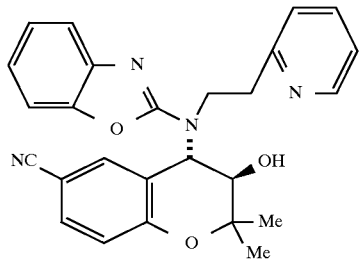

A. (3R-trans)-4-[(2-Pyridinylethyl)amino]-3,4-dihydro-3-hydroxy-2,2-dimethyl-2H-1-benzopyran-6-carbonitrile A solution of (1aR-cis)-1a,7b-dihydro-2,2-dimethyl-2H-oxireno-[c][1]benzopyran-6-carbonitrile ((1.0 g, 5.0 mmol, the title A compound of Example 3) and 2-aminoethylpyridine (1.1 g, 9.0 mmol) was heated in a sealed tube at 75° C. for 18 hours. The reaction mixture was cooled to room temperature and purified by flash chromatography to afford an oil, which solidified upon standing (1.4 g, 87%).

B. (3R-trans)-4-[(2-Benzoxazolyl)(2-pyridinylethyl)amino]-3,4-dihydro-3-hydroxy-2,2-dimethyl-2H-1-benzopyran-6-carbonitrile The title compound was prepared from the title A compound and 2-chlorobenzoxazole by the same procedure as described in Example 19, part B. The product was purified by flash chromatography on silica gel (4:1 mixture of hexane and ethyl acetate) to give the title compound as a foam (550 mg, 94%). $[\alpha]_D$=+33.2° (c=1, MeOH). Analysis calculated for $C_{26}H_{24}N_4O_3 \cdot 0.93H_2O$: C, 68.29; H, 5.70; N, 12.25. Found: C, 68.64; H, 5.68; N, 11.90.

EXAMPLE 37

(3R-trans)-4-[(2-Benzoxazolyl)(2-furanomethyl)amino]-3,4-dihydro-3-hydroxy-2,2-dimethyl-2H-1-benzopyran-6-carbonitrile

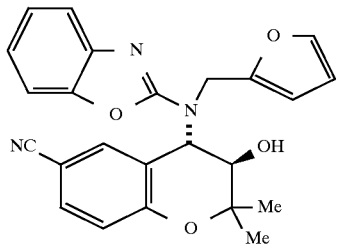

A. (3R-trans)-4-[(2-Furanomethyl)amino]-3,4-dihydro-3-hydroxy-2,2-dimethyl-2H-1-benzopyran-6-carbonitrile The title compound was prepared from (1aR-cis)-1a,7b-dihydro-2,2-dimethyl-2H-oxireno-[c][1]benzopyran-6-carbonitrile (the title A compound of Example 3) and 2-furfurylanine by the same procedure as described in Example 36, part A. The product was obtained as a colorless oil (1.35 g, 91%).

B. (3R-trans)-4-[(2-Benzoxazolyl)(2-furanomethyl)amino]-3,4-dihydro-3-hydroxy-2,2-dimethyl-2H-1-benzopyran-6-carbonitrile The title compound was prepared from the title A compound and 2-chlorobenzoxazole by the same procedure as described in Example 19, part B. The oily product became a foam upon vacuum drying. $[\alpha]_D$=+64.4° (c=1, MeOH). Analysis calculated for $C_{24}H_{21}N_3O \cdot 0.40 \, H_2O \cdot 0.2$ toluene: C, 69.17; H, 5.35; N, 9.53. Found: C, 69.10, H, 5.25; N, 9.43.

EXAMPLE 38

(3R-trans)-4-[(2-Furanylmethyl)(2-oxazolyl)amino]-3,4-dihydro-3-hydroxy-2,2-dimethyl-2H-1-benzopyran-6-carbonitrile

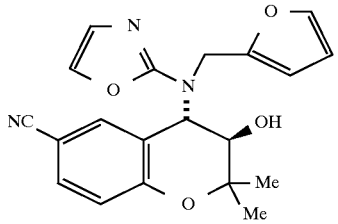

A. (2,2-Dimethoxyethyl)carbamic acid, 4-nitrophenyl ester

A solution of dimethyaminoacetal (1.1 g, 10 mmol), and triethyl amine (1.4 mL, 11 mmol) in a mixture of ether (100 mL) and methylene chloride (5 mL) at 0° C. in an ice-bath was treated with 4-nitrophenyl chloroformate (2.2 g, 11 mmol). The solution was slowly warmed up to room temperature and stirred at room temperature for two hours. The reaction mixture was poured into 5% hydrochloric solution (20 mL), the organic layer was separated and dried over anhydrous magnesium sulfate. The solvent was removed to give the title product as a solid, which was used for the next step without further purification.

B. (3R-trans)-N-(6-Cyano-3,4-dihydro-3-hydroxy-2,2-dimethyl-2H-1-benzopyran-4-yl)-N'-(2,2-dimethoxyethyl)-N-(2furanylmethyl)urea To a solution of (3R-trans)-4-[(2-furanomethyl)amino]-3,4-dihydro-3-hydroxy-2,2-dimethyl-2H-1-benzopyran-6-carbonitrile (1.1 g, 3.69 mmol, the title A compound of Example 37) in acetonitrile (5 mL) was added the title A compound (1.3 g, 4.9 mmol) followed by diisopropylethyl amine (0.85 mL). The mixture was heated at reflux temperature over night, concentrated in vacuo and the residue was diluted with ethyl acetate (100 mL). The resulting solution was washed with 10% aqueous potassium hydroxide, saturated ammonium chloride and dried over magnesium sulfate. The solvent was removed and the residue was purified by flash chromatography to provide the title compound as a colorless solid. Analysis calculated for $C_{22}H_{27}N_3O_6 \cdot 0.21$ toluene: C, 62.87; H, 6.45; N, 9.34. Found: C, 62.86; H, 6.58; N, 9.56.

C. [S-(R*,R*)]-N-(2-Furanylmethyl)-N-(2-hydroxy-1-methyl-propyl)-N'-(2-oxoethyl)urea The solution of the title B compound in acetone (5 mL) was treated with 10% hydrochloride (1 mL). The mixture was stirred at room temperature for three hours and neutralized with sodium bicarbonate (3 mL). The mixture was concentrated in vacuo and the residue was extracted with ethyl acetate (2×100 mL). The organic extracts were dried over anhydrous magnesium sulfate and concentrated. The residue was purified by flash column (3:2/ethyl acetate:hexane) to give an oil (720 mg, 51% from the title A compound).

D. (3R-trans)-4-[(2-Furanylmethyl)(2-oxazolyl)amino]-3,4-dihydro-3-hydroxy-2,2-dimethyl-2H-1-benzopyran-6-carbonitrile To a solution of the title C compound (700 mg, 1.83 mmol) in methylene chloride (50 mL) under argon at room temperature was added triphenylphosphine (1.0 g, 3.83 mmol), diisopropylethyl amine (1.4 mL, 7.7 mmol) and iodine (1.0 g, 3.85 mmol). The brown reaction mixture was stirred at room temperature for an hour and poured into saturated sodiumthiosulfate solution (25 mL). The organic layer was separated, dried over anhydrous magnesium and the solvent was removed. The residue was purified by flash chromatography to give the title compound as a colorless foam (260 mg, 39%), mp 63° C. $[\alpha]_D$=+51.7° (c=1.0, MeOH). Analysis calculated for $C_{20}H_{19}N_3O_4 \cdot 0.15$ ether•0.4 $H_2O$: C, 64.42; H, 5.55; N, 10.94. Found: C, 64.78; H, 5.36; N, 11.15.

EXAMPLE 39

(3R-trans)-4-[N-(Cyanomethyl)phenylamino]-3,4-dihydro-3-hydroxy-2,2-dimethyl-2H-1-benzopyran-6-carbonitrile

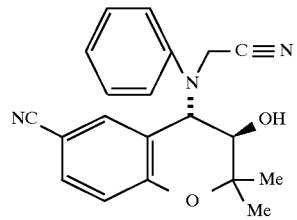

The title compound was prepared from N-phenylglycinonitrile and (1aR-cis)-1a,7b-dihydro-2,2-dimethyl-2H-oxireno-[c][1]benzopyran-6-carbonitrile (the title A compound of Example 3) by the procedure described for the title compound of Example 1. The product was triturated with hexanes (containing 1% ethyl acetate) to give a colorless solid, mp 85°–90° C. $[\alpha]_D$=+120.9° (c=0.45, $CDCl_3$). Analysis calculated for $C_{20}H_{19}N_3O_2 \cdot 0.27$ $H_2O \cdot 0.04$ hexanes: C, 71.15; H, 5.93; N, 12.30. Found: C, 71.16; H, 5.81; N, 11.87.

EXAMPLE 40

(3R-trans)-4-[N-(Cyanoethyl)phenylamino]-3,4-dihydro-3-hydroxy-2,2-dimethyl-2H-1-benzopyran-6-carbonitrile

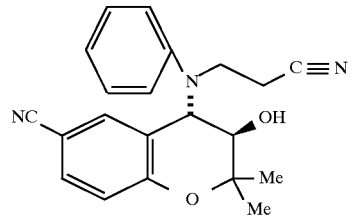

The title compound was prepared from anilinopropionitrile and (1aR-cis)-1a,7b-dihydro-2,2-dimethyl-2H-oxireno-[c][1]benzopyran-6-carbonitrile (the title A compound of Example 3) by the procedure described for the title compound of Example 1. The product was triturated with hexanes (containing 1% ethyl acetate) to give a colorless solid, mp 164–166C. $[\alpha]_D$=−38.1° (c=1.0, $CDCl_3$). Analysis calculated for $C_{21}H_{21}N_3O_2 \cdot 0.14$ $H_2O$: C, 72.09; H, 6.13; N, 12.02. Found: C, 71.91; H, 5.83; N, 11.92.

EXAMPLE 41

(3R-trans)-3,4-Dihydro-3-hydroxy-4-[N-(2-methoxyethyl) phenyl-amino]-2,2-dimethyl-2H-1-benzopyran-6-carbonitrile

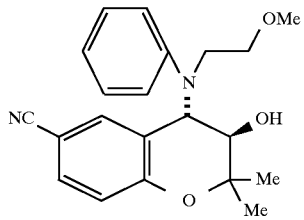

A. N-(2-methoxyethyl)aniline

The title compound was prepared from aniline and methoxyacetaldehyde by the same method as described for Example 5, part A. The residue was purified by flash chromatography on silica gel (ethyl acetate:hexanes/1:15) to give a pale yellow oil.

B. (3R-trans)-3,4-Dihydro-3-hydroxy-4-[N-(2-methoxyethyl)-phenyl-amino]-2,2-dimethyl-2H-1-benzopyran-6-carbonitrile The title compound was prepared from the title A compound and (1aR-cis)-1a,7b-dihydro-2,2-dimethyl-2H-oxireno-[c][1]benzopyran-6-carbonitrile (the title A compound of Example 3) by the procedure described for the title compound of Example 1. The oily residue was purified by flash chromatography on silica gel (ethyl acetate:hexanes/1:6), to give a colorless powder (410 mg, 77%), mp 119°–124° C. $[\alpha]_D$=+54.40 (c=0.43, MeOH). Analysis calculated for $C_{21}H_{24}N_2O_3$: C, 71.57; H, 6.86; N, 7.95. Found: C, 71.53; H, 6.94; N, 7.73.

EXAMPLE 42

(3R-cis)-[N-(6-Cyano-3,4-dihydro-3-hydroxy-2,2-dimethyl-2H-1-benzopyran-4-yl)phenylaniino]-N-ethyl-acetamide

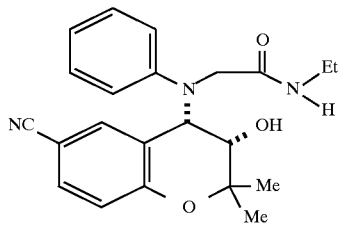

A. (4aR-cis)-1,2,3,4a,5,10b-Hexahydro-5,5-dimethyl-3-oxo-1-phenyl[1]benzopyrano[3,4-b][1,4]oxazine-9-carbonitrile A solution of N-phenylglycine ethyl ester (900 mg, 5.0 mmol) in 1,2-dichloroethane (10 mL) under argon at 20° C. was treated with trimethylaluminum (3.0 mL, 2.0M in toluene, 6.0 mmol) over 1–2 minutes. After 15 minutes, (1aR-cis)-1a,7b-dihydro-2,2-dimethyl-2H-oxireno[c][1]benzopyran-6-carbonitrile (1.0 g, 5.0 mmol, title A compound of example 3) was added at once and stirring was continued for 1.5 hours. The mixture was diluted with ethyl acetate, quenched with a few drops of water and filtered through celite to remove gelatinous aluminum salts. The filtrate was washed with 5% sodium bicarbonate, water and brine, dried over anhydrous magnesium sulfate and concentrated. The residue was triturated with warm methanol to give warm methanol to give the title product (392 mg), mp 241°–243° C. $[\alpha]_D$=−129.1° (c=0.35 CHCl$_3$). Analysis calculated for. $C_{20}H_{18}N_2O_3 \cdot 0.14$ H$_2$O: C,71.29; H,5.47; N, 8.31. Found: C, 71.05; H, 5.30; N, 8.55.

B. (3R-cis)-2-[N-(6-Cyano-3,4-dihydro-3-hydroxy-2,2-dimethyl-2H-1-benzopyran-4-yl)phenylamino]-N-ethyl-acetamide A slurry of title A compound (150 mg, 0.45 mmol) in ethanol/chloroform (10 mL, 10:1) was treated with 70% aqueous ethylamine (160 mg, 2.5 mmol), the mixture gradually becoming homogeneous over 0.5 hour. After 2 hours, the solution was concentrated and the residue crystallized from ethyl acetate/hexane (1:10) to give the title product (150 mg, 87%), mp 202°–204° C. $[\alpha]_D$=+132.3° (c=0.52 CHCl$_3$). Analysis calculated for $C_{22}H_{25}N_3O_3$: C, 69.64; H, 6.64; N, 11.07. Found: C, 69.32; H, 6.39; N, 10.67.

Compounds of Examples 43 to 106 and 112 to 118 may be prepared by modifying the procedures described in Examples 1 to 42 and 107 to 111 as known by those skilled in the art.

EXAMPLE 43

(3R-trans)-3,4-Dihydro-3-hydroxy-2,2-dimethyl-4-[N-[(5-methyl-3isoxazolyl)methyl]phenylamino]-2H-1-benzopyran-6-carbonitrile

| M. P. °C. (solvent) | Rotation $[\alpha]_D$° | Anaylsis |
|---|---|---|
| 80–90 (foam) | +36.9 (MeOH) | Calculated for $C_{23}H_{23}N_3O_3$. 0.1 H$_2$O: C, 70.60; H, 5.97; N, 10.74. Found: C, 70.49; H, 5.58; N, 10.43. |

EXAMPLE 44

(3R-trans)-4-[(4-Fluorophenyl)[(5 -methyl-3-isoxazolyl)methyl]-aminol-3,4-dihydro-3-hydroxy-2, 2-dimethyl -2H-1-benzopyran- 6-carbonitrile

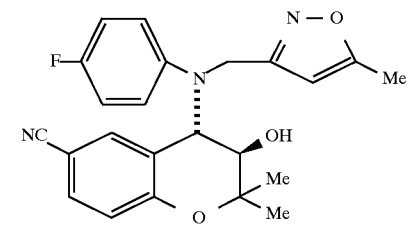

| M. P. °C. (solvent) | Rotation [α]<sub>D</sub>° | Analysis |
|---|---|---|
| 80–90 (foam) | +12.7 (MeOH) | Calculated for $C_{23}H_{22}FN_3O_3$: C, 67.80; H, 5.44; N, 10.31; F, 4.66. Found: C, 67.84; H, 5.65; M, 10.00; F, 4.57. |

EXAMPLE 45

(3S-cis)-2-[N-(6-Cyano-3,4-dihydro-3-hydroxy-2, 2dimethyl-2H-1-benzopyran-4-yi)phenylaminol-N-ethyl-acetamide

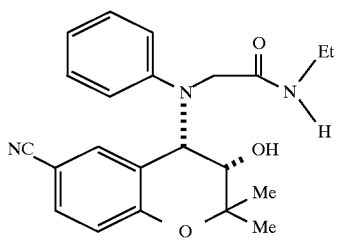

| M. P. °C. (solvent) | Rotation [α]<sub>D</sub>° | Analysis |
|---|---|---|
| 204–206 (EtOAc/Hexanes) | −132.5 (CDCl<sub>3</sub>) | Calculated for $C_{22}H_{25}N_3O_3$: C, 69.64; H, 6.64; N, 11.07. Found: C, 69.42; H, 6.14; N, 10.73. |

EXAMPLE 46

(3R-trans)-[[[5-[[(3,4-Dihydro-3-hydroxy-2,2-dimethyl-2H- 1-benzopyran-4-yl)(4-fluorophenyl) amino]methyl]-2-furanyl]methyl]-amino]acetic acid, ethyl ester, monohydrochloride

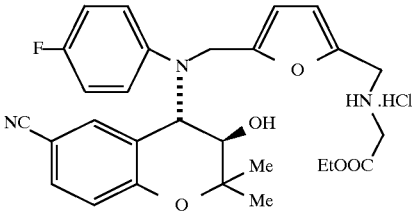

| M. P. °C. (solvent) | Rotation [α]<sub>D</sub>° | Analysis |
|---|---|---|
| 105–115 (Et<sub>2</sub>O/Hexanes) | −6.1 (CDCl<sub>3</sub>) | Calculated for $C_{28}H_{30}FN_3O_5$. 1.0 HCl: C, 61.82; H, 5.74; N, 7.72; Cl, 6.52. Found: C, 61.72; H, 5.70; M, 7.47; Cl, 6.09. |

EXAMPLE 47

(3R-trans)-4-[(4-Fluorophenyl)[[5-(hydroxymethyl)-2-furanyl]-methyl]amino]-3,4-dihydro-3-hydroxy-2, 2-dimethyl-2H- 1-benzopyran-6-carbonitrile

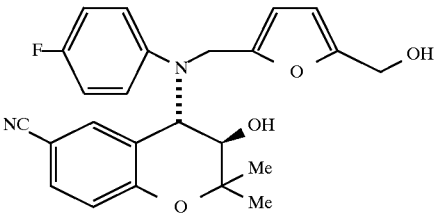

| M. P. °C. (solvent) | Rotation [α]<sub>D</sub>° | Analysis |
|---|---|---|
| 63–68 (Hexanes) | +50.7 (MeOH) | Calculated for $C_{24}H_{23}FN_2O_4$: C, 66.99; H, 5.59; N, 6.51; F, 4.42. Found: C, 67.22; H, 5.81; N, 6.28; Cl, 4.46. |

EXAMPLE 48

(3R-trans)-[(6-Cyano-3,4-dihydro-3hydroxy-2,2-dimethyl-2H-1-benzopyran-4-yl)phenylamino]acetic acid, n-butyl ester

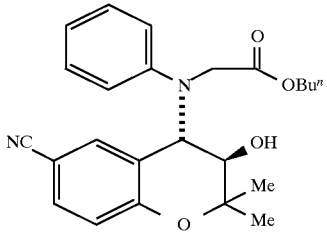

| M. P. °C. (solvent) | Rotation [α]$_D$° | Analysis |
|---|---|---|
| 82–85 (foam) | +80.3 (CDCl$_3$) | Calculated for C$_{24}$H$_{28}$N$_2$O$_4$: C, 70.57; H, 6.91; N, 6.86. Found: C, 70.50; H, 7.06; N, 6.84. |

EXAMPLE 49

(3R-trans)-[N-(6-Cyano-3,4-dihydro-3-hydroxy-2,2-dimethyl-2H-1-benzopyran-4-yl)phenylamino]-N-phenylacetamide

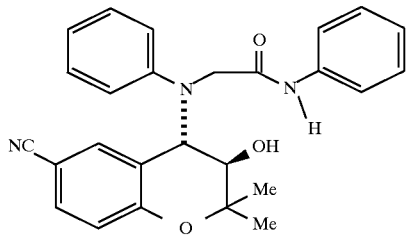

| M. P. °C. (solvent) | Rotation [α]$_D$° | Analysis |
|---|---|---|
| 135–145 (hexnes) | −21.7 (MeOH) | Calculated for C$_{26}$H$_{25}$N$_3$O$_3$.0.23H$_2$0.0.06 hexanes C, 72.48; H, 6.07; N, 9.62. Found: C, 72.48; H, 6.03; N, 9.17. |

EXAMPLE 50

(3R-trans)-4-[N-(2-Furanylmethyl)phenylamino]-3,4-dihydro-2,2-dimethyl-6-(1H-tetrazol-5-yl)-2H-1-benzopyran-3-ol

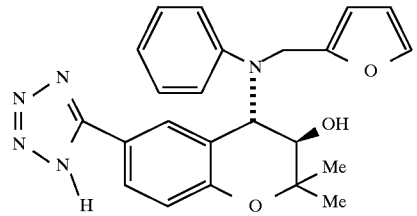

| M. P. °C. (solvent) | Rotation [α]$_D$° | Analysis |
|---|---|---|
| 130–135 (Hexanes) | +35.9 (MeOH) | Calculated for C$_{23}$H$_{23}$N$_5$O$_3$: C, 66.17; H, 5.55; N, 16.78. Found: C, 65.87; H, 5.88; N, 16.81. |

EXAMPLE 51

(3R-trans)-3,4Dihydro-3-hydroxy-2,2-dimethyl-4-[N-[(5-methyl-3-isoxazolyl)methyl]phenylamino]-2H-1-benzopyran-6-carbonitrile

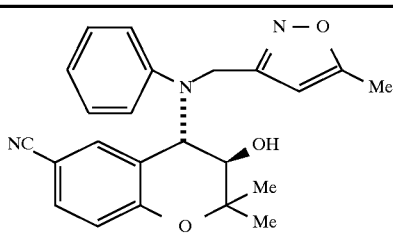

| M. P. °C. (solvent) | Rotation [α]$_D$° | Analysis |
|---|---|---|
| 80–90 | +36.9 (MeOH) | Calculated for C$_{23}$H$_{23}$N$_3$O$_3$: C, 70.60; H, 5.97; N, 10.74. Found: C, 70.49; H, 5.58; N, 10.43. |

EXAMPLE 52

(3S-trans)-3,4Dihydro-3-hydroxy-4-[N-[(1H-imidazol-2-yl)methyl]-phenylamino]-2,2-dimethyl-2H-1-benzopyran-6-carbonitrile

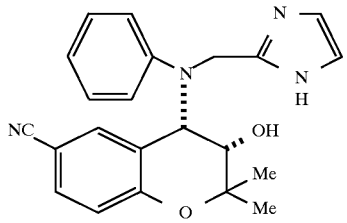

| M.P. °C. (solvent) | Rotation $[\alpha]_D°$ | Anaylsis |
|---|---|---|
| 264–265 (decomposition) | −23.9 (MeOH) | Calcualted for $C_{22}H_{22}N_4O_2 \cdot 0.61H_2O$:<br>C, 68.55; H, 6.07; N, 14.54.<br>Found: C, 68.66; H, 5.99; N, 14.43. |

EXAMPLE 53

(3R-trans)-3,4Dihydro-3-hydroxy-2,2-dimethyl-4-[N-(2-oxazolylmethyl)phenylamino]-2H-1-benzopyran-6-carbonitrile

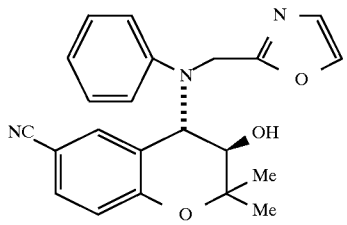

| M. P. °C. (solvent) | Rotation $[\alpha]_D°$ | Analysis |
|---|---|---|
| 207–208 | +48.8 (CHCl$_3$) | Calculated for $C_{22}H_{21}N_3O_3 \cdot 1.00H_2O \cdot 0.14EtOAc$: C, 68.78; H, 5.99; N, 10.36.<br>Found: C, 67.12; H, 5.58; N, 9.92. |

EXAMPLE 54

(3R-trans)-2[[N-(6-Cyano-3,4-dihydro-3-hydroxy-2,2-dimethyl-2H-1-benzopyran-4-yl)phenylamino]methyl]-4-oxazolecarboxylic acidethyl ester

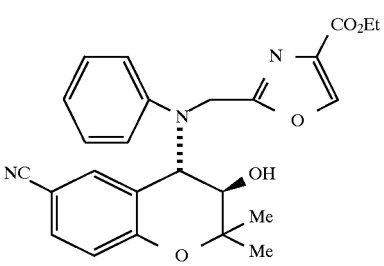

| M. P. °C. (solvent) | Rotation $[\alpha]_D°$ | Analysis |
|---|---|---|
| 99–100 | +16.1 (CHCl$_3$) | Calculated for $C_{25}H_{25}N_3O_5$:<br>C, 67.10; H, 5.63; N, 9.39.<br>Found: C, 67.21; H, 5.43; N, 9.22. |

EXAMPLE 55

(3R-trans)-2[[N-(6-Cyano-3,4-dihydro-3-hydroxy-2,2-dimethyl-2H-1-benzopyran-4-yl)phenylamino]methyl]-4-oxozolecarboxylic acid mono sodium salt

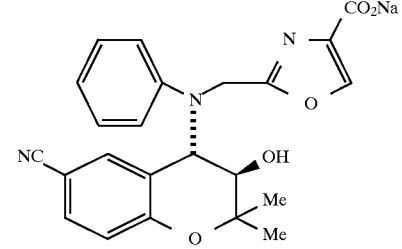

| M. P. °C. (solvent) | Rotation $[\alpha]_D°$ | Analysis |
|---|---|---|
| 203–204 | +33.3 (MeOH) | Calculated for $C_{23}H_{20}NaN_3O_5 \cdot 0.84H_2O$:<br>C, 60.50; H, 4.79; N, 9.20.<br>Found: C, 60.67; H, 4.41; N, 9.03. |

EXAMPLE 56

(S*,R*)-N-[[N-(6-Cyano-3,4-dihydro-3-hydroxy-2,2-dimethyl-2H-1-benzopyran-4-yl)phenylamino]acetyl]-L-serine, methyl ester

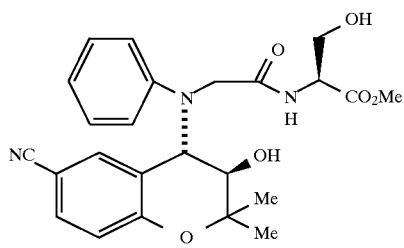

| M. P. °C. (solvent) | Rotation [α]$_D$° | Analysis |
|---|---|---|
| 105–108 | +75.6 (CHCl$_3$) | Calculated for C$_{24}$H$_{27}$N$_3$O$_6$: C, 63.55; H, 6.00; N, 9.27. Found: C, 63.25; H, 6.08; N, 9.15. |

EXAMPLE 57

(3R-trans)-4-[N-[(5-Methyl-1,3,4-oxadiazol-2-yl)methyl]phenylamino]-3,4-dihydro-3-hydroxy-2,2-dimethyl-2H-1-benzopyran-6-carbonitrile

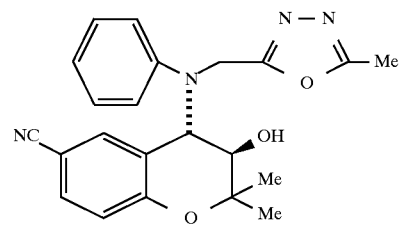

| M. P. 0° C. (solvent) | Rotation [α]$_D$° | Analysis |
|---|---|---|
| 201–202 | +2.1 (CHCl$_3$) | Calculated for C$_{22}$H$_{22}$N$_4$O$_3$.0.13H$_2$O: C, 67.28; H, 5.71; N, 14.27. Found: C, 67.41; H, 5.80; N, 14.14. |

EXAMPLE 58

(3R-trans)-4-[(4-Chlorophenyl)(2-oxazolylmethyl)amino]-3,4-dihydro-3-hydroxy-2,2-dimethyl-2H-1-benzopyran-6-carbonitrile

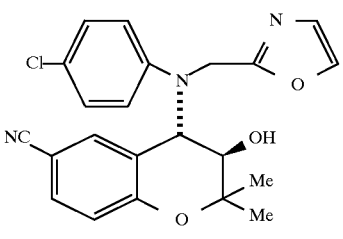

| M. P. 0° C. (solvent) | Rotation [α]$_D$° | Analysis |
|---|---|---|
| 149–150 | +66.1 (MeOH) | Calculated for C$_{22}$H$_{20}$ClN$_3$O$_3$.0.43H$_2$O: C, 63.26; H, 5.04; N, 10.06. Found: C, 63.58; H, 4.71; N, 9.74. |

EXAMPLE 59

(3R-trans)-4-[N-(1H-Benzimidazol-2-ylmethyl)phenylamino]3,4-dihydro-3-hydroxy-2,2-dimethyl-2H-1-benzopyran-6-carbonitrile

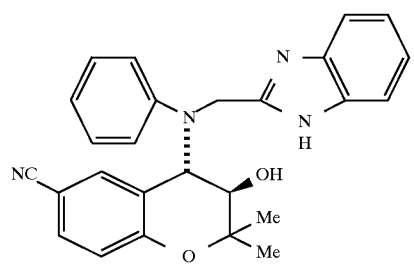

| M. P. 0° C. (solvent) | Rotation [α]$_D$° | Analysis |
|---|---|---|
| 246–247 (decomp) | −57.7 (CHCl$_3$) | Calculated for C$_{26}$H$_{24}$N$_4$O$_2$: C, 73.57; H, 5.70; N, 13.20. Found: C, 73.52; H, 5.81; N, 12.80. |

EXAMPLE 60

(3R-trans)-4-[(2-Benzoxazolyl)[2-(4-morpholinyl)ethyl]amino]-3,4-dihydro-3-hydroxy-2,2-dimethyl-2H-1-benzopyran-6-carbonitrile

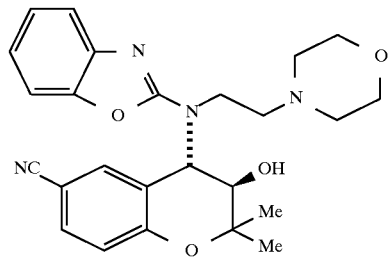

| M. P. 0° C. (solvent) | Rotation [α]$_D$° | Analysis |
|---|---|---|
| 110–115 | +50.2 (MeOH) | Calculated for $C_{25}H_{28}N_4O_4$. 1.15 $H_2O$: C, 63.99; H, 6.51; N, 11.94. Found: C, 63.98; H, 6.15; N, 11.92. |

EXAMPLE 61

(3R-trans)-4-[(2-Furanylmethyl)(2-pyrimidinyl)amino]-3,4dihydro-3-hydroxy-2,2-dimethyl-2H-1-benzopyran-6-carbonitrile

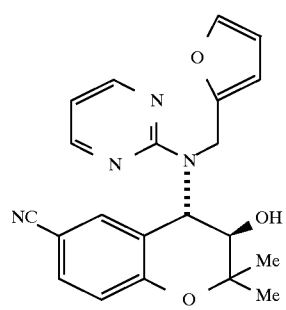

| M. P. 0° C. (solvent) | Rotation [α]$_D$° | Analysis |
|---|---|---|
| 65–75 | +76.8 (MeOH) | Calculated for $C_{21}H_{20}N_4O_3$. 0.85$H_2O$: C, 64.39; H, 5.58; N, 14.30. Found: C, 64.04; H, 5.17; N, 13.97. |

EXAMPLE 62

(3R-trans)-3,4Dihydro-3-hydroxy-2,2-dimethyl-4-[(2-pyrazinyl)-(3-pyridinylmethyl)amino]-2H-1-benzopyran-6-carbonitrile

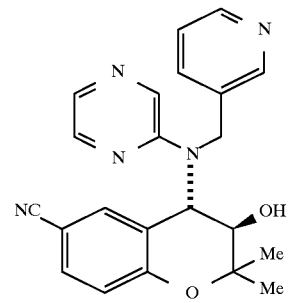

| M. P. °C. (solvent) | Rotation [α]$_D$° | Analysis |
|---|---|---|
| 110–112 | −9.8 (MeOH) | Calculated for $C_{22}H_{21}N_5O_2$. 0.38$H_2O$.1.42TFA: C, 53.64; H, 4.20; N, 12.59; F, 14.55. Found: C, 53.45; H, 3.79; N, 12.23; F, 14.17. |

EXAMPLE 63

(3R-trans)-3,4Dihydro-3-hydroxy-2,2-dimethyl-4-[(3-pyridinylmethyl)(2-pyrimidinyl)amino]-2H-1-benzopyran-6-carbonitrile

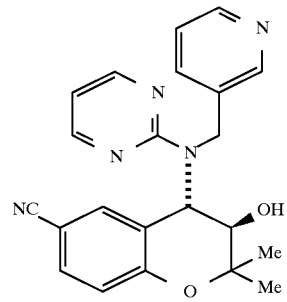

| M. P. °C. (solvent) | Rotation [α]$_D$° | Analysis |
|---|---|---|
| 102–105 | +6 (MeOH) | Calculated for $C_{22}H_{21}N_5O_2$. 0.5$H_2O$.1.65TFA: C, 51.98; H, 4.08; N, 11.98; F, 16.09. Found: C, 51.62; H, 3.71; N, 11.78; F, 15.85. |

EXAMPLE 64

(3R-trans)-4-[(2-Benzoxazolyl)(2-pyridinylmethyl)amino]-3,4-dihydro-3-hydroxy-2,2-dimethyl-2H-1-benzopyran-6-carbonitrile

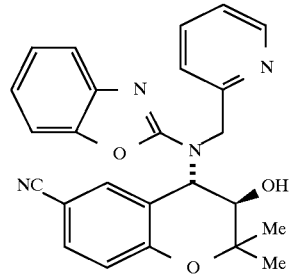

| M.P. °C. (solvent) | Rotation [α]$_D$° | Analysis |
|---|---|---|
| 122–124 | +49.6 (MeOH) | Calculated for C$_{25}$H$_{23}$N$_4$O$_3$·0.3C$_4$H$_{10}$O·0.2H$_2$O: C, 69.51; H, 5.61; N, 12.38. Found: C, 69.13; H, 5.27; N, 12.35. |

EXAMPLE 65

(3R-trans)-3,4-Dihydro-3-hydroxy-2,2-dimethyl-4-[(2-pyrimidinyl)(2-pyridinylmethyl)amino]-2H-1-benzopyran-6-carbonitrile

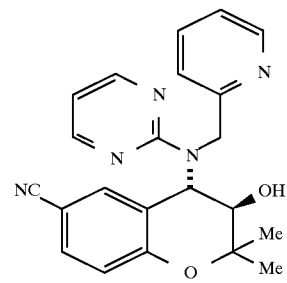

| M.P. °C. (solvent) | Rotation [α]$_D$° | Analysis |
|---|---|---|
| 227–228 | −61.5 (CHCl$_3$) | Calculated for C$_{22}$H$_{21}$N$_5$O$_2$·0.35H$_2$O: C, 67.12; H, 5.55; N, 17.79. Found: C, 67.19; H, 5.25; N, 17.72. |

EXAMPLE 66

(3R-trans)-4-[(4-Fluorophenyl)(2-pyridinylmethyl)amino]-3,4-dihydro-3-hydroxy-2,2-dimethyl-2H-1-benzopyran-6-carbonitrile

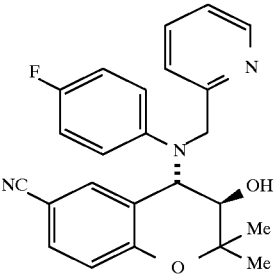

| M.P. °C. (solvent) | Rotation [α]$_D$° | Analysis |
|---|---|---|
| 182–184 | −56.2 (MeOH) | Calculated for C$_{24}$H$_{22}$N$_3$O$_2$F·0.2H$_2$O: C, 70.82; H, 5.55; N, 10.32; F, 4.67. Found: C, 70.73; H, 5.42; N, 10.32; F, 4.52. |

EXAMPLE 67

4-[4-Fluoro-N-(1H-imidazol-2-ylmethyl)phenylamino]-3,4-dihydro-2,2-dimethyl-2H-1-benzopyran-6-carbonitrile

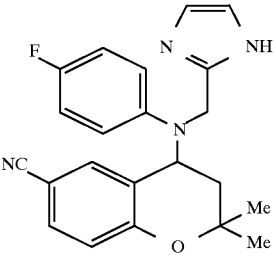

| M.P. °C. (solvent) | Rotation [α]$_D$° | Analysis |
|---|---|---|
| 122–124 | | Calculated for C$_{22}$H$_{21}$N$_5$OF·0.1C$_4$H$_6$D·0.95H$_2$O: C, 67.10; H, 6.01; N, 13.97; F, 4.75. Found: C, 67.45; H, 6.10; N, 13.55; F, 4.85. |

EXAMPLE 68

(3R-trans)-4-[(4-Fluorophenyl)(2-pyrimidinyl)amino]-3,4dihydro-3-hydroxy-2,2-dimethyl-2H-1-benzopyran-6-carbonitrile, monohydrochloride

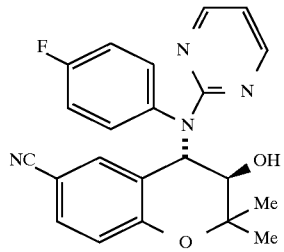

| M.P. °C. (solvent) | Rotation $[\alpha]_D°$ | Analysis |
|---|---|---|
| 182–184 | −37.2 (CD$_3$OD) | Caculated for $C_{22}H_{19}N_4O_2F$. 0.85HCl.0.7H$_2$O: C, 60.88; H, 4.93; N, 12.91; Cl, 6.94; F, 4.38. Found: C, 61.25; H, 4.82; N, 12.47; Cl, 6.75; F, 3.93. |

EXAMPLE 69

(3R-trans)-4-[(2-Furanylmethyl)(2-pyrazinyl)amino]-3,4-dihydro-3-hydroxy-2,2-dimethyl-2H-1-benzopyran-6-carbonitrile

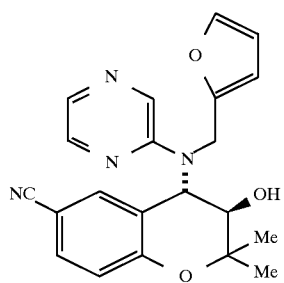

| M.P. °C. (solvent) | Rotation $[\alpha]_D°$ | Analysis |
|---|---|---|
| 88–90 | +100.8 (MeOH) | Calculated for $C_{21}H_{20}N_4O_3$. 0.6H$_2$O.0.4TFA: C, 60.49; H, 5.03: N, 12.94; F, 5.27. Found: C, 60.51; H, 4.92; N, 12.75; F, 5.41. |

EXAMPLE 70

(3R-trans) -4-[(2-Benzothiazolyl)(3-pyridinylmethyl)amino]-3,4-dihydro-3-hydroxy-2,2-dimethyl-2H-1-benzopyran-6-carbonitrile

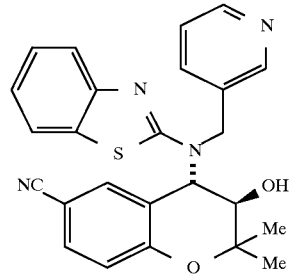

| M.P. °C. (solvent) | Rotation $[\alpha]_D°$ | Analysis |
|---|---|---|
| 134 | | Calculated for $C_{25}H_{22}N_4O_2S$. 0.5H$_2$O.0.25C$_4$H$_{10}$O: C, 66.43; H, 5.47; N, 11.92; S, 6.82. Found: C, 66.39; H, 5.20; N, 11.72; S, 6.89. |

EXAMPLE 71

(3R-trans)-4-[(4-Fluorophenyl)(3-pyridinylmethyl)amino]-3,4-dihydro-3-hydroxy-2,2-dimethyl-2H-1-benzopyran-6-carbonitrile

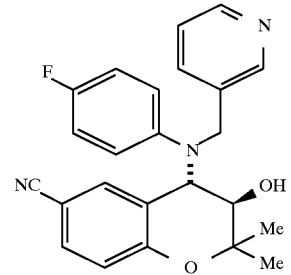

| M.P. °C. (solvent) | Rotation $[\alpha]_D°$ | Analysis |
|---|---|---|
| 184–185 | −55.0 (MeOH) | Calcualted for $C_{24}H_{22}N_3O_2F$. 0.2CHCl$_3$: C, 68.02; H, 5.24; N, 9.82; F, 4.45. Found: C, 68.12; H, 5.14; N, 9.48; F, 4.66. |

EXAMPLE 72

(3R-trans)-4-[(2-Benzothiazolyl)(3-pyridinylmethyl)amino]-3,4-dihydro-3-hydroxy-2,2dimethyl-2H-1-benzopyran-6-carbonitrile, 1-oxide

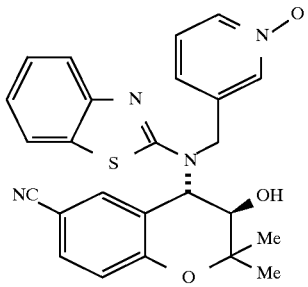

| M.P. °C. (solvent) | Rotation [α]$_D$° | Analysis |
|---|---|---|
| 195–202 | | Calculated for C$_{25}$H$_{22}$N$_4$SO$_3$. 0.76H$_2$O: C, 63.59; H, 5.02; N, 11.87; S, 6.79. Found: C, 63.89; H, 4.86; N, 11.57; S, 6.22. |

EXAMPLE 73

(3R-trans)-4-[(4-Chlorophenyl)[2-(4-morpholinyl)ethyl]amino]-3,4-dihydro-3-hydroxy-2,2-dimethyl-2H-1-benzopyran-6-carbonitrile, monohydrochloride

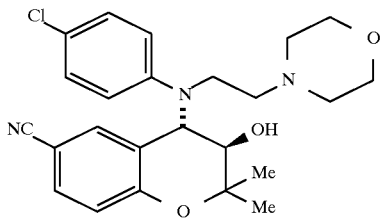

| M.P. °C. (solvent) | Rotation [α]$_D$° | Analysis |
|---|---|---|
| 165–170 | −30.4 (MeOH) | Calculated for C$_{24}$H$_{28}$N$_3$O$_3$Cl. 0.84C$_4$H$_{10}$O.1.0HCl: C, 60.78; H, 6.97; N, 7.77; Cl, 13.11. Found: C, 60.63; H, 6.57; N, 7.32; Cl, 12.95. |

EXAMPLE 74

(3R-trans)-4-[(4-Fluorophenyl)[2-(4-morpholinyl)ethyl]amino]-3,4-dihydro-3-hydroxy-2,2-dimethyl-2H-1-benzopyran-6-carbonitrile, monohydrochloride

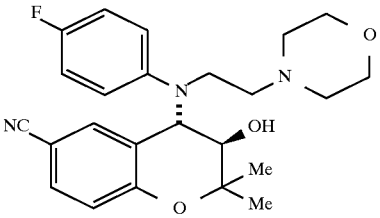

| M.P. °C. (solvent) | Rotation [α]$_D$° | Analysis |
|---|---|---|
| 170–175 | −36.5 (MeOH) | Calculated for C$_{24}$H$_{28}$N$_3$O$_3$F.0.55H$_2$O. 0.15C$_4$H$_{10}$O.1.1HCl: C, 60.71; H, 6.57; N, 8.64; F, 3.90; Cl, 8.01. Found: C, 60.75; H, 6.47; N, 8.47; F, 3.59; Cl, 7.94. |

EXAMPLE 75

(3R-trans)-4-[(6-Chloro-3-pyridazinyl)[2-(4-morpholinyl)ethyl]-amino]-3,4-dihydro-3-hydroxy-2,2-dimethyl-2H-1-benzopyran-6-carbonitrile, hydrochloride

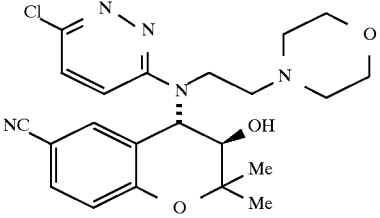

| M.P. °C. (solvent) | Rotation [α]$_D$° | Analysis |
|---|---|---|
| >200 | +9.5 (MeOH) | Calculated for C$_{22}$H$_{26}$N$_5$O$_3$Cl. 1.45HCl.0.29H$_2$O: C, 52.69; H, 5.54; N, 13.96; Cl, 17.32. Found: C, 52.93; H, 5.30; N, 13.72; Cl, 17.32. |

EXAMPLE 76

(3R-trans)-4-[(2-Benzothiazolyl)(1H-imidazol-2-ylmethyl)amino]-3,4-dihydro-3-hydroxy-2,2dimethyl-2H-1-benzopyran-6-carbonitrile, monohydrochloride

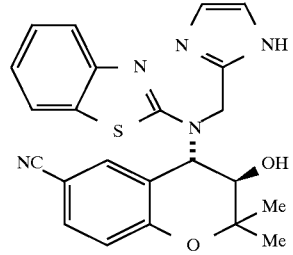

| M.P. °C. (solvent) | Rotation $[\alpha]_D°$ | Analysis |
|---|---|---|
| >200 | −17.5 (MeOH) | Calculated for $C_{23}H_{21}N_5O_2S.1.36HCl.0.56H_2O$: C, 56.24; H, 4.82; N, 14.26; Cl, 9.82; S, 653. Found: C, 56.62; H, 4.46; N, 13.88; Cl, 9.83; S, 6.47. |

EXAMPLE 77

(3R-trans)-4-[(6-Chloro-3-pyridazinyl)(1H-imidazol-2-ylmethyl)-amino]-3,4-dihydro-3-hydroxy-2,2-dimethyl-2H-1-benzopyran-6-carbonitrile, monohydrochloride

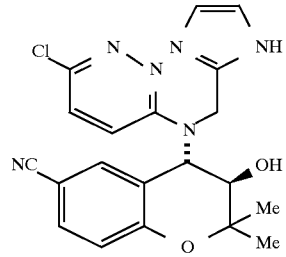

| M.P. °C. (solvent) | Rotation $[\alpha]_D°$ | Analysis |
|---|---|---|
| 210 | −1.9 (MeOH) | Calculated for $C_{20}H_{19}N_6O_2Cl.HCl.0.64H_2O$: C, 52.36; H, 4.67; N, 18.32; Cl, 15.46. Found: C, 52.60; H, 4.39; N, 18.08; Cl, 15.60. |

EXAMPLE 78

(3R-trans)-4-[(5-Trifluoromethyl-2-pyridinyl))(1H-imidazol-2-ylmeth yl)amino]-3,4-dihydro-3-hydroxy-2,2-dimethyl-2H-1-benzopyran-6-carbonitrile, monohydrochloride

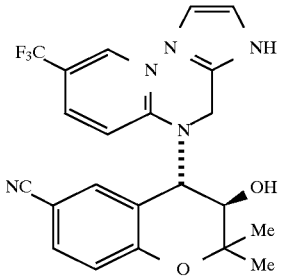

| M. P. °C. (solvent) | Rotation $[\alpha]_D°$ | Analysis |
|---|---|---|
| 180 | +2.5 (MeOH) | Calculated for $C_{22}H_{20}N_5O_2F_3.1.15HCl.0.5C_4H_{10}O$: C, 55.17; H, 5.05; N, 13.41; Cl, 7.80; F, 10.91. Found: C, 55.03; H, 4.27; N, 13.11; Cl, 7.60; F, 10.99. |

EXAMPLE 79

(3R-trans)-3,4Dihydro-3-hydroxy-2,2-dimethyl-4-[[2-(4-morpholinyl)ethyl](4-phenyl-2-thiazolyl)amino]-2H-1-benzopyran-6-carbonitrile, monohydrochloride

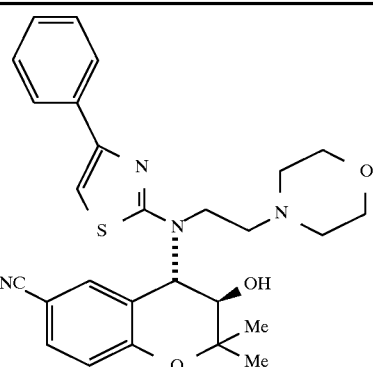

| M. P. °C. (solvent) | Rotation $[\alpha]_D°$ | Analysis |
|---|---|---|
| 170 | −22 (MeOH) | Calculated for $C_{27}H_{30}N_4O_3S.1.35HCl.H_2O$: C, 58.13; H, 6.03; N, 10.04; Cl, 8.58; S, 5.75. Found: C, 58.38; H, 5.37; N, 9.60; Cl, 8.68; S, 6.19. |

EXAMPLE 80

(3R-trans)-3,4Dihydro-3-hydroxy-4-[(1H-imidazol-2-yl-methyl) (4-phenyl-2-thiazolyl)amino]-2,2-dimethyl-2H-1-benzopyran-6-carbonitrile

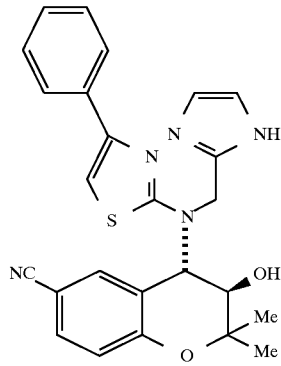

| M. P. °C. (solvent) | Rotatiom $[\alpha]_D°$ | Analysis |
|---|---|---|
| 160–170 | +16.0 (MeOH) | Calculated for $C_{25}H_{23}N_5O_2S.0.2H_2O.$ $0.1C_4H_8O_2$: C, 64.91; H, 5.19; N, 14.91; S, 6.82. Found: C, 65.23; H, 5.14; N, 14.49; S, 7.61. |

EXAMPLE 81

(3R-trans)-3,4-Dihydro-3-hydroxy-4-[(1H-imidazol-2-yl-methyl)-(4-methyl-2-thiazolyl)amino]-2,2-dimethyl-2H-1-benzopyran-6-carbonitrile

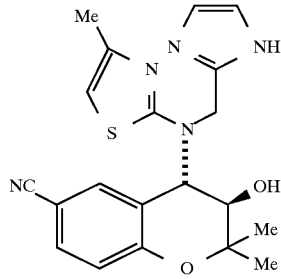

| M. P. °C. (solvent) | Rotation $[\alpha]_D°$ | Analysis |
|---|---|---|
| 178–183 | +7.4 (MeOH) | Calculated for $C_{20}H_{21}N_5O_2S.0.15H_2O.$ $0.17C_4H_8O_2$: C, 60.12; H, 5.53; N, 16.95; S, 7.76. Found: C, 60.10; H, 5.37; N, 16.59; S, 7.75. |

EXAMPLE 82

(3R-trans)-N-[2-[N-(6-Cyano-3,4-dihydro-3-hydroxy-2,2-dimethyl-2H-1-benzopyran-4-yl)phenylamino]ethyl]-2,2-dimethyl-propanamide

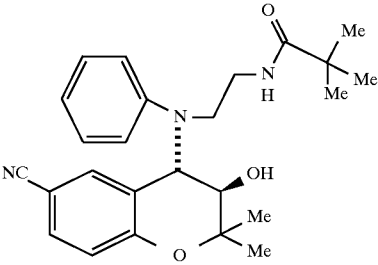

| M. P. °C. (solvent) | Rotation $[\alpha]_D°$ | Analysis |
|---|---|---|
| 194–195 (hexanes) | +61.1 (DMF) | Calculated for $C_{25}H_{31}N_3O_2.0.15H_2O$: C, 70.78; H, 7.44; N, 9.91. Found: C, 70.89; H, 7.42; N, 9.80. |

EXAMPLE 83

(3R-trans)-N-[2-[N-(6-Cyano-3,4-dihydro-3-hydroxy-2,2-dimethyl-2H-1-benzopyran-4-yl)phenylamino]ethyl]-N'-phenylurea

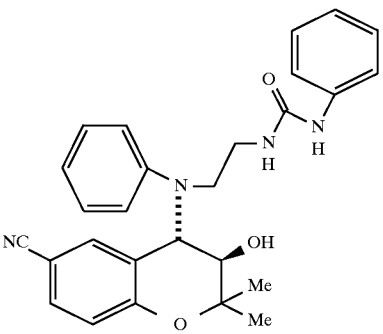

| M. P. °C. (solvent) | Rotation $[\alpha]_D°$ | Analysis |
|---|---|---|
| 193–195 | +32.3 (DMF) | Calculated for $C_{27}H_{26}N_4O_3.0.34H_2O$: C, 70.10; H, 6.25; N, 12.11. Found: C, 69.72; H, 6.07; N, 11.79. |

EXAMPLE 84

(3R-trans)-N-[2-[N-(6-Cyano-3,4-dihydro-3-hydroxy-2,2-dimethyl-2H-1-benzopyran-4-yl)phenylamino]ethyl]-1-pyrrolidinecarboxamide

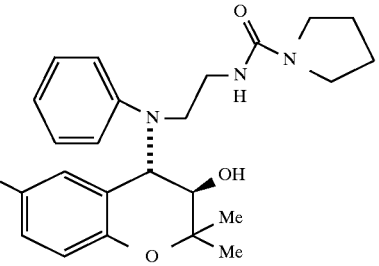

| M. P. °C. (solvent) | Rotation $[\alpha]_D°$ | Analysis |
|---|---|---|
| 125–135 | +35.8 (DMF) | Calculated for $C_{25}H_{30}N_4O_3 \cdot 0.38H_2O$: C, 68.03; H, 7.02; N, 12.69. Found: C, 68.13; H, 7.05; N, 12.21. |

EXAMPLE 85

(3R-trans)-3,4-Dihydro-3-hydroxy-2,2-dimethyl-4-[N-[(2-oxo-1-pyrrolidinyl)ethyl)phenyl]amino]-2H-1-benzopyran-6-carbonitrile

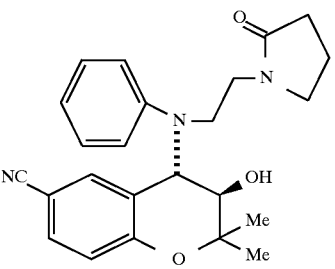

| M. P. °C. (solvent) | Rotation $[\alpha]_D°$ | Analysis |
|---|---|---|
| 214–216 | +14.4 (DMF) | Calculated for $C_{24}H_{27}N_3O_3 \cdot 0.18H_2O$: C, 70.53; H, 6.75; N, 10.28. Found: C, 70.57; H, 6.57; N, 10.24. |

EXAMPLE 86

(3R-trans)-[[(6-Cyano-3,4-dihydro-3-hydroxy-2,2-dimethyl-2H-1-benzopyran-4-yl)(4-fluorophenyl)amino]methyl]phosphonic acid, diethyl ester

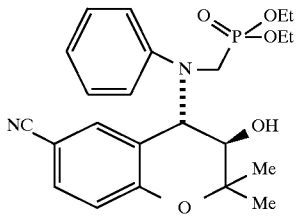

| M. P. °C. (solvent) | Rotation $[\alpha]_D°$ | Analysis |
|---|---|---|
| 55–56 | +7.2 (MeOH) | Calculated for $C_{23}H_{28}N_2FPO_5 \cdot 0.27H_2O$: C, 59.12; H, 6.16; N, 5.99; F, 4.07; P, 6.63. Found: C, 59.23; H, 6.15; N, 5.88; F, 3.86; P. 6.43. |

EXAMPLE 87

[N-(4-Clorophenyl)-N-(6-cyano-3,4-dihydro-2,2-dimethyl-2H-1-benzopyran-4-yl)amino]acetic acid, ethyl ester

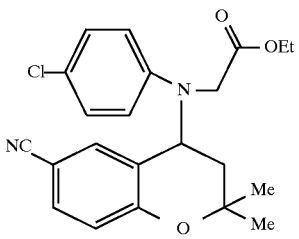

| M. P. °C. (solvent) | Rotation $[\alpha]_D°$ | Analysis |
|---|---|---|
| 55–57 | | Calculated for $C_{22}H_{23}N_2ClO_3 \cdot 0.02CHCl_3$: C, 65.32; H, 5.83; N, 6.92; Cl, 9.28. Found: C, 65.38; H, 5.79; N, 6.90; Cl, 9.49. |

EXAMPLE 88

4-[(4-Clorophenyl)(1H-imidazol-2-ylmethyl)amino]-3,4-dihydro-2,2-dimethyl-2H-1-benzopyran-6carbonitrile

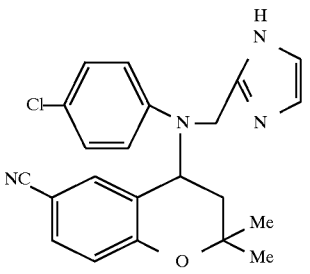

| M. P. °C. (solvent) | Rotation [α]$_D$° | Analysis |
|---|---|---|
| 212–214 | | Calculated for $C_{22}H_{21}N_4ClO \cdot 0.42H_2O$: C, 66.16; H, 5.26; N, 14.03. Found: C, 66.42; 5.33; N, 13.77. |

EXAMPLE 89

(3R-trans)-3,4-Dihydro-3-hydroxy-2,2-dimethyl-4-[N-[(3-methyl-1,2,4-oxadiazol-5-yl)methyl]phenylamino]-2H-1-benzopyran-6-carbonitrile

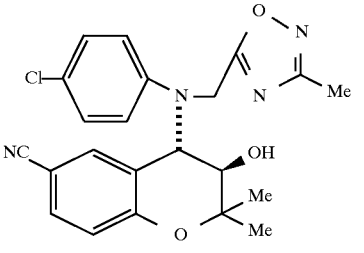

| M. P. °C. (solvent) | Rotation [α]$_D$° | Analysis |
|---|---|---|
| 148–149 | +60.6 (MeOH) | Calculated for $C_{22}H_{22}N_4O_3$: C, 67.68; H, 5.68; N, 14.35. Found: 67.74; H, 5.58; N, 14.34. |

EXAMPLE 90

(3R-trans)-4-[(4-Chlorophenyl)[(3-methyl-1,2,4-oxadiazol-5-yl)-methyl]amino]-3,4-dihydro-3-hydroxy-2,2-dimethyl-2H-1-benzopyran-6-carbonitrile

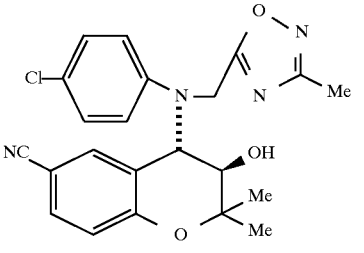

| M. P. °C. (solvent) | Rotation [α]$_D$° | Analysis |
|---|---|---|
| 102–105 (hexanes) | +79 (MeOH) | Calculated for $C_{22}H_{21}N_4ClO_3 \cdot 0.24 H_2O$: C, 61.57; H, 5.04; N, 13.05; Cl, 8.26. Found: C, 62.00; H, 5.09; N, 12.62; Cl, 8.64. |

EXAMPLE 91

(3R-trans)-4-[(4-Fluorophenyl)[(3-methyl-1,2,4-oxadiazol-5-yl)-methyl]amnino]-3,4-dihydro-3-hydroxy-2,2-dimethyl-2H-1-benzopyran -6-carbonitrile

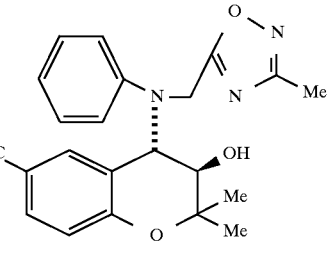

| M. P. °C. (solvent) | Rotation [α]$_D$° | Analysis |
|---|---|---|
| 116–118 (hexanes) | +37.6 (MeOH) | Calculated for $C_{22}H_{21}N_4FO_3 \cdot 0.02 H_2O$: C, 64.65; H, 5.19; N, 13.71; F, 4.65. Found: C, 64.65; H, 5.19; N, 13.71; F, 4.65. |

EXAMPLE 92

(3R-trans)-[N-[3,4-Dihydro-3-hydroxy-2,2-dimethyl-7-(trifluoromethyl)-2H-1-benzopyran-4yl]phenylamino]acetic acid, ethyl ester

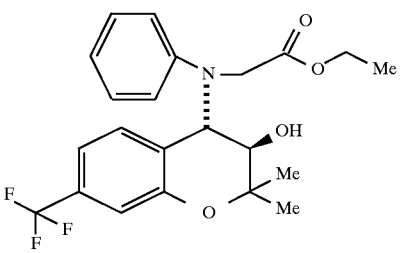

| M. P. °C. (solvent) | Rotation $[\alpha]_D°$ | Analysis |
|---|---|---|
| 100–103 | −102 (CHCl$_3$) | Calculated for C$_{22}$H$_{24}$NF$_3$O$_4$: C, 62.19; H, 5.73; N, 3.30. Found: C, 62.33; H, 5.54; N, 3.16. |

EXAMPLE 93

(3R-trans)-3,4Dihydro-3-hydroxy-4-[N-[[3(hydroxymethyl)-1,2,4-oxadiazol-5-yl)methyl]phenylamino]-2,2-dimethyl-2H-1-benzopyran-6-carbonitrile

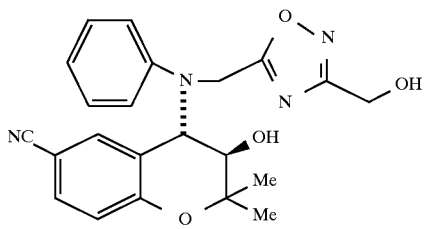

| M. P. °C. (solvent) | Rotation $[\alpha]_D°$ | Analysis |
|---|---|---|
| 95–98 (hexanes) | +69.8 (MeOH) | Calculated for C$_{22}$H$_{22}$N$_4$O$_4$: C, 65.01; H, 5.46; N, 13.78. Found: C, 64.77; H. 5.46; N, 13.46. |

EXAMPLE 94

(3R-trans)-[N-[3,4-Dihydro-3-hydroxy-2,2dimethyl-8(trifluoromethyl)-2H-1-benzopyran-4-yl]phenylamino]acetic acid, ethyl ester

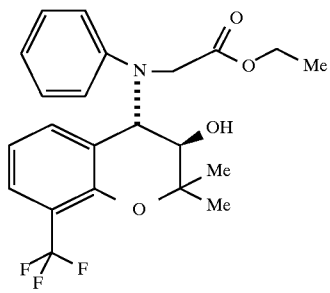

| M. P. °C. (solvent) | Rotation $[\alpha]_D°$ | Analysis |
|---|---|---|
| 45–48 | +82 (CHCl$_3$) | Calculated for C$_{22}$H$_{24}$NF$_3$O$_4$. 0.17 H$_2$O: C, 61.96; H, 5.75; N, 3.28. Found: C, 62.34; H, 5.52; N, 2.90. |

EXAMPLE 95

(3R-trans)-4-[(4-Chlorophenyl)[[3-(hydroxymethyl)-1,2,4-oxadiazol-5-yl]methyl]amino]-3,4-dihydro-3-hydroxy-2,2-dimethyl-2H-1-benzopyran-6-carbonitrile

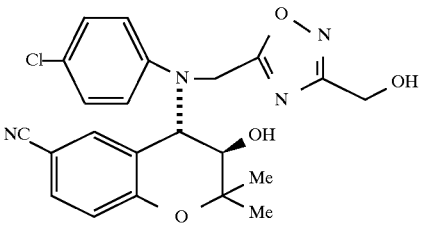

| M. P. °C. (solvent) | Rotation $[\alpha]_D°$ | Analysis |
|---|---|---|
| 101–103 (hexanes) | +83 (MeOH) | Calculated for C$_{22}$H$_{21}$N$_4$ClO$_4$. 0.19 H$_2$O: C, 59.46; H, 4.85; N, 12.61; Cl, 7.98. Found: C, 59.82; H, 4.77; N, 12.25; Cl, 7.58. |

EXAMPLE 96

(3R-trans)-4-[(4-Fluorophenyl)[[3-(hydroxymethyl)-1,2,4-oxadiazol-5-yl]methyl]amino]-3,4-dihydro-3-hydroxy-2,2-dimethyl-2H-1-benzopyran-6-carbonitrile

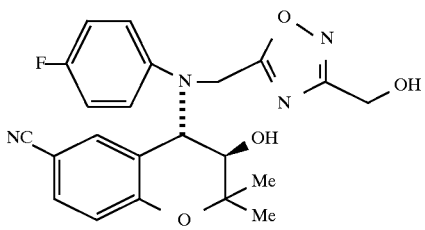

| M. P. °C. (solvent) | Rotation [α]_D° | Analysis |
|---|---|---|
| 115–118 | +40.3 (MeOH) | Calculated for $C_{22}H_{21}FN_4O_4 \cdot 0.75\ H_2O$: C, 60.35; H, 5.18; N, 12.79; F, 4.34. Found: C, 60.73; H, 4.85; N, 12.41; F, 4.09. |

EXAMPLE 97

(3R-trans)-4-[N-[(3-Amino-1,2,4-oxadiazol-5-yl)methyl]-phenylamino]-3,4-dihydro-3-hydroxy-2,2-dimethyl-2H-1-benzopyran-6-carbonitrile

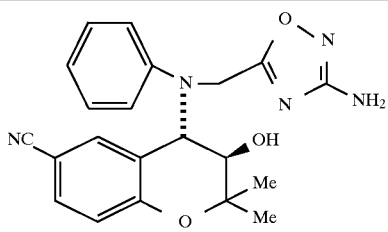

| M. P. °C. (solvent) | Rotation [α]_D° | Analysis |
|---|---|---|
| 203–205 | +51.4 (MeOH) | Calculated for $C_{21}H_{21}N_5O_3 \cdot 0.5\ H_2O$: C, 62.99; H, 5.41; N, 17.49. Found: C, 63.43; H, 5.18; N, 17.05. |

EXAMPLE 98

(3R-trans)-[N-(6-Benzoyl-3,4-dihydro-3hydroxy-2,2-dimethyl-2H-1-benzopyran-4-yl)phenylamino] acetic acid, ethyl ester

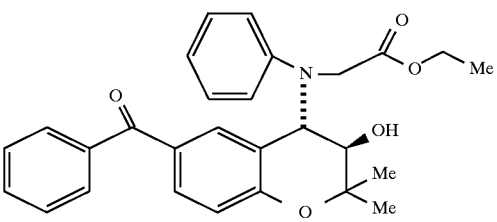

| M. P. °C. (solvent) | Rotation [α]_D° | Analysis |
|---|---|---|
| 144–145 | +58.9 (MeOH) | Calculated for $C_{28}H_{29}NO_5 \cdot 0.19\ H_2O$: C, 72.65; H, 6.40; N, 3.03. Found: C, 72.72; H, 6.70; N, 2.96. |

EXAMPLE 99

(3R-trans)-[(6Cyano-3,4-dihydro-3hydroxy-2,2-dimethyl-2H-1-benzopyran-4-yl)[4-fluoro-3-[(phenylmethoxy)carbonyl]phenyl]-amino]acetic acid, ethyl ester

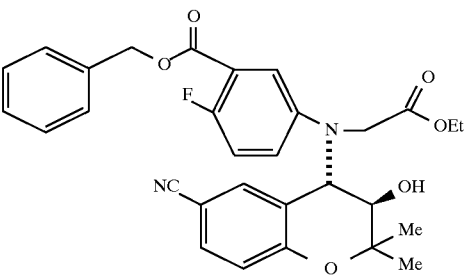

| M. P. °C. (solvent) | Rotation [α]_D° | Analysis |
|---|---|---|
| 61—61 | +31.8 (MeOH) | Calculated for $C_{30}H_{29}FN_2O_6 \cdot 1.24\ H_2O$: C, 64.93; H, 5.72; N, 5.05. Found: C, 65.24; H, 5.33; N, 4.74. |

EXAMPLE 100

(3R-trans)-[[5[[(6-Cyano-3,4-dihydro-3-hydroxy-2,2-dimethyl-2H-1-benzopyran-4-yl)(4-fluorophenyl)amino]methyl]-1,2,4oxadiazol-3-yl]methoxy]acetic acid

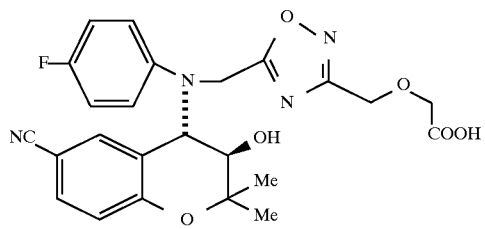

| M. P. °C. (solvent) | Rotation [α]$_D$° | Analysis |
|---|---|---|
| 125–128 | +30 (MeOH) | Calculated for C$_{24}$H$_{23}$FN$_4$O$_6$·1.47 H$_2$O: C, 58.72; H, 4.91; N, 11.41; F, 3.87. Found: C, 59.15; H, 4.22; N, 10.98; F, 3.55. |

EXAMPLE 101

(3R-trans)-[[5[[(4-Chlorophenyl)(6-cyano-3,4-dihydro-3-hydroxy-2,2-dimethyl-2H-1-benzopyran-4-yl)amino]methyl]-1,2,4-oxadiazol-3-yl]methoxy]acetic acid

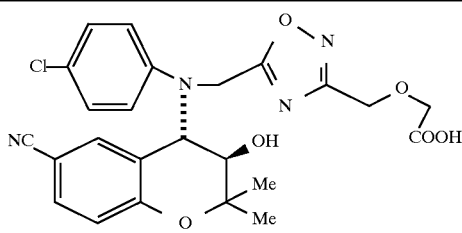

| M. P. °C. (solvent) | Rotation [α]$_D$° | Analysis |
|---|---|---|
| 145–148 | +51.7 (MeOH) | Calculated for C$_{24}$H$_{23}$ClN$_4$O$_6$: C, 57.78; H, 4.65; N, 11.23; Cl, 7.11. Found: C, 57.45; H, 4.74; N, 10.98; Cl, 7.07. |

EXAMPLE 102

(3R-trans)-[(3-Carboxy-4-fluorophenyl)(6-cyano-3,4-dihydro-3-hydroxy-2,2dimethyl-2H-1-benzopyran-4-yl)amino]acetic acid, ethyl ester

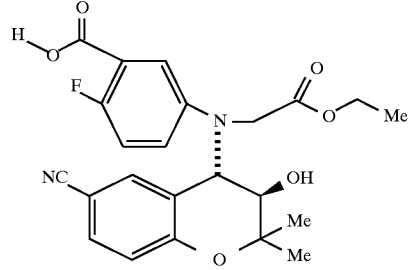

| M. P. °C. (solvent) | Rotation [α]$_D$° | Analysis |
|---|---|---|
| 195–197 | +51.4 (MeOH) | Calculated for C$_{23}$H$_{23}$FN$_2$O$_6$·0.35 H$_2$O: C, 59.40; H, 5.06; N, 5.93. Found: C, 59.70; H, 4.76; N, 5.60. |

EXAMPLE 103

(3R-trans)-4-[(4-Fluorophenyl)[(2-methyl-2H-tetrazol-5-yl)methyl]-amino-3,4-dihydro-3-hydroxy-2,2-dimethyl-2H-1-benzopyran-6-carbonitrile

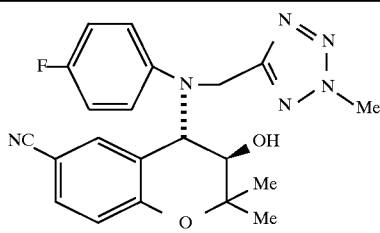

| M. P. 0° C. (solvent) | Rotation [α]$_D$° | Analysis |
|---|---|---|
| 145–148 | | Calculated for C$_{21}$H$_{21}$FN$_6$O$_2$; C, 61.76; H, 5.18; N, 20.58. Found: C, 61.87; H, 4.96; N, 20.74. |

EXAMPLE 104

(3R-trans)-4-[(4-Fluorophenyl)[(1-methyl-1H-tetrazol-5-yl)methyl]-amino-3,4-dihydro-3-hydroxy-2,2-dimethyl-2H-1-benzopyran-6-carbonitrile

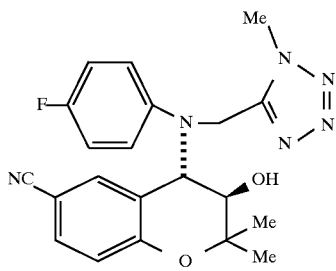

| M. P. °C. (solvent) | Rotation [α]$_D$° | Analysis |
|---|---|---|
| 130–135 | | Calculated for $C_{21}H_{21}FN_6O_2$: |
| | | C, 61.76; H, 5.18; N, 20.58. |
| | | Found: C, 61.62; H, 5.23; N, 19.85. |

EXAMPLE 105

(3R-trans)-3,4-Dihydro-3-hydroxy-2,2-dimethyl-4-[N-[2-methylsulfinyl)ethyl]phenylamino]-2H-1-benzopyran-6carbonitrile

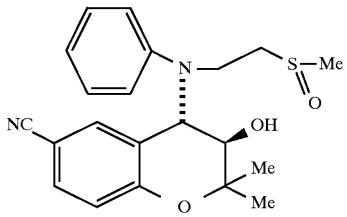

| M. P. °C. (solvent) | Rotation [α]$_D$° | Analysis |
|---|---|---|
| 75–85 (shrinks) | −122 (CHCl$_3$) | Calculated for $C_{21}H_{24}N_2O_3S$. |
| | | 0.46 H$_2$O: C, 64.21; H, 6.40; |
| | | N, 7.13; S, 8.16. |
| | | Found: C, 64.26; H, 6.38; N, 7.08; |
| | | S, 7.88. |

EXAMPLE 106

(3R-trans)-3,4Dihydro-3-hydroxy-2,2-dimethyl-4-[N-[2-(methylsulfonyl)ethyl]phenylamino]-2H-1-benzopyran-6-carbonitrile

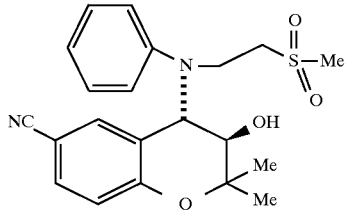

| M. P. °C. (solvent) | Rotation [α]$_D$° | Analysis |
|---|---|---|
| 75–85 (skrinks) | −76.9 (CHCl$_3$) | Calculated for $C_{21}H_{24}N_2O_3S$. |
| | | 0.58 H$_2$O: C, 61.37; H, 6.17; |
| | | N, 6.82; S, 7.80. |
| | | Found: C, 61.76; H, 61.5; N, 6.43; |
| | | N, 7.53. |

EXAMPLE 107

(3R-trans)-4-[4-Chloro-N-[(1H-imidazol-2-yl)methyl]phenylamino]-3,4-dihydro-3-hydroxy-2,2-dimethyl-2H-1-benzopyran-6-carbonitrile, monohydrochloride

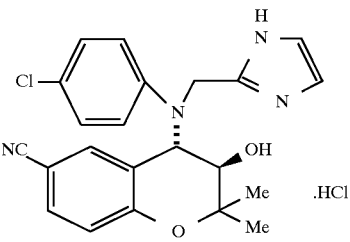

A. N-(4-Chlorophenyl)-N-[(1H-imidazol-2-yl)methyl]amine

A mixture of 4-chloroaniline (66.65 g, 522.43 mmol) and 2-imidazolecarboxaldehyde (50.2 g, 522.43 mmol) in methanol (1000 mL) was stirred at 55°–60° C. overnight. The light brown reaction mixture was cooled in an ice bath and treated with sodium borohydride (21.74 g, 574.67 mmol) in small portions. The reaction mixture was allowed to warm to room temperature and stirred for two hours. It was concentrated and partitioned between water (~500 mL) and ethyl acetate (1200 mL), giving a white solid/aqueous layer and a brown organic layer. The organic layer was removed and the aqueous mixture was reextracted with ethyl acetate (3×200 mL). The combined organic layers were washed with brine, dried over sodium sulfate and concentrated. The resulting mixture was treated with hexanes and stored in the freezer for two hours. The white solid was collected by filtration and washed with cold ethyl acetate/hexane (2:1) to provide the title product (83.36 g, 77%) as a white solid, mp 163°–165° C. Analysis calculated for $C_{10}H_{10}ClN_3$: C, 57.84; H, 4.85; N, 20.23; Cl, 17.07. Found: C, 57.82; H, 4.85; N, 20.04; Cl, 16.77.

B. (3R-trans)-4-[4-Chloro-N-[(1H-imidazol-2-yl)methyl]-phenylamino]-3,4-dihydro-3-hydroxy-2,2-dimethyl-2H-1-benzopyran-6-carbonitrile A mixture of title A compound (41.3 g, 198.79 mmol), title A compound of Example 3 (40.0 g, 198.79 mmol) and anhydrous cobalt chloride (25.8 g, 198.79 mmol) in dry acetonitrile (160 mL) under argon was heated at 60° C. (oil bath temperature) for 28 hours. The reaction mixture was allowed to cool to room temperature and treated with saturated sodium bicarbonate (600 mL) followed by ethyl acetate (1600 mL). The well shaken mixture was filtered through a short pad of celite, yellow organic layer was separated and washed with brine. After drying over anhydrous sodium sulfate, the solvent was removed and the residue was treated with hexanes (1000 mL) and ethyl acetate (100 mL). The mixture was heated on a steam bath (10–20 minutes), allowed to cool to room temperature and filtered to afford a white solid. This material was heated with methanol (2000 mL) for 15 minutes, allowed to cool to room temperature and filtered to provide (3R-trans)-4-[4-Chloro-N-[(1H-imidazol-2-yl)methyl]phenylamino]-3,4-dihydro-3-hydroxy-2,2-dimethyl-2H-1-benzopyran-6-carbonitrile (44.72 g, 55%) as a colorless solid mp 266°–267° C. $[\alpha]_D$=+46.9° (c=1.15, acetone).

C. (3R-trans)-4-[4-Chloro-N-[(1H-imidazol-2-yl)methyl]-phenylamnino]-3,4-dihydro-3-hydroxy-2,2-dimethyl-2H-1-benzopyran-6-carbonitrile, mono hydrochloride A solution of title B compound (50.0 g, 122.29 mmol) in anhydrous tetrahydrofuran (800 mL) at 0° C. was treated with a freshly prepared 4.0N hydrogen chloride gas in diethyl ether (36.6 mL, 178.61 mmol). The solution was stirred at 0° C. for ten minutes and the solvent was removed to give a yellow oil which was treated with diethyl ether to give the title product (55.87 g, 98%) as a white solid, mp 189°–190° C. Analysis calculated for $C_{22}H_{21}ClN_4O_2 \cdot HCl \cdot 0.40H_2O \cdot 0.20THF$: C, 58.64; H, 5.27; N, 12.00; Cl, 15.18. Found: C, 58.72; H, 5.39; N, 11.72; Cl, 15.46. $[\alpha]_D$=+9.5° (c=1.00, MeOH)

EXAMPLE 108

(3R-trans)-4-[4-Chloro-N-[(1H-imidazol-2-yl)methyl]phenylamino]-3,4-dihydro-3-hydroxy-2,2-dimethyl-2H-1-benzopyran-6-carbonitrile, hydrogensulfate

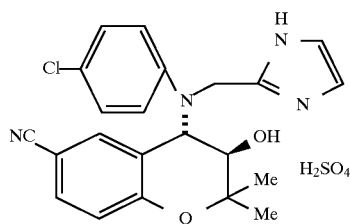

The title compound was prepared from the title B compound of Example 107 by treatment with concentrated sulfuric acid in tetrahydrofuran. The solvent was removed and the product was triturated with ether to give a colorless solid, mp 154°–156° C. Analysis calculated for $C_{22}H_{21}ClN_4O_2 \cdot H_2SO_4 \cdot 0.9H_2O \cdot 0.30Et_2O$: C, 51.09; H, 5.14; N, 10.27; Cl, 6.50; S, 5.88. Found: C, 50.89; H, 4.83; N, 10.01; Cl, 6.67; S, 6.17. $[\alpha]_D$=+6.80° (c=1. 12, MeOH).

EXAMPLE 109

(3R-trans)-4-[4-Chloro-N-[(1H-imidazol-2-yl)methyl]phenylamino]-3,4-dihydro-3-hydroxy-2,2-dimethyl-2H-1-benzopyran-6-carbonitrile, methanesulfonate

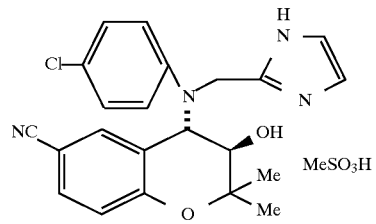

The title compound was prepared from the title B compound of Example 107 by treatment with methanesulfonic acid in tetrahydrofuran. The solvent was removed and the product was triturated with ether to give a colorless solid, mp 155°–156° C. Analysis calculated for $C_{22}H_{21}ClN_4O_2 \cdot MeSO_3H \cdot 1.0H2O \cdot 0.06Et_2O$: C: 52.92; H, 5.27; N, 10.62; Cl, 6.72; S, 6.08. Found: C, 52.92; H, 5.17; N, 10.23; Cl, 6.50; S, 6.57. $[\alpha]_D$=+8.0° (c=1.31, MeOH).

EXAMPLE 110

(3R-trans)-4-[4-Chloro-N-[(1H-imidazol-2-yl)methyl]phenylamino]-3,4-dihydro-3-hydroxy-2,2-dimethyl-2H-1-benzopyran-6-carbonitrile, phosphate

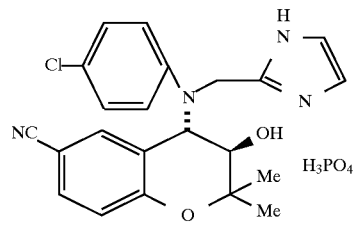

The title compound was prepared from the title B compound of Example 107 by treatment with phosphoric acid in tetrahydrofuran. The solvent was removed and the product was triturated with ether to give a colorless solid, mp 160°–161° C. Analysis calculated for $C_{22}H_{21}ClN_4O_2 \cdot H_3PO_4 \cdot 3.4H_2O \cdot 0.35Et_2O$: C, 47.31; H, 5.82; N, 9.43; Cl, 5.87. Found: C, 47.34; H, 5.06; N, 9.07; Cl, 5.92. $[\alpha]_D$=+18.80° (c=1.18, MeOH).

EXAMPLE 111

(3R-trans)-4-[4-Chloro-N-[(1H-imidazol-2-yl)methyl]phenylamino]-3,4-dihydro-3-hydroxy-2,2-dimethyl-2H-1-benzopyran-6-carbonitrile, nitrate

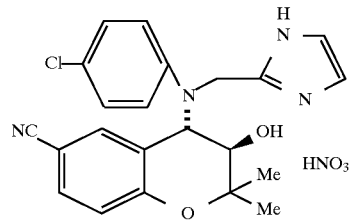

The title compound was prepared from the title B compound of Example 107 by treatment with nitric acid in tetrahydrofuran. The solvent was removed and the product was triturated with ether to give a colorless solid, mp 141°–142° C. (decomposition). Analysis calculated for $C_{22}H_{21}ClN_4O_2 \cdot HNO_3 \cdot 0.48H_2O \cdot 0.20Et_2O$: C, 55.28; H, 5.08; N, 14.14; Cl, 7.16. Found: C, 55.29; H, 5.11; N, 13.82; Cl, 7.05. $[\alpha]_D = +8.3$ (c=0.99, MeOH).

EXAMPLE 112

[3R-[3α,4β(R*)]]-3,4-Dihydro-3-hydroxy-2,2-dimethyl-4[N-[[5-oxo-1-(phenylmethyl)-2-pyrrolidinyl]methyl]phenylamino]-2H-1-benzopyran-6-carbonitrile

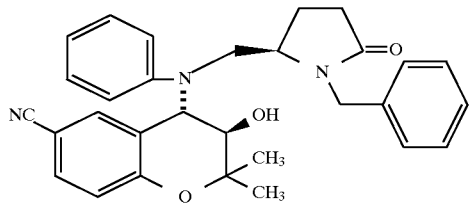

| M. P. °C. (solvent) | Rotation $[\alpha]_D°$ | Analysis |
|---|---|---|
| 161–163 | –102 (CHCl$_3$) | Calculated for $C_{30}H_{31}N_3O_3$. 0.53 H$_2$O: C, 73.36; H, 6.58; N, 8.55. Found: C, 73.59; H, 6.49; N, 8.32 |

EXAMPLE 113

[3R-[3α,4β(S*)]]-3,4-Dihydro-3-hydroxy-2,2-dimethyl-4-[N-[[5-oxo-2-pyrrolidinyl)methyl]phenylamino]-2H-1-benzopyran -6-carbonitrile

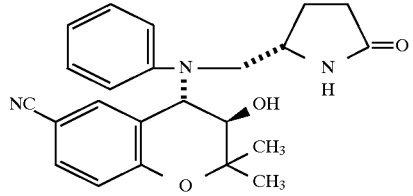

| M. P. °C. (solvent) | Rotation $[\alpha]_D°$ | Analysis |
|---|---|---|
| 186–189 | –116 (CHCl$_3$) | Calculated for $C_{23}H_{25}N_3O_3$. 0.50 H$_2$O: C, 68.98; H, 6.54; N, 10.49. Found: C, 69.16; H, 6.49; N, 10.31. |

EXAMPLE 114

[3R-[3α,4β(R*)]]-3,4-Dihydro-3-hydroxy-2,2-dimethyl-4-[N-[(5-oxo-2-pyrrolidinyl)methyl]phenylamino]-2H-1-benzopyran-6-carbonitrile

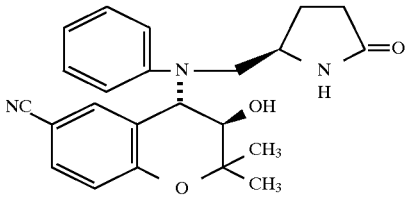

| M. P. °C. (solvent) | Rotation $[\alpha]_D°$ | Analysis |
|---|---|---|
| amorphous solid | –34 (CHCl$_3$) | Calculated for $C_{23}H_{25}N_3O_3$. 0.86 H$_2$O.0.25C$_6$H$_{14}$O: C, 68.04; H, 7.04; N, 9.72. Found: C, 68.03; H, 6.68; N, 9.68. |

EXAMPLE 115

(3R-trans)-4-[N-[(1,5-Dimethyl-1H -pyrazol-3-yl)methyl]phenylamino] -3,4-dihydro-3-hydroxy-2,2-dimethyl-2H-1-benzopyran-6-carbonitrile

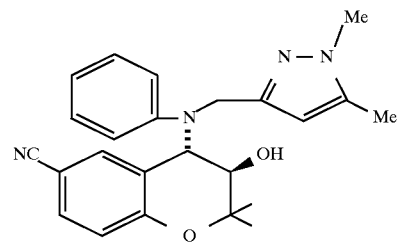

| M. P. °C. (solvent) | Rotation $[\alpha]_D°$ | Analysis |
|---|---|---|
| 194–199 | +27.1 (MeOH) | Calculated for $C_{24}H_{26}N_4O_2 \cdot 0.23$ H$_2$O: C, 70.90; H, 6.56; N, 13.78. Found: C, 70.99; H, 6.55; N, 13.69. |

EXAMPLE 116

(3R-trans)-3,4-Dihydro-3-hydroxy-2,2-dimethyl-4-[N-[(5-methyl-1H-pyrazol-3-yl)methyl]phenylamino]-2H-1-benzopyran-6-carbonitrile

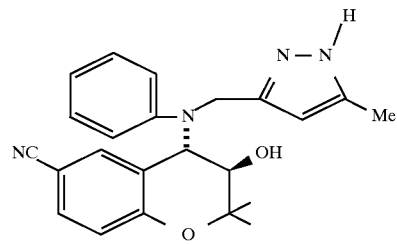

| M. P. °C. (solvent) | Rotation $[\alpha]_D°$ | Analysis |
|---|---|---|
| 110–120 | +30.8 (MeOH) | Calculated for $C_{23}H_{24}N_4O_2.0.78$ $H_2O$: C, 68.63; H, 6.40; N, 13.92. Found: C, 69.06; H, 6.46; N, 13.50. |

EXAMPLE 117

(3R-trans)-4-[N-[(1,3-Dimethyl-1H-pyrazol-5-yl)methyl]phenyl-amino]-3,4-dihydro-3-hydroxy-2,2-dimethyl-2H-1-benzopyran-6-carbonitrile

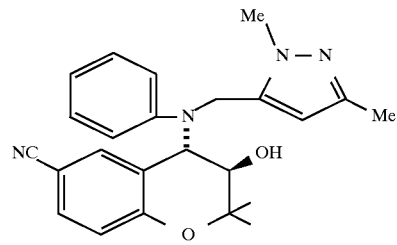

| M. P. °C. (solvent) | Rotation $[\alpha]_D°$ | Analysis |
|---|---|---|
| 108–115 | +7.9 (MeOH) | Calculated for $C_{24}H_{26}N_4O_2.0.50$ $H_2O.0.30\ C_4H_8O_2$: C, 69.11; H, 6.77; N, 12.79. Found: C, 69.20; H, 6.63; N, 12.74. |

EXAMPLE 118

[3R-[3α,4β-(Z)]]-4-[N-(2-Amino-4oxo-2-pentenyl)phenylamino]-3,4-dihydro-3-hydroxy-2,2dimethyl-2H-1-benzopyran-6-carbonitrile

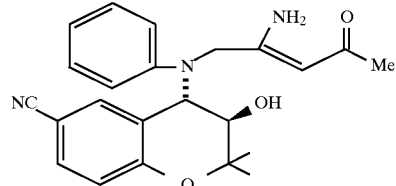

| M. P. °C. (solvent) | Rotation $[\alpha]_D°$ | Analysis |
|---|---|---|
| 188–190 | −52.0 (MeOH) | Calculated for $C_{23}H_{25}N_3O_3$: C, 70.57; H, 6.44; N, 10.73. Found: C, 70.34; H, 6.52; N, 10.47. |

What is claimed is:
1. A compound of the formula

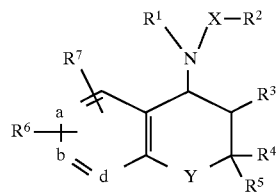

or pharmaceutically acceptable salts thereof wherein
a, b and d are all carbon atoms;
Y is a single bond, —O— or —S—;
$R^1$ is aryl or heterocyclo;
$R^2$ is —$COOR^8$, —CO-amino, —CO-substituted amino, amino, substituted amino, —$NR^8CO$-amino, —$NR^8CO$-substituted amino, —$NR^8COR^9$, —$NR^8SO_2R^9$, —$NR^8(C=NCN)$-amino, —$NR^8(C=NCN)$-substituted amino,

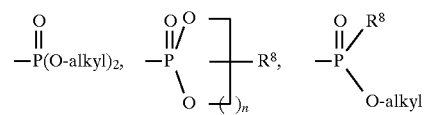

—$SR^8$, —$SOR^8$, —$SO_2R^8$, —$OR^8$, cyano, heterocyclo, pyridine-N-oxide, —$CH(OR^8)_2$,

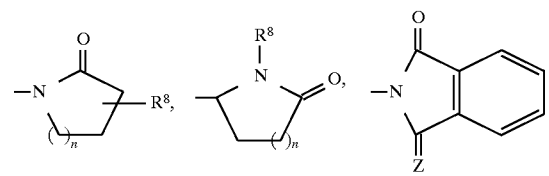

(where Z is O or $H_2$) or

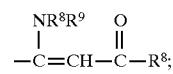

$R^3$ is hydrogen, hydroxy or —$OC(O)R^8$;

R[4] and R[5] are each independently hydrogen, alkyl or arylalkyl, or R[4] and R[5] taken together with the carbon atom to which they are attached form a 5- to 7-membered carbocyclic ring;

R[6] is hydrogen, alkyl, haloalkyl, alkenyl, alkynyl, cycloalkyl, arylalkyl, (cycloalkyl)alkyl, —CN, —NO$_2$, —COR[8], —COOR[8], —CONHR[8], —CONR[8]R[9], —CF$_3$, —S-alkyl, —SOalkyl, —SO$_2$alkyl,

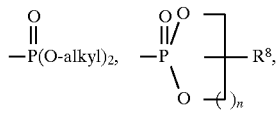

halogen, amino, substituted amino, —O-alkyl, —OCF$_3$, —OCH$_2$CF$_3$, —OCOalkyl, —OCONR[8]alkyl, —NR[8]COalkyl, —NR[8]COOalkyl or —NR[8]CONR[9], tetrazolyl, imidazole, oxazole or triazole;

R[7] is hydrogen, alkyl, hydroxy, —O-alkyl, amino, substituted amino, —NHCOR[8], —CN or —NO$_2$;

R[8] and R[9] are independently hydrogen, alkyl, haloalkyl, aryl, arylalkyl, cycloalkyl or (cycloalkyl)alkyl;

X is alkyl; or X-R[2] together can be aryl or heterocyclo when R[1] is heterocyclo; and n is an integer of 1 to 3; provided that when R[1] is aryl, then R[2] is other than —COOR[8], amino, substituted amino, —OR[8] and cyano.

2. The compounds as recited in claim 1 wherein
a, b and d are carbon atoms;
X is alkyl;
Y is a single bond or —O—;
R[1] is aryl or heterocyclo;
R[2] is, —COamino, —CO-substituted amino, —NHCOCH$_3$, —NHSO$_2$Me, —NHCONH$_2$, —NH(C=NCN)NH$_2$, imidazole, fliran, pyridine, oxazole, —NHCO-substituted amino or —SO$_2$Me;
R[3] is hydroxy;
R[4] and R[5] are methyl;
R[6] is cyano, —NO$_2$, —CF$_3$, halo, alkyl or tetrazol; and
R[7] is hydrogen.

3. The compounds as recited in claim 1, which are:
trans-[(6-cyano-3,4-dihydro-3-hydroxy-2,2-dimethyl-2H-1-benzo-yran-4-yl)phenylamino]acetic acid, ethyl ester;
(3S-trans)-[(6-cyano-3,4-dihydro-3-hydroxy-2,2-dimethyl-2H1-benzopyran-4-yl)phenylamino]acetic acid, ethyl ester;
(3R-trans)-[(6-cyano-3,4-dihydro-3-hydroxy-2,2-dimethyl-2H-1-benzopyran-4-yl)phenylaminolacetic acid, ethyl ester;
trans-[(6-cyano-3,4-dihydro-3-hydroxy-2,2-dimethyl-2H-1-benzo-pyran-4-yl)phenylamino]acetic acid;
(3R-trans)-[(6-cyano-3,4-dihydro-3-hydroxy-2,2-dimethyl-2H-1-benzopyran-4-yl)(4-fluorophenyl)amino]acetic acid, ethyl ester,
(3R-trans)-[(6-cyano-3,4-dihydro-3-hydroxy-2,2-dimethyl-2H-1-benzopyran-4-yl)(4-chlorophenyl)amino]acetic acid, ethyl ester;
(3R-trans)-[(6-cyano-3,4-dihydro-3-hydroxy-2,2-dimethyl-2H-1-benzopyran-4-yl)phenylamino]acetamide;
(3S-trans)-3,4-dihydro-3-hydroxy-2,2-dimethyl-4-[(4-phenyl-2-thiazolyl)amino]-2H-1-benzopyran-6-carbonitrile;
(3R-trans)-3,4-dihydro-3-hydroxy-2,2-dimethyl-4-[(4-phenyl-2-thiazolyl)amino]-2H-1-benzopyran-6-carbonitrile;
(3R-trans)-[N-[3,4-dihydro-3-hydroxy-2,2-dimethyl-6-(1H-tetrazol-5-yl)-2H-1-benzopyran-4-yl]phenylamino]acetic acid, ethyl ester;
(3R-trans)-2[N-(6-cyano-3,4-dihydro-3-hydroxy-2,2-dimethyl-2H-1-benzopyran-4-yl)phenylamino]-N-ethylacetamide;
(3R-trans)-3,4-dihydro-3-hydroxy-2,2-dimethyl-4-[N[2-(1-pyrrolidinyl)-2-oxoethyl]phenylanmino]-2H-1-benzopyran-6-carbonitrile;
(3R-trans)-3,4-dihydro-3-hydroxy-2,2-dimethyl-4-[N[2-(4-morpholinyl)-2-oxoethyl]phenylamino]-2H-1-benzopyran-6-carbonitrile;
(3R-trans)-[N-(6-cyano-3,4-dihydro-3-hydroxy-2,2-dimethyl-2H-1-benzopyran-4-yl)phenylamino]-N-(2-furanylmethyl)acetamide;
(3R-trans)-[N-(6-cyano-3,4-dihydro-3-hydroxy-2,2-dimethyl-2H-1-benzopyran-4-yl)phenylamino]-N-[2-(4-morpholinyl)ethyl]acetamide;
(3R-trans)-4-[(4-fluorophenyl)(2-hydroxy-2-methylpropyl)-amino]-3,4-dihydro-3-hydroxy-2,2-dimethyl-2H-1-benzopyran-6-carbonitrile;
[3R-[3a,4b(R*)]]-4-[(4-fluorophenyl)(2-hydroxypropyl)amno]-3,4-dihydro-3-hydroxy-2,2-dimethyl-2H-1-benzopyran-6-carbonitrile;
(3R-trans)-[(6-cyano-3,4-dihydro-3-hydroxy-2,2-dimethyl-2H-1-benzopyran-4-yl)(4-methyl-2-thiazolyl)amino]acetic acid, ethyl ester;
(3R-trans)-4-[N-(2-benzoxazolyl)-N-(2,2-dimethoxyethyl)amino]-3,4-dihydro-3-hydroxy-2,2-dimethyl-2H-1-benzopyran-6-carbonitrile;
(3R-trans)-4-[N-[1,3-dihydro-1,3-dioxo-2H-isoindol-2-yl)ethyl]-phenylamino]-3,4-dihydro-3-hydroxy-2,2-dimethyl-2H-1-benzopyran-6- carbonitrile;
(3R-trans)-4-[N-(2-aminoethyl)phenylamino]-3,4-dihydro-3-hydroxy-2,2-dimethyl-2H-1-benzopyran-6-carbonitrile;
(3R-trans)-[(6-cyano-3,4-dihydro-3-hydroxy-2,2-dimethyl-2H-1-benzopyran-4-yl)phenylamino]butyric acid, ethyl ester;
(3R-trans)-3-[N-(6-cyano-3,4-dihydro-3-hydroxy-2,2-dimethyl-2H-1-benzopyran-4-yl)phenylamino]propanoic acid, ethyl ester;
(3R-trans)-3,4-dihydro-3-hydroxy-4-[N-[(1H-imidazol-2-yl)-methyl]phenylamino]-2,2-dimethyl-2H-1-benzopyran-6-carbonitrile;
(3R-trans)-4-[[2-(acetylamino)ethyl]phenylamino]-3,4-dihydro-3-hydroxy-2,2-dimethyl-2H-1-benzopyran-6-carbonitrile;
(3R-trans)-[2-[N-(6-cyano-3,4-dihydro-3-hydroxy-2,2-dimethyl-2H-1-benzopyran-4-yl)phenylamino]ethyl]urea;
(3R-trans)-N-[2-[N-(6-cyano-3,4-dihydro-3-hydroxy-2,2-dimethyl-2H-1-benzopyran-4-yl)phenylamino]ethyl]methanesulfonamide;
(3R-trans)-N"-cyano-N-[2-[[N-(6-cyano-3,4-dihydro-3-hydroxy-2,2-dimethyl-2H-1-benzopyran-4-yl)phenylamino]ethyl]guanidine;
(3R-trans)-2[N-(6-cyano-3,4-dihydro-3-hydroxy-2,2-dimethyl-2H-1-benzopyran-4-yl)phenylamino]-N-(2-hydroxyethyl)acetamide;
(3R-trans)-4-[4-chloro-N-[(1H-imidazol-2-yl)methyl]-phenylamino]-3,4-dihydro-3-hydroxy-2,2-dimethyl-2H-1-benzopyran-6- carbonitrile;

(3R-trans)-4-[4-fluoro-N-[(1H-imidazol-2-yl)methyl]-phenylamino]-3,4-dihydro-3-hydroxy-2,2-dimethyl-2H-1-benzopyran-6-carbonitrile, mono hydrochloride;

(3R-trans)-4-[N-(2-furanylmethyl)phenylamino]-3,4-dihydro-3-hydroxy-2,2-dimethyl-2H-1-benzopyran-6-carbonitrile;

(3R-trans)-4-[N-(2-furanylmethyl)phenylamino]-3,4-dihydro-3-hydroxy-2,2-dimethyl-2H-1-benzopyran-6-carbonitrile;

(3R-trans)-4-[N-[(4,5-dihydro-2-oxazolyl)methyl]phenylamino]-3,4-dihydro-3-hydroxy-2,2-dimethyl-2H-1-benzopyran-6-carbonitrile;

(3R-trans)-[(2-benzoxazolyl)(6-cyano-3,4-dihydro-3-hydroxy-2,2-dimethyl-2H-1-benzopyran-4yl)amino] acetic acid, ethyl ester;

(3R-trans)-4-[(2-benzoxazolyl)(2-pyridinylethyl)amino]-3,4-dihydro-3-hydroxy-2,2-dimethyl-2H-1-benzopyran-6-carbonitrile;

(3R-trans)-4-[(2-benzoxazolyl)(2-furanomethyl)amino]-3,4-dihydro-3-hydroxy-2,2-dimethyl-2H-1-benzopyran-6-carbonitrile;

(3R-trans)-4-[(2-furanylmethyl)(2-oxazolyl)amino]-3,4-dihydro-3-hydroxy-2,2-dimethyl-2H-1-benzopyran-6-carbonitrile;

(3R-trans)-4-[N-(cyanomethyl)phenylamino]-3,4-dihydro-3-hydroxy-2,2-dimethyl-2H-1-benzopyran-6-carbonitrile;

(3R-trans)-4-[N-(cyanoethyl)phenylamino]-3,4-dihydro-3-hydroxy-2,2-dimethyl-2H-1-benzopyran-6-carbonitrile;

(3R-trans)-3,4-dihydro-3-hydroxy-4-[N-(2-methoxyethyl)phenyl-amino]-2,2-dimethyl-2H-1-benzopyran-6-carbonitrile;

(3R-cis)-[N-(6-cyano-3,4-dihydro-3-hydroxy-2,2-dimethyl-2H-1-benzopyran-4-yl)phenylamino]-N-ethyl-acetamide;

(3R-trans)-3,4-dihydro-3-hydroxy-2,2-dimethyl-4-[N-[(5-methyl-3-isoxazolyl)methyl]phenylamino]-2H-1-benzopyran-6-carbonitrile;

(3R-trans)-4-[(4-fluorophenyl)[(5-methyl-3-isoxazolyl)methyl]-amino]-3,4-dihydro-3-hydroxy-2,2-dimethyl-2H-1-benzopyran-6-carbonitrile;

(3S-cis)-2-[N-(6-cyano-3,4-dihydro-3-hydroxy-2,2-dimethyl-2H-1-benzopyran-4-yl)phenylamino]-N-ethyl-acetamide;

(3R-tras)-[[[5-[[(3,4-dihydro-3-hydroxy-2,2-dimethyl-2H-1-benzopyran-4-yl)(4-fluorophenyl)amino]methyl]-2-furanyl]methyl]-amino]acetic acid, ethyl ester, monohydrochloride;

(3R-trans)-4-[(4-fluorophenyl)[[5-(hydroxymethyl)-2-furanyl]-methyl]amino]-3,4-dihydro-3-hydroxy-2,2-dimethyl-2H-1-benzopyran-6-carbonitrile;

(3R-trans)-[(6-cyano-3,4-dihydro-3-hydroxy-2,2-dimethyl-2H-1-benzopyran-4-yl)phenylamino]acetic acid, n-butyl ester;

(3R-trans)-[N-(6-cyano-3,4-dihydro-3-hydroxy-2,2-dimethyl-2H-1-benzopyran-4-yl)phenylamino]-N-phenylacetamide;

(3R-trans)-4-[N-(2-furanylmethyl)phenylamino]-3,4-dihydro-2,2-dimethyl-6-(1H-tetrazol-5-yl)-2H-1-benzopyran-3-ol;

(3R-trans)-3,4dihydro-3-hydroxy-2,2-dimethyl-4-[N-[(5-methyl-3-isoxazolyl)methyl]phenylamino]-2H-1-benzopyran-6-carbonitrile;

(3S-trans)-3,4dihydro-3-hydroxy-4-[N-[(1H-imidazol-2-yl)methyl]phenylamino]-2,2-dimethyl-2H-1-benzopyran-6-carbonitrile;

(3R-trans)-3,4-dihydro-3-hydroxy-2,2-dimethyl-4-[N-(2-oxazolylmethyl)phenylamino]-2H-1-benzopyran-6-carbonitrile;

(3R-trans)-2[[N-(6-cyano-3,4-dihydro-3-hydroxy-2,2-dimethyl-2H-1-benzopyran-4-yl)phenylamino]methyl]-4-oxazolecarboxylic acidethyl ester, (3R-trans)-2[[N-(6-cyano-3,4-dihydro-3-hydroxy-2,2-dimethyl-2H-1-benzopyran-4-yl)phenylamnino]methyl]-4-oxozolecarboxylic acid mono sodium salt;

(S*,R*)-N-[[N-(6-cyano-3,4-dihydro-3-hydroxy-2,2-dimethyl-2H-1-benzopyran-4-yl)phenylamino]acetyl]-L-serine, methyl ester;

(3R-trans)-4-[N-[(5-methyl-1,3,4-oxadiazol-2-yl)methyl]-phenylanimo]-3,4-dihydro-3-hydroxy-2,2-dimethyl-2H-1-benzopyran-6-carbonitrile;

(3R-trans)-4-[(4-chlorophenyl)(2-oxazolylmethyl)amino]-3,4-dihydro-3-hydroxy-2,2-dimethyl-2H-1-benzopyran-6-carbonitrile;

(3R-trans)-4-[N-(1H-benzimidazol-2-ylmethyl)phenylamino]-3,4-dihydro-3-hydroxy-2,2-dimethyl-2H-1-benzopyran-6-carbonitrile;

(3R-trans)-4-[(2-benzoxazolyl)[2-(4-morpholinyl)ethyl]amino]-3,4-dihydro-3-hydroxy-2,2-dimethyl-2H-1-benzopyran-6-carbonitrile;

(3R-trans)-4-[(2-furanylmethyl)(2-pyrimidinyl)amino]-3,4-dihydro-3-hydroxy-2,2-dimethyl-2H-1-benzopyran-6-carbonitrile;

(3R-trans)-3,4-dihydro-3-hydroxy-2,2-dimethyl-4-[(2-pyrazinyl)-(3-pyridinylmethyl)amino]-2H-1-benzopyran-6-carbonitrile;

(3R-trans)-3,4-dihydro-3-hydroxy-2,2-dimethyl-4-[(3-pyridinylmethyl)(2-pyrimidinyl)amino]-2H-1-benzopyran-6-carbonitrile;

(3R-trans)-4-[(2-benzoxazolyl)(2-pyridinylmethyl)-amino]-3,4dihydro-3-hydroxy-2,2-dimethyl-2H-1-benzopyran-6-carbonitrile;

(3R-trans)-3,4dihydro-3-hydroxy-2,2-dimethyl-4-[(2-pyrimidinyl)(2-pyridinylmethyl)amino]-2H-1-benzopyran-6-carbonitrile;

(3R-trans)-4-[(4-fluorophenyl)(2-pyridinylmethyl)amino]-3,4-dihydro-3-hydroxy-2,2-dimethyl-2H-1-benzopyran-6-carbonitrile;

4-[4-fluoro-N-(1H-imidazol-2-ylmethyl)phenylamino]-3,4-dihydro-2,2-dimethyl-2H-1-benzopyran-6-carbonitrile;

(3R-trans)-4-[(4-fluorophenyl)(2-pyrimidinyl)amino]-3,4-dihydro-3-hydroxy-2,2-dimethyl-2H-1-benzopyran-6-carbonitrile, monohydrochloride;

(3R-trans)-4-[(2-furanylmethyl)(2-pyrazinyl)amino]-3,4-dihydro-3-hydroxy-2,2-dimethyl-2H-1-benzopyran-6-carbonitrile;

(3R-trans)-4-[(2-benzothiazolyl)(3-pyridinylmethyl)amino]-3,4-dihydro-3-hydroxy-2,2-dimethyl-2H-1-benzopyran-6-carbonitrile;

(3R-trans)-4-[(4-fluorophenyl)(3-pyridinylmethyl)amino]-3,4-dihydro-3-hydroxy-2,2-dimethyl-2H-1-benzopyran-6-carbonitrile;

(3R-trans)-4-[(2-benzothiazolyl)(3-pyridinylmethyl)amino]-3,4-dihydro-3-hydroxy-2,2-dimethyl-2H-1-benzopyran-6-carbonitrile, 1-oxide;

(3R-trans)-4-[(4-chlorophenyl)[2-(4-morpholinyl)ethyl]amino]-3,4-dihydro-3-hydroxy-2,2-dimethyl-2H-1-benzopyran-6-carbonitrile, monohydrochloride;

(3R-trans)-4-[(4-fluorophenyl)[2-(4-morpholinyl)ethyl]amino]-3,4-dihydro-3-hydroxy-2,2-dimethyl-2H-1-benzopyran-6-carbonitrile, monohydrochloride;

(3R-trans)-4-[(6-chloro-3-pyridazinyl)[2-(4-morpholinyl)-ethyl]amino]-3,4-dihydro-3-hydroxy-2,2-dimethyl-2H-1-benzopyran-6-carbonitrile, hydrochloride;

(3R-trans)-4-[(2-benzothiazolyl)(1H-imidazol-2-ylmethyl)amino]-3,4-dihydro-3-hydroxy-2,2-dimethyl-2H-1-benzopyran-6-carbonitrile, monohydrochloride;

(3R-trans)-4-[(6-chloro-3-pyridazinyl)(1H-imidazol-2-ylmethyl)-amino]-3,4-dihydro-3-hydroxy-2,2-dimethyl-2H-1-benzopyran-6-carbonitrile, monohydrochloride;

(3R-trans)-4-[(5-trifluoromethyl-2-pyridinyl))(1H-imidazol-2-ylmethyl)amino]-3,4-dihydro-3-hydroxy-2,2-dimethyl-2H-1-benzopyran-6-carbonitrile, monohydrochloride;

(3R-trans)-3,4-dihydro-3-hydroxy-2,2-dimethyl-4-[[2-(4-morpholinyl)ethyl](4-phenyl-2-thiazolyl)amino]-2H-1-benzopyran-6-carbonitrile, monohydrochloride;

(3R-trans)-3,4-dihydro-3-hydroxy-4-[(1H-imidazol-2-ylmethyl)(4-phenyl-2-thiazolyl)amino]-2,2-dimethyl-2H-1-benzopyran-6-carbonitrile;

(3R-trans)-3,4-dihydro-3-hydroxy-4-[(1H-imidazol-2-ylmethyl)-(4-methyl-2-thiazolyl)amino]-2,2-dimethyl-2H-1-benzopyran-6-carbonitrile;

(3R-trans)-N-[2-[N-(6-cyano-3,4-dihydro-3-hydroxy-2,2-dimethyl-2H-1-benzopyran-4-yl)phenylamino]ethyl]-2,2-dimethyl-propanamide;

(3R-trans)-N-[2-[N-(6-cyano-3,4-dihydro-3-hydroxy-2,2-dimethyl-2H-1-benzopyran-4-yl)phenylamino]ethyl]-N'-phenylurea;

(3R-trans)-N-[2-[N-(6-cyano-3,4dihydro-3-hydroxy-2,2-dimethyl-2H-1-benzopyran-4-yl)phenylamino]ethyl]-1-pyrrolidine-carboxamide;

(3R-trans)-3,4-dihydro-3-hydroxy-2,2-dimethyl-4-[N-[(2-oxo-1-pyrrolidinyl)ethyl)phenyl]amnino]-2H-1-benzopyran-6-carbonitrile;

(3R-trans)-[[(6-cyano-3,4-dihydro-3-hydroxy-2,2-dimethyl-2H-1-benzopyran-4-yl)(4-fluorophenyl)amino]methyl]phosphonic acid, diethyl ester;

[N-(4-clorophenyl)-N-(6-cyano-3,4-dihydro-2,2-dimethyl-2H-1-benzopyran-4-yl)amino]acetic acid, ethyl ester;

4-[(4-clorophenyl)(1H-imidazol-2-ylmethyl)amino]-3,4-dihydro-2,2-dimethyl-2H-1-benzopyran-6-carbonitrile;

(3R-trans)-3,4-dihydro-3-hydroxy-2,2-dimethyl-4-[N-[(3-methyl-1,2,4-oxadiazol-5-yl)methyl]phenylamino]-2H-1-benzopyran-6-carbonitrile;

(3R-trans)-4-[(4-chlorophenyl)[(3-methyl-1,2,4-oxadiazol-5-yl)methyl]amino]-3,4-dihydro-3-hydroxy-2,2-dimethyl-2H-1-benzopyran-6-carbonitrile;

(3R-trans)-4-[(4-fluorophenyl)[(3-methyl-1,2,4-oxadiazol-5yl-methyl]amino]-3,4-dihydro-3-hydroxy-2,2-dimethyl-2H-1-benzopyran-6-carbonitrile;

(3R-trans)-[N-[3,4-dihydro-3-hydroxy-2,2-dimethyl-7-(trifluoromethyl)-2H-1-benzopyran-4-yl]phenylamino]acetic acid, ethyl ester, (3R-trans)-3,4-dihydro-3-hydroxy-4-[N-[[3-(hydroxymethyl)-1,2,4-oxadiazol-5-yl)methyl]phenylamino]-2,2-dimethyl-2H-1-benzopyran-6-carbonitrile;

(3R-trans)-[N-[3,4-dihydro-3-hydroxy-2,2-dimethyl-8-(trifluoromethyl)-2H-1-benzopyran-4-yl]phenylarnino]acetic acid, ethyl ester;

(3R-trans)-4-[(4-chlorophenyl)[[3-(hydroxymethyl)-1,2,4-oxadiazol-5-yl]methyl]amino]-3,4dihydro-3-hydroxy-2,2-dimethyl-2H-1-benzopyran-6-carbonitrile;

(3R-trans)-4-[(4-fluorophenyl)[[3-(hydroxymethyl)-1,2,4-oxadiazol-5-yl]methyl]amino]-3,4-dihydro-3-hydroxy-2,2-dimethyl-2H-1-benzopyran-6-carbonitrile;

(3R-trans)-4-[N-[(3-amino-1,2,4-oxadiazol-5-yl)methyl]-phenylamino]-3,4-dihydro-3-hydroxy-2,2-dimethyl-2H-1-benzopyran-6-carbonitrile;

(3R-trans)-[N-(6-benzoyl-3,4-dihydro-3-hydroxy-2,2-dimethyl-2H-1-benzopyran-4-yl)phenylamino]acetic acid, ethyl ester;

(3R-trans)-[(6-cyano-3,4-dihydro-3-hydroxy-2,2-dimethyl-2H-1-benzopyran-4-yl)[4-fluoro-3-[(phenylmethoxy)carbonyl]phenyl]-aminolacetic acid, ethyl ester;

(3R-trans)-[[5-[[(6-cyano-3,4-dihydro-3-hydroxy-2,2-dimethyl-2H-1-benzopyran-4-yl)(4-fluorophenyl)amino]methyl]-1,2,4-oxadiazol-3-yl]methoxy]acetic acid;

(3R-trans)-[[5-[[(4-chlorophenyl)(6-cyano-3,4-dihydro-3-hydroxy-2,2-dimethyl-2H-1-benzopyran-4-yl)amino]methyl]-1,2,4-oxadiazol-3-yl]methoxy]acetic acid;

(3R-trans)-[(3-carboxy-4-fluorophenyl)(6-cyano-3,4-dihydro-3-hydroxy-2,2-dimethyl-2H-1-benzopyran-4-yl)amnino]acetic acid, ethyl ester;

(3R-trans)-4-[(4-fluorophenyl)[(2-methyl-2H-tetrazol-5-yl)-methyl]amino-3,4dihydro-3-hydroxy-2,2-dimethyl-2H-1-benzopyran-6-carbonitrile;

(3R-trans)-4-[(4-fluorophenyl)[(1-methyl-1H-tetrazol-5-yl)-methyl]amino-3,4dihydro-3-hydroxy-2,2-dimethyl-2H-1-benzopyran-6-carbonitrile;

(3R-trans)-3,4-dihydro-3-hydroxy-2,2-dimethyl-4[N-[2-methylsulfinyl)ethyl]phenylamino]-2H-1-benzopyran-6-carbonitrile;

(3R-trans)-3,4dihydro-3-hydroxy-2,2-dimethyl-4-[N-[2-(methylsulfonyl)ethyl]phenylamino]-2H-1-benzopyran-6-carbonitrile;

(3R-taans)-4-[4-chloro-N-[(1H-imidazol-2-yl)methyl]-phenylamino]-3,4-dihydro-3-hydroxy-2,2-dimethyl-2H-1-benzopyran-6-carbonitrile, monohydrochloride;

(3R-trans)-4-[4-chloro-N-[(1H-imidazol-2-yl)methyl]-phenylamino]-3,4-dihydro-3-hydroxy-2,2-dimethyl-2H-1-benzopyran-6-carbonitrile, hydrogensulfate;

(3R-trans)-4-[4-chloro-N-[(1H-imidazol-2-yl)methyl]-phenylamino]-3,4-dihydro-3-hydroxy-2,2-dimethyl-2H-1-benzopyran-6-carbonitrile, methanesulfonate;

(3R-trans)-4-[4-chloro-N-[(1H-imidazol-2-yl)methyl]-phenylamino]-3,4-dihydro-3-hydroxy-2,2-dimethyl-2H-1-benzopyran-6-carbonitrile, phosphate;

(3R-trans)-4-[4-chloro-N-[(1H-imidazol-2-yl)methyl]-phenylamino]-3,4-dihydro-3-hydroxy-2,2-dimethyl-2H-1-benzopyran-6-carbonitrile, nitrate;

[3R-[3a,4β(R*)]]-3,4-dihydro-3-hydroxy-2,2-dimethyl-4[N-[[5-oxo-1-(phenylmethyl)-2-pyrrolidinyl]methyl]phenylamino]-2H-1-benzopyran-6-carbonitrile;

[3R-[3α,4β(S*)]]-3,4dihydro-3-hydroxy-2,2-dimethyl-4-[N-[[5-oxo-2-pyrrolidinyl)methyl]phenylamino]-2H-1-benzopyran-6-carbonitrile;

[3R-[3α,4β(R*)]]-3,4-dihydro-3-hydroxy-2,2-dimethyl-4 [N-[(5-oxo-2-pyrrolidinyl)methyl]phenylamino]-2H-1-benzopyran-6-carbonitrile;

(3R-trans)-4-[N-[(1,5-dimethyl-1H-pyrazol-3-yl)methyl]-phenylamino]-3,4-dihydro-3-hydroxy-2,2-dimethyl-2H-1-benzopyran-6-carbonitrile;

(3R-trans)-3,4dihydro-3-hydroxy-2,2-dimethyl-4-[N-[(5-methyl-1H-pyrazol-3-yl)methyl]phenylamino]-2H-1-benzopyran-6-carbonitrile;

(3R-trans)-4-[N-[(1,3-dimethyl-1H-pyrazol-5-yl)methyl] phenyl-amino]-3,4-dihydro-3-hydroxy-2,2-dimethyl-2H-1-benzopyran-6-carbonitrile;

[3R-[3α,4β-(Z)]]-4[N-(2-amino-4-oxo-2-pentenyl) phenyl-amino]-3,4-dihydro-3-hydroxy-2,2-dimethyl-2H-1-benzopyran-6-carbonitrile; or pharmaceutically acceptable salts thereof.

4. A pharmaceutical composition comprising a compound of claim 1 and a pharmaceutically acceptable carrier.

5. A method for treating ischemia comprising administering to a mammalian specie in need thereof a therapeutically effective amount of a composition of claim 4.

6. A compound of the formula or pharmaceutically acceptable salts thereof wherein a, b and d are all carbon atoms;

Y is a single bond, —O— or —S—;

$R^1$ is aryl or heterocyclo;

$R^2$ is —COOR, —CO-amino, —CO-substituted amino, amino, substituted amino, —NRCO-amino, —NRCO-substituted amino, —NRCOR, —NRSO$_2$R, —NR(C=NCN)-amino, —NR(C=NCN)-substituted amino, —SR, —SOR, —SO$_2$R, —OR, cyano, heterocyclo, —CH(OR)$_2$, (where Z is O or H$_2$);

$R^3$ is hydrogen, hydroxy or —OC(O)R;

$R^4$ and $R^5$ are each independently hydrogen, alkyl or arylalkyl, or $R^4$ and $R^5$ taken together with the carbon atom to which they are attached form a 5- to 7-membered carbocyclic ring;

$R^6$ is hydrogen, alkyl, haloalkyl, alkenyl, alkynyl, cycloalkyl, arylalkyl, (cycloalkyl)alkyl, —CN, —NO$_2$, —COR, —COOR, —CONHR, —CON(R)$_2$, —CF$_3$, —S-alkyl, —SOalkyl, —SO$_2$alkyl, halogen, amino, substituted amino, —O-alkyl, —OCF$_3$, —OCH$_2$CF$_3$, —OCOalkyl, —OCONRalkyl, —NRCOalkyl, —NRCOOalkyl or —NRCONR, tetrazolyl, imidazole, oxazole or triazole;

$R^7$ is hydrogen, alkyl, hydroxy, —O-alkyl, amino, substituted amino, —NHCOR, —CN or —NO$_2$;

X is alkyl; or X-$R^2$ together are aryl or heterocyclo when $R^1$ is heterocyclo: and n is an integer of 1 to 3.

7. A compound of the formula or pharmaceutically acceptable salts thereof wherein one of a, b and d is a nitrogen atom or —N(O)— and the others are carbon atoms;

Y is a single bond, —CH$_2$—, —C(O)—, —O—, —S— or —N(R$^8$)—;

$R^1$ is aryl or heterocyclo;

$R^2$ is —COOR$^8$, —CO-amino, —CO-substituted amino, amino, substituted amino, —NR$^8$CO-amino, —NR$^8$CO-substituted amino, —NR$^8$COR$^9$, —NR$^8$SO$_2$R$^9$, —NR$^8$(C=NCN)-amino, —NR$^8$(C=NCN)-substituted amino, —SR$^8$, —SOR$^8$, —SO$_2$R$^8$, —OR$^8$, cyano, heterocyclo, pyridine-N-oxide, —CH(OR$^8$)$_2$, (where Z is O or H$_2$) or $R^3$ is hydrogen, hydroxy or —OC(O)R$^8$;

$R^4$ and $R^5$ are each independently hydrogen, alkyl or arylalkyl, or $R^4$ and $R^5$ taken together with the carbon atom to which they are attached form a 5- to 7-membered carbocyclic ring;

$R^6$ is hydrogen, alkyl, haloalkyl, alkenyl, alkynyl, cycloalkyl, arylalkyl, (cycloalkyl)alkyl, —CN, —NO$_2$, —COR$^8$, —COOR$^8$, —CONHR$^8$, —CONR$^8$R$^9$, —CF$_3$, —S-alkyl, —SOalkyl, —SO$_2$alkyl,

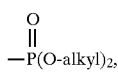

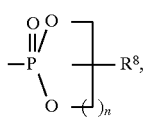

halogen, amino, substituted amino, —O-alkyl, —OCF3, —OCH$_2$CF$_3$, —OCOalkyl, —OCONR$^8$alkyl, —NR$^8$COalkyl, —NR$^8$COOalkyl or —NR$^8$CONR$^9$, tetrazolyl, imidazole, oxazole or triazole;

$R^7$ is hydrogen, alkyl, hydroxy, —O-alkyl, amino, substituted amino, —NHCOR$^8$, —CN or —NO$_2$;

$R^8$ and $R^9$ are independently hydrogen, alkyl, haloalkyl, aryl, arylalkyl, cycloalkyl or (cycloalkyl)alkyl;

X is alkyl; or X-R$^2$ together can be hydrogen, aryl or heterocyclo when $R^1$ is heterocyclo; and n is an integer of 1 to 3; provided that when $R^1$ is aryl, then $R^2$ is other than —COOR$^8$, amino, substituted amino, —OR$^8$ and cyano.

8. A compound of the formula

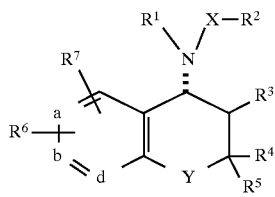

or pharmaceutically acceptable salts thereof wherein
one of a, b and d is a nitrogen atom or —N(O)— and the others are carbon atoms;

Y is a single bond, -CH$_2$—, —C(Q)—, —O—, —S— or —N(R)— where R is hydrozen, alkyl, haloalkvl, aryl, arylalkyl, cycloalkyl or (cycloalkyl)alkyl;

$R^1$ is aryl or heterocyclo;

$R^2$ is —COOR, —CO-amino, —CO-substituted amino, amino, substituted amino, —NRCO-amino, —NRCO-substituted amino, —NRCOR, —NRSO$_2$R, —NR(C=NCN)-amino, —NR(C=NCN)-substituted amino,

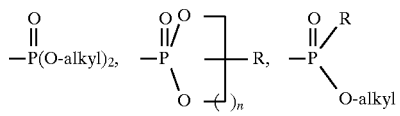

—SR, —SOR, —SO$_2$R, —OR, cyano, heterocyclo, —CH(OR)$_2$,

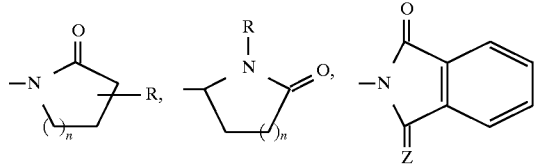

(where Z is O or H$_2$);

$R^3$ is hydrogen, hydroxy or —OC(O)R;

$R^4$ and $R^5$ are each independently hydrogen, alkyl or arylakyl, or $R^4$ and $R^5$ taken together with the carbon atom to which they are attached form a 5- to 7-membered carbocyclic ring;

$R^6$ is hydrogen, alkyl, haloalkyl, alkenyl, alkynyl, cycloalkyl, arylalkyl, (cycloalkyl)alkyl, —CN, —NO$_2$, —COR, —COOR, —CONHR, —CON(R)$_2$, —CF$_3$, —S-alkyl, —SOalkyl, —SO)alkyl,

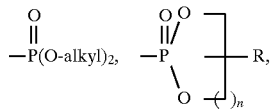

halogen, amino, substituted amino, —O-alkyl, —OCF$_3$, —OCH$_2$CF$_3$, —OCOalkyl, —OCONRalkyl, —NRCOalkyl, —NRCOOalkyl or —NRCONR, tetrazolyl, imidazole, oxazole or triazole;

$R^7$ is hydrogen, alkyl, hydroxy, —O-alkyl, amino, substituted amino, —NHCOR, —CN or —NO$_2$;

X is alkyl; or X-R$^2$ together are hydrogen, aryl or heterocyclo when $R^1$ is heterocyclo; and n is an integer of 1 to 3.

* * * * *